United States Patent
Themeli et al.

(10) Patent No.: US 10,370,452 B2
(45) Date of Patent: Aug. 6, 2019

(54) EFFECTIVE GENERATION OF TUMOR-TARGETED T CELLS DERIVED FROM PLURIPOTENT STEM CELLS

(71) Applicant: MEMORIAL SLOAN-KETTERING CANCER CENTER, New York, NY (US)

(72) Inventors: Maria Themeli, New York, NY (US); Michel Sadelain, New York, NY (US); Christopher C. Kloss, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 8 days.

(21) Appl. No.: 14/873,836

(22) Filed: Oct. 2, 2015

(65) Prior Publication Data

US 2016/0009813 A1    Jan. 14, 2016

Related U.S. Application Data

(63) Continuation of application No. PCT/US2014/032883, filed on Apr. 3, 2014.

(60) Provisional application No. 61/808,992, filed on Apr. 5, 2013, provisional application No. 61/808,092, filed on Apr. 3, 2013.

(51) Int. Cl.
| | | |
|---|---|---|
| A61K 35/12 | (2015.01) | |
| A61K 35/17 | (2015.01) | |
| A61K 39/00 | (2006.01) | |
| C07K 14/47 | (2006.01) | |
| C07K 16/28 | (2006.01) | |
| C07K 16/30 | (2006.01) | |
| C07K 14/705 | (2006.01) | |
| C07K 14/725 | (2006.01) | |
| C12N 5/0783 | (2010.01) | |

(52) U.S. Cl.
CPC .............. *C07K 16/30* (2013.01); *A61K 35/17* (2013.01); *A61K 39/0011* (2013.01); *C07K 14/47* (2013.01); *C07K 14/7051* (2013.01); *C07K 14/70521* (2013.01); *C07K 16/2803* (2013.01); *C12N 5/0638* (2013.01); *C12N 5/0646* (2013.01); *A61K 2035/124* (2013.01); *A61K 2039/5156* (2013.01); *A61K 2039/5158* (2013.01); *C07K 2317/24* (2013.01); *C07K 2317/56* (2013.01); *C07K 2317/622* (2013.01); *C07K 2319/03* (2013.01); *C07K 2319/33* (2013.01); *C07K 2319/70* (2013.01); *C07K 2319/74* (2013.01); *C12N 2506/45* (2013.01); *C12N 2510/00* (2013.01); *C12N 2740/13043* (2013.01); *C12N 2740/16043* (2013.01)

(58) Field of Classification Search
None
See application file for complete search history.

(56) References Cited

U.S. PATENT DOCUMENTS

| | | | |
|---|---|---|---|
| 7,446,190 B2 | 11/2008 | Sadelain et al. | |
| 8,389,282 B2 * | 3/2013 | Sadelain | A61K 39/0011 435/455 |
| 9,220,728 B2 * | 12/2015 | Sadelain | A61K 39/0011 |
| 2002/0018783 A1 | 2/2002 | Sadelain et al. | |
| 2004/0067583 A1 | 4/2004 | Bernstein et al. | |
| 2004/0171148 A1 | 9/2004 | Schmitt et al. | |
| 2010/0068192 A1 * | 3/2010 | Enoki | A61K 38/19 424/93.71 |
| 2013/0071414 A1 | 3/2013 | Dotti et al. | |
| 2013/0078226 A1 | 3/2013 | Nakauchi et al. | |
| 2014/0349402 A1 * | 11/2014 | Cooper | A61K 39/0011 435/455 |
| 2015/0342993 A1 * | 12/2015 | Kloss | C07K 14/70503 424/184.1 |
| 2015/0376296 A1 * | 12/2015 | Fedorov | A61K 35/17 424/93.71 |

FOREIGN PATENT DOCUMENTS

| | | |
|---|---|---|
| WO | WO 2009/091826 A2 | 7/2009 |
| WO | WO 2009/097140 A1 | 8/2009 |
| WO | WO 2012/012667 A2 | 1/2012 |
| WO | WO 2013/163171 A1 | 10/2013 |
| WO | WO 2013/176916 A1 | 11/2013 |

OTHER PUBLICATIONS

Brentjens et al. (Clin. Cancer Res. 2007 13 (18): 5426-5435).*
Figueiredo et al. (J. Mol. Med. 84: 425-437), "Figueiredo".*
Papapetrou et al. (Nature Biotechnology Jan. 2011 29(1): 73-81).*
Maher et al.(Nature Biotech. Jan. 2002 20:70-75).*
Gong et al. (Neoplasia Jun. 1999, 1(2): 123-127).*
Macmillan Dictionary (Kit, http://www.macmillandictionary.com/dictionary/american/kit, retrieved Aug. 23, 2013).*
Baldwin et al., "The timing of TCRα expression critically influences T cell development and selection," J. Exp. Med. 202(1):111-121 (2005).
Bonneville et al., "γδ T cell effector functions: a blend of innate programming and acquired plasticity," Nat. Rev. Immunol. 10:467-478 (2010).

(Continued)

*Primary Examiner* — Peter J Reddig
(74) *Attorney, Agent, or Firm* — Baker Botts L.L.P.

(57) ABSTRACT

The present invention relates to the field of adoptive immunotherapy. The invention provides methods for generating phenotypically defined, functional, and/or expandable T cells from pluripotent stem cells engineered through safe genetic modifications. The engineered cells may provide one or more of: 1) targeting a specific predetermined antigen expressed on the cell surface of a target cell in an HLA independent manner, 2) enhanced survival and functional potential 3) "off-the-shelf" T cells for administration to multiple recipients, eventually across immunogenic barriers, and/or 4) cytotoxic potential and anti-tumor activity.

96 Claims, 30 Drawing Sheets

Specification includes a Sequence Listing.

(56) References Cited

OTHER PUBLICATIONS

Brentjens et al., "CD19-targeted T cells rapidly induce molecular remissions in adults with chemotherapy-refractory acute lymphoblastic leukemia," Sci. Transl. Med. 5:177ra138 (2013).
Brentjens et al., "Eradication of systemic B-cell tumors by genetically targeted human T lymphocytes co-stimulated by CD80 and interleukin-15," Nat. Med. 9(3):279-286 (2003).
Brentjens et al., "Genetically Targeted T cells Eradicate Systemic Acute Lymphoblastic Leukemia Xenografts," Clin. Cancer Res 13(18):5426-5435 (2007).
Brentjens et al., "Safety and persistence of adoptively transferred autologous CD19-targeted T cells in patients with relapsed or chemotherapy refractory B-cell leukemias," Blood 118(18):4817-4828 (2011).
Brentjens et al., "Treatment of Chronic Lymphocytic Leukemia With Genetically Targeted Autologous T Cells: Case Report of an Unforeseen Adverse Event in a Phase I Clinical Trial," Molecular Therapy 18(4):666-668 (2010).
Cheng et al., "NK cell-based immunotherapy for malignant diseases," Cellular & Molecular Immunology 10:230-252 (2013).
Collins et al., "Donor Leukocyte Infusions in 140 Patients With Relapsed Malignancy After Allogeneic Bone Marrow Transplantation," J. Clin. Oncol. 15:433-444 (1997).
Cupedo et al., "Human fetal lymphoid tissue-inducer cells are interleukin 17-producing precursors to RORC+ CD127+ natural killer-like cells," Nat. Immunol. 10(1):66-74 (2009).
Dotti et al., "Review Fifteen Years of Gene Therapy Based on Chimeric Antigen Receptors: Are We Nearly There Yet?" Human Gene Therapy 20:1229-1239 (2009).
Doubrovina et al., "Adoptive immunotherapy with unselected or EBV-specific T cells for biopsy-proven EBV + lymphomas after allogeneic hematopoietic cell transplantation," Blood 119(11):2644-2656 (2012).
Egawa et al., "Lineage Diversion of T Cell Receptor Transgenic Thymocytes Revealed by Lineage Fate Mapping," PLoS One 1:e1512 (2008).
Ellis et al., "Benefits of Utilizing Gene-Modified iPSCs for Clinical Applications," Cell Stem Cell 7:429-430 (2010).
Fournie et al., "What lessons can be learned from γδ T cell-based cancer immunotherapy trials?," Cell. Mol. Immunol. 10:35-41 (2013).
Goff et al., "Tumor Infiltrating Lymphocyte Therapy for Metastatic Melanoma: Analysis of Tumors Resected for TIL," J. Immunother. 33:840-847 (2010).
Grambsch et al., "Proportional hazards tests and diagnostics based on weighted residuals," Biometrika 81(3):515-526 (1994).
International Search Report dated Jan. 21, 2015 in International Application No. PCT/US2014/032883.
Jena et al., "Redirecting T-cell specificity by introducing a tumor-specific chimeric antigen receptor," Blood 116(7):1035-1044 (2010).
Kalos et al., "T Cells with Chimeric Antigen Receptors Have Potent Antitumor Effects and Can Establish Memory in Patients with Advanced Leukemia," Sci. Transl. Med. 3:95ra73 (2011).
Kennedy et al., "T Lymphocyte Potential Marks the Emergence of Definitive Hematopoietic Progenitors in Human Pluripotent Stem Cell Differentiation Cultures," Cell Rep. 2:1722-1735 (2012).
Klingemann, "Cellular therapy of cancer with natural killer cells-where do we stand?" Cytotherapy 15:1185-1194 (2013).
Knorr et al., "Pluripotent stem cell-derived natural killer cells for cancer therapy," Translational Research 156(3):147-154 (2010).
Knorr et al: "Engineering Human Pluripotent Stem Cells for Enhanced Lymphocyte Development and Function, A Dissertation Submitted to the Faculty of the Graduate School of the University of Minnesota by," Oct. 2012.
Kochenderfer et al., "B-cell depletion and remissions of malignancy along with cytokine-associated toxicity in a clinical trial of anti-CD19 chimeric-antigen-receptor-transduced T cells," Blood 119(12):2709-2720 (2012).
Kowolik et al., "CD28 Costimulation Provided through a CD19-Specific Chimeric Antigen Receptor Enhances In vivo Persistence and Antitumor Efficacy of Adoptively Transferred T Cells," Cancer Res 66(22):10995-11004 (2006).
Luevano et al., "Generation of natural killer cells from hematopoietic stem cells in vitro for immunotherapy," Cellular & Molecular Immunology 9:310-320 (2012).
Maher et al., "Human T-lymphocyte cytotoxicity and proliferation directed by a single chimeric TCR ζ/CD28 receptor," Nat. Biotechnol. 20:70-75 (2002).
Markley et al., "IL-7 and IL-21 are superior to IL-2 and IL-15 in promoting human T cell-mediated rejection of systemic lymphoma in immunodeficient mice," Blood 115(17):3508-3519 (2010).
Muranski et al., "Th17 cells are long lived and retain a stem cell-like molecular signature," Immunity 35(6):972-985 (2011).
Murry et al., "Differentiation of Embryonic Stem Cells to Clinically Relevant Populations: Lessons from Embryonic Development," Cell 132:661-680 (2008).
Ness-Schwickerath et al., "Regulation and function of IL-17A- and IL-22-producing γδ T cells," Cell. Mol. Life Sci. 68(14):2371-2390 (2011).
Pang et al., "Understanding the complexity of γδ T-cell subsets in mouse and human," Immunology 136:283-290 (2012).
Papapetrou et al., "Derivation of genetically modified human pluripotent stem cells with integrated transgenes at unique mapped genomic sites," Nature Protocols 6(9):1274-1289 (2011).
Papapetrou et al., "Genomic safe harbors permit high β-globin transgene expression in thalassemia induced pluripotent stem cells," Nat. Biotechnol. 29(1):73-78 (2011).
Pont et al., "The gene expression profile of phosphoantigen-specific human γδ T lymphocytes is a blend of αβ T-cell and NK-cell signatures," Eur. J. Immunol. 42:228-240 (2012).
Porter et al., "Chimeric Antigen Receptor-Modified T Cells in Chronic Lymphoid Leukemia," New England Journal of Medicine 365:725-733 (2011).
Provasi et al., "Editing T cell specificity towards leukemia by zinc finger nucleases and lentiviral gene transfer," Nat. Med. 18(5):807-815 (2012).
Ramos et al., "Chimeric Antigen Receptor (CAR)-Engineered Lymphocytes for Cancer Therapy," Expert Opinion on Biological Therapy 11(7):855-873 (2011).
Riddell et al., "Principles for Adoptive T Cell Therapy of Human Viral Diseases," Annu. Rev. Immunol. 13:545-586 (1995).
Riolobos et al., "HLA Engineering of Human Pluripotent Stem Cells," Mol. Ther. 21(6):1232-1241 (2013).
Sadelain et al., "Targeting Tumours with Genetically Enhanced T Lymphocytes," Nat. Rev. Cancer 3:35-45 (2003).
Sadelain et al., "The Basic Principles of Chimeric Antigen Receptor (CAR) Design," Cancer Discovery 3(4):388-398 (2013).
Sadelain et al., "The promise and potential pitfalls of chimeric antigen receptors," Current Opinion in Immunology 21(2):215-223 (2009).
Schmitt et al., "Induction of T Cell Development and establishment of T cell competence from embryonic stem cells differentiated in vitro," Nature Immunology 5(4):410-417 (2004).
Schmitt et al., "Induction of T Cell Development from Hematopoietic Progenitor Cells by Delta-like-1 In Vitro," Immunity 17:749-756 (2002).
Slukvin, "Deciphering the hierarchy of angiohematopoietic progenitors from human pluripotent stem cells," Cell Cycle 12(5):720-727 (2013).
Spits et al., "Innate Lymphoid Cells: Emerging Insights in Development, Lineage Relationships, and Function," Annu. Rev. Immunol. 30:647-675 (2012).
Takahashi et al., "Induction of pluripotent stem cells from adult human fibroblasts by defined factors," Cell 131:861-872 (2007).
Taylor et al., "Generating an iPSC Bank for HLA-Matched Tissue Transplantation Based on Known Donor and Recipient HLA Types," Cell Stem Cell 11:147-152 (2012).
Terrence et al., "Premature Expression of T Cell Receptor (TCR)αβ Suppresses TCRγδ Gene Rearrangement but Permits Development of γδ Lineage T Cells," J. Exp. Med. 192(4):537-548 (2000).

(56) References Cited

OTHER PUBLICATIONS

Themeli et al., "Generation of tumor-targeted human T lymphocytes from induced pluripotent stem cells for cancer therapy," Nature Biotechnology 31(10):928-933 (2013).
Timmermans et al., "Generation of T Cells from Human Embryonic Stem Cell-Derived Hematopoietic Zones," J. Immunol. 182:6879-6888 (2009).
Torikai et al., "A foundation for universal T-cell based immunotherapy: T cells engineered to express a CD19-specific chimeric-antigen-receptor and eliminate expression of endogenous TCR," Blood 119(24):5697-5705 (2012).
Turatti et al., "Redirected Activity of Human Antitumor Chimeric Immune Receptors is Governed by Antigen and Receptor Expression Levels and Affinity of Interaction," J. Immunother. 30:684-693 (2007).
Yuan et al., "Lin28b reprograms adult bone marrow hematopoietic progenitors to mediate fetal-like lymphopoiesis," Science 335 (6073): 1195-1200 (2012).
Zhao et al., "Extrathymic Generation of Tumor-Specific T Cells from Genetically Engineered Human Hematopoietic Stem Cells via Notch Signaling," Cancer Res. 67(6):2425-2429 (2007).
Ahmed et al., "HER2-Specific T Cells Target Primary Glioblastoma Stem Cells and Induce Regression of Autologous Experimental Tumors," Clin Cancer Res 16(2):474-485 (2010).
Altenschmidt et al., "Specific cytotoxic T lymphocytes in gene therapy," J Mol. Med 75:259-266 (1997).
Brown et al., "Derivation of Induced Pluripotent Stem Cells from Human Peripheral Blood T Lymphocytes," PLoS One 5(6):e11373 (2010).
Chekmasova et al., "Enhanced Antitumor Efficacy of MUC-16 Targeted T Cells Further Modified to Constitutively Express the IL-12 Cytokine in a Syngeneic Model of Ovarian Cancer," Blood 118:4176 (2011).
Chicaybam et al., "Chimeric Antigen Receptors in Cancer Immuno-Gene Therapy: Current Status and Future Directions," International Reviews of Immunology 30:294-311 (2011).
Denman et al., "Membrane-Bound IL-21 Promotes Sustained Ex Vivo Proliferation of Human Natural Killer Cells," PLoS One 7(1):e30264 (2012).
Eshhar et al., "Specific activation and targeting of cytotoxic lymphocytes through chimeric single chains consisting of antibody-binding domains and the γ or ζ subunits of the immunoglobulin and T-cell receptors," PNAS USA 90:720-724 (1993).
Galic et al., "Generation of T Lineage Cells from Human Embryonic Stem Cells in a Feeder Free System," Stem Cells 27(1):100-107 (2009).
Greenfield et al., "CD28/B7 Costimulation: A Review," Critical Reviews in Immunology 18:389-418 (1998).
Harding et al., "CD28-mediated signalling co-stimulates murine T cells and prevents induction of anergy in T-cell clones," Nature 356:607-609 (1992).
June, "Adoptive T cell therapy for cancer in the clinic," The Journal of Clinical Investigation 117(6):1466-1476 (2007).
Kennedy et al., "T Lymphocyte Potential Marks the Emergence of Definitive Hematopoietic Progenitors in Human Pluripotent Stem Cell Differentiation Cultures," Cell Reports 2:1722-1735 (2012).
Krause et al., "Antigen-dependent CD28 Signaling Selectively Enhances Survival and Proliferation in Genetically Modified Activated Human Primary T Lymphocytes," J. Exp. Med. 188(4):619-626 (1998).
Latouche et al., "Induction of human cytotoxic T lymphocytes by artificial antigen-presenting cells," Nature Biotechnology 18:405-409 (2000).
Lenschow et al., "CD28/B7 System of T Cell Costimulation," Annu. Rev. Immunol. 14:233-258 (1996).
Loh et al., "Reprogramming of T Cells from Human Peripheral Blood," Cell Stem Cell 7(1):15-19 (2010).
Ni et al., "Human Pluripotent Stem Cells Produce Natural Killer Cells That Mediate Anti-HIV-1 Activity by Utilizing Diverse Cellular Mechanisms," Journal of Virology 85(1):43-50 (2011).
Nishimura et al., "Generation of Rejuvenated Antigen-Specific T Cells by Reprogramming to Pluripotency and Redifferentiation," Cell Stem Cell 12:114-126 (2013).
Paillard, "Immunotherapy with T Cells Bearing Chimeric Antitumor Receptors," Human Gene Therapy 10:151-153 (1999).
Sadelain et al., "Safe harbours for the integration of new DNA in the human genome," Nature Reviews Cancer 12:51-58 (2012).
Salvagiotto et al., "A Defined, Feeder-Free, Serum-Free System to Generate In Vitro Hematopoietic Progenitors and Differentiated Blood Cells from hESCs and hiPSCs," PLoS One 6(3):e17829 (2011).
Seki et al., "Generation of Induced Pluripotent Stem Cells from Human Terminally Differentiated Circulating T Cells," Cell Stem Cell 7:11-14 (2010).
Stacey et al., "Banking Human Induced Pluripotent Stem Cells: Lessons Learned from Embryonic Stem Cells?" Cell Stem Cell 13:385-388 (2013).
Staerk et al., "Reprogramming of peripheral blood cells to induced pluripotent stem cells," Cell Stem Cell 7(1):20-24 (2010).
Stephan et al., "T-cell encoded CD80 and 4-1BBL induce auto- and transcostimulation, resulting in potent tumor rejection," Nature Medicine 13(12):1440-1449 (2007).
Takahashi et al., "Induction of Pluripotent Stem Cells from Mouse Embryonic and Adult Fibroblast Cultures by Defined Factors," Cell 126:663-676 (2006).
Timmermans et al., "Generation of T Cells from Human Embryonic Stem Cell-Derived Hematopoietic Zones," The Journal of Immunology 182:6879-6888 (2009).
Turner et al., "Toward the Development of a Global Induced Pluripotent Stem Cell Library," Cell Stem Cell 13:382-384 (2013).
Vizcardo et al., "Regeneration of Human Tumor Antigen-Specific T Cells from iPSCs Derived from Mature CD8+ T Cells," Cell Stem Cell 12:31-36 (2013).
Wakao et al., "Expansion of Functional Human Mucosal-Associated Invariant T Cells via Reprogramming to Pluripotency and Redifferentiation," Cell Stem Cell 12:546-558 (2013).
Ward et al., "CD28: a signalling perspective," Biochem. J. 318:361-377 (1996).
Woll et al., "Human Embryonic Stem Cell-Derived NK Cells Acquire Functional Receptors and Cytolytic Activity," J Immunol 175:5095-5103 (2005).
Woll et al., "Human embryonic stem cells differentiate into a homogeneous population of natural killer cells with potent in vivo antitumor activity," Blood 113:6094-6101 (2009).
Zhong et al., "Chimeric Antigen Receptors Combining 4-1BB and CD28 Signaling Domains Augment PI3kinase/AKT/Bcl-XL Activation and CD8 + T Cell—mediated Tumor Eradication," Molecular Therapy 18(2):413-420 (2010).
Singh et al., "Naive Cd19-Specific T Cells Exhibit Superior Proliferation and Potential for Adoptive Immunotherapy," Biology of Blood and Marrow Transplantation, 18(2): S311 (2012).

* cited by examiner

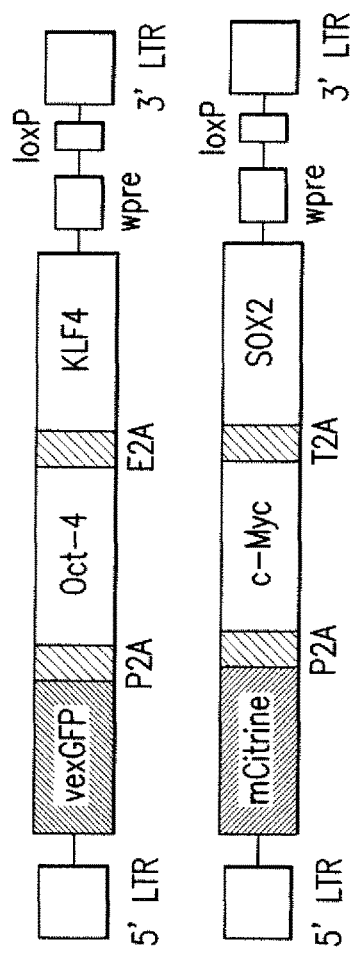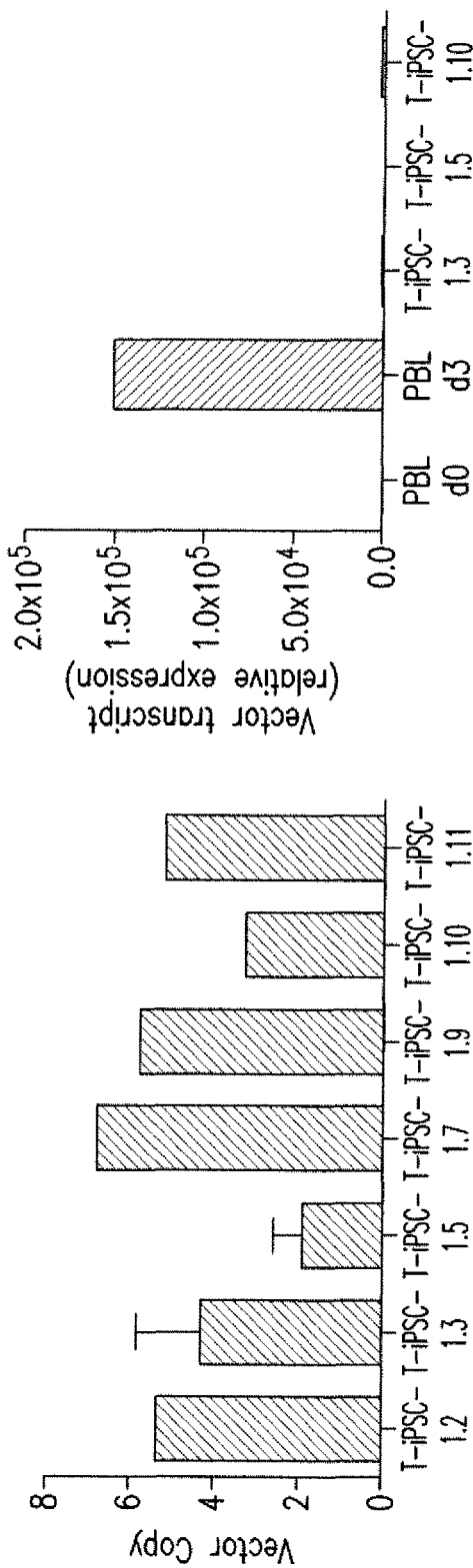
FIG. 4a
FIG. 4b
FIG. 4c

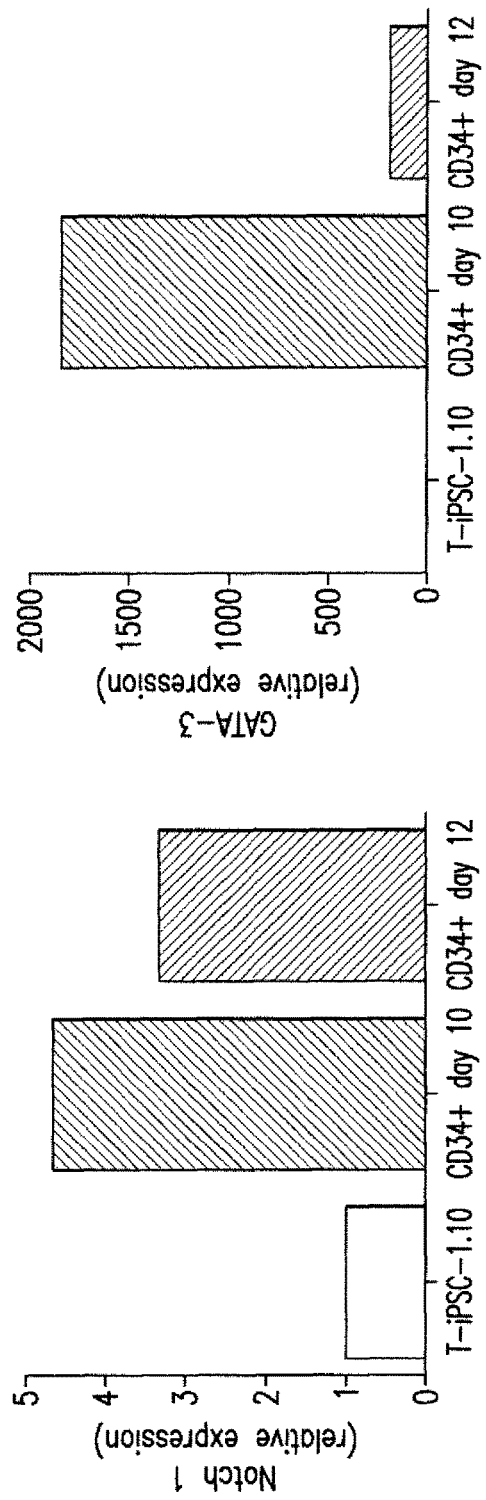
FIG. 7a
FIG. 7b
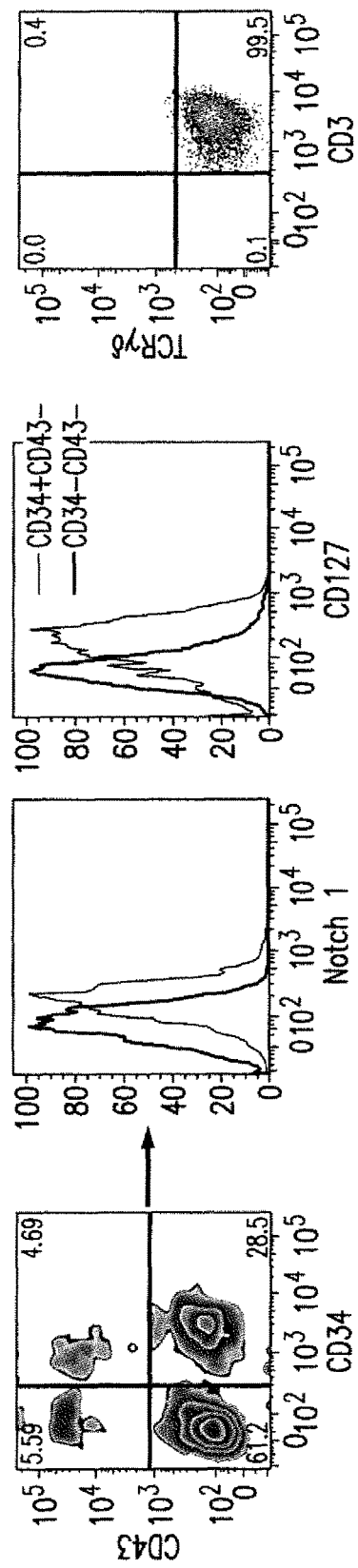
FIG. 8a

```
                        SEQUENCE LISTING

<160> NUMBER OF SEQ ID NOS: 27

<210> SEQ ID NO 1
<211> LENGTH: 164
<212> TYPE: PRT
<213> ORGANISM: Homo sapiens

<400> SEQUENCE: 1

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 2
<211> LENGTH: 235
<212> TYPE: PRT
<213> ORGANISM: Homo sapiens

<400> SEQUENCE: 2

Met Ala Leu Pro Val Thr Ala Leu Leu Leu Pro Leu Ala Leu Leu Leu
1               5                   10                  15
```

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 3
<211> LENGTH: 220
<212> TYPE: PRT
<213> ORGANISM: Homo sapiens

<400> SEQUENCE: 3

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Tyr Leu Asp Asn Glu Lys Ser
        115                 120                 125

Asn Gly Thr Ile Ile His Val Lys Gly Lys His Leu Cys Pro Ser Pro
130                 135                 140

Leu Phe Pro Gly Pro Ser Lys Pro Phe Trp Val Leu Val Val Val Gly
145                 150                 155                 160

-continued

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
                195                 200                 205

Tyr Ala Pro Pro Arg Asp Phe Ala Ala Tyr Arg Ser
                210                 215                 220

<210> SEQ ID NO 4
<211> LENGTH: 123
<212> TYPE: PRT
<213> ORGANISM: Homo sapiens

<400> SEQUENCE: 4

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Trp Lys His Leu Cys Pro Ser Pro Leu
                35                  40                  45

Phe Pro Gly Pro Ser Lys Pro Phe Trp Val Leu Val Val Val Gly Gly
            50                  55                  60

Val Leu Ala Cys Tyr Ser Leu Leu Val Thr Val Ala Phe Ile Ile Phe
65                  70                  75                  80

Trp Val Arg Ser Lys Arg Ser Arg Leu Leu His Ser Asp Tyr Met Asn
                85                  90                  95

Met Thr Pro Arg Arg Pro Gly Pro Thr Arg Lys His Tyr Gln Pro Tyr
                100                 105                 110

Ala Pro Pro Arg Asp Phe Ala Ala Tyr Arg Ser
                115                 120

<210> SEQ ID NO 5
<211> LENGTH: 277
<212> TYPE: PRT
<213> ORGANISM: Homo sapiens

<400> SEQUENCE: 5

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
                35                  40                  45

Gly Asn Gly Met Val Ser Arg Cys Ser Arg Ser Gln Asn Thr Val Cys
            50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
                115                 120                 125

Pro Pro Gly His Phe Ser Pro Gly Asp Asn Gln Ala Cys Lys Pro Trp
                130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 6
<211> LENGTH: 255
<212> TYPE: PRT
<213> ORGANISM: Homo sapiens

<400> SEQUENCE: 6

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly

```
                225                 230                 235                 240

Cys Ser Cys Arg Phe Pro Glu Glu Glu Gly Gly Cys Glu Leu
                245                 250                 255

<210> SEQ ID NO 7
<211> LENGTH: 199
<212> TYPE: PRT
<213> ORGANISM: Homo sapiens

<400> SEQUENCE: 7

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 8
<211> LENGTH: 223
<212> TYPE: PRT
<213> ORGANISM: Homo sapiens

<400> SEQUENCE: 8

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
```

```
            100                 105                 110
Asn Leu Thr Ile Gln Gly Leu Arg Ala Met Asp Thr Gly Leu Tyr Ile
        115                 120                 125

Cys Lys Val Glu Leu Met Tyr Pro Pro Tyr Tyr Leu Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                    165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
        210                 215                 220

<210> SEQ ID NO 9
<211> LENGTH: 288
<212> TYPE: PRT
<213> ORGANISM: Homo sapiens

<400> SEQUENCE: 9

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                    165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Val Pro
225                 230                 235                 240

Cys Val Pro Glu Gln Thr Glu Tyr Ala Thr Ile Val Phe Pro Ser Gly
                    245                 250                 255
```

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 10
<211> LENGTH: 525
<212> TYPE: PRT
<213> ORGANISM: Homo sapiens

<400> SEQUENCE: 10

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
        370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
            515                 520                 525

<210> SEQ ID NO 11
<211> LENGTH: 370
<212> TYPE: PRT
<213> ORGANISM: Homo sapiens

<400> SEQUENCE: 11

Met Leu Gly Gln Val Val Thr Leu Ile Leu Leu Leu Leu Lys Val
1               5                   10                  15

Tyr Gln Gly Lys Gly Cys Gln Gly Ser Ala Asp His Val Val Ser Ile
                20                  25                  30

Ser Gly Val Pro Leu Gln Leu Gln Pro Asn Ser Ile Gln Thr Lys Val
            35                  40                  45

Asp Ser Ile Ala Trp Lys Lys Leu Leu Pro Ser Gln Asn Gly Phe His
50                  55                  60

His Ile Leu Lys Trp Glu Asn Gly Ser Leu Pro Ser Asn Thr Ser Asn
65                  70                  75                  80

Asp Arg Phe Ser Phe Ile Val Lys Asn Leu Ser Leu Leu Ile Lys Ala
                85                  90                  95

Ala Gln Gln Gln Asp Ser Gly Leu Tyr Cys Leu Glu Val Thr Ser Ile
                100                 105                 110

Ser Gly Lys Val Gln Thr Ala Thr Phe Gln Val Phe Val Phe Glu Ser
            115                 120                 125

Leu Leu Pro Asp Lys Val Glu Lys Pro Arg Leu Gln Gly Gln Gly Lys
            130                 135                 140

Ile Leu Asp Arg Gly Arg Cys Gln Val Ala Leu Ser Cys Leu Val Ser
145                 150                 155                 160

Arg Asp Gly Asn Val Ser Tyr Ala Trp Tyr Arg Gly Ser Lys Leu Ile
                165                 170                 175

Gln Thr Ala Gly Asn Leu Thr Tyr Leu Asp Glu Glu Val Asp Ile Asn
            180                 185                 190

Gly Thr His Thr Tyr Thr Cys Asn Val Ser Asn Pro Val Ser Trp Glu

```
            195                 200                 205
Ser His Thr Leu Asn Leu Thr Gln Asp Cys Gln Asn Ala His Gln Glu
    210                 215                 220

Phe Arg Phe Trp Pro Phe Leu Val Ile Ile Val Ile Leu Ser Ala Leu
225                 230                 235                 240

Phe Leu Gly Thr Leu Ala Cys Phe Cys Val Trp Arg Arg Lys Arg Lys
                245                 250                 255

Glu Lys Gln Ser Glu Thr Ser Pro Lys Glu Phe Leu Thr Ile Tyr Glu
            260                 265                 270

Asp Val Lys Asp Leu Lys Thr Arg Arg Asn His Glu Gln Glu Gln Thr
        275                 280                 285

Phe Pro Gly Gly Gly Ser Thr Ile Tyr Ser Met Ile Gln Ser Gln Ser
290                 295                 300

Ser Ala Pro Thr Ser Gln Glu Pro Ala Tyr Thr Leu Tyr Ser Leu Ile
305                 310                 315                 320

Gln Pro Ser Arg Lys Ser Gly Ser Arg Lys Arg Asn His Ser Pro Ser
                325                 330                 335

Phe Asn Ser Thr Ile Tyr Glu Val Ile Gly Lys Ser Gln Pro Lys Ala
            340                 345                 350

Gln Asn Pro Ala Arg Leu Ser Arg Lys Glu Leu Glu Asn Phe Asp Val
        355                 360                 365

Tyr Ser
    370

<210> SEQ ID NO 12
<211> LENGTH: 289
<212> TYPE: PRT
<213> ORGANISM: Homo sapiens

<400> SEQUENCE: 12

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
                20                  25                  30

Ser Cys Asp Val Gln Leu Tyr Ile Lys Arg Gln Ser Glu His Ser Ile
            35                  40                  45

Leu Ala Gly Asp Pro Phe Glu Leu Glu Cys Pro Val Lys Tyr Cys Ala
        50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Val Leu Pro Asn Asp Asn Gly Ser
                100                 105                 110

Tyr Arg Cys Ser Ala Asn Phe Gln Ser Asn Leu Ile Glu Ser His Ser
            115                 120                 125

Thr Thr Leu Tyr Val Thr Asp Val Lys Ser Ala Ser Glu Arg Pro Ser
        130                 135                 140

Lys Asp Glu Met Ala Ser Arg Pro Trp Leu Leu Tyr Ser Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190
```

```
Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Gly Ser
225                 230                 235                 240

Glu Val Tyr Ser Asn Pro Cys Leu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser

<210> SEQ ID NO 13
<211> LENGTH: 183
<212> TYPE: PRT
<213> ORGANISM: Homo sapiens

<400> SEQUENCE: 13

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 14
<211> LENGTH: 255
<212> TYPE: PRT
<213> ORGANISM: Homo sapiens

<400> SEQUENCE: 14

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
```

```
            35                  40                  45
Pro Pro Asn Ser Phe Ser Ser Ala Gly Gly Gln Arg Thr Cys Asp Ile
 50                  55                  60

Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                     85                  90                  95

Ala Gly Cys Ser Met Cys Glu Gln Asp Cys Lys Gln Gly Gln Glu Leu
                    100                 105                 110

Thr Lys Lys Gly Cys Lys Asp Cys Cys Phe Gly Thr Phe Asn Asp Gln
                    115                 120                 125

Lys Arg Gly Ile Cys Arg Pro Trp Thr Asn Cys Ser Leu Asp Gly Lys
                130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                    165                 170                 175

Pro Ala Arg Glu Pro Gly His Ser Pro Gln Ile Ile Ser Phe Phe Leu
                    180                 185                 190

Ala Leu Thr Ser Thr Ala Leu Leu Phe Leu Leu Phe Phe Leu Thr Leu
                    195                 200                 205

Arg Phe Ser Val Val Lys Arg Gly Arg Lys Lys Leu Leu Tyr Ile Phe
                210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                    245                 250                 255

<210> SEQ ID NO 15
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (486)..(486)
<223> OTHER INFORMATION: Any amino acid

<400> SEQUENCE: 15

Met Ala Leu Pro Val Thr Ala Leu Leu Leu Pro Leu Ala Leu Leu Leu
 1               5                  10                  15

His Ala Glu Val Lys Leu Gln Gln Ser Gly Ala Glu Leu Val Arg Pro
                20                  25                  30

Gly Ser Ser Val Lys Ile Ser Cys Lys Ala Ser Gly Tyr Ala Phe Ser
             35                  40                  45

Ser Tyr Trp Met Asn Trp Val Lys Gln Arg Pro Gly Gln Gly Leu Glu
         50                  55                  60

Trp Ile Gly Gln Ile Tyr Pro Gly Asp Gly Asp Thr Asn Tyr Asn Gly
 65                  70                  75                  80

Lys Phe Lys Gly Gln Ala Thr Leu Thr Ala Asp Lys Ser Ser Ser Thr
                 85                  90                  95

Ala Tyr Met Gln Leu Ser Gly Leu Thr Ser Glu Asp Ser Ala Val Tyr
                100                 105                 110

Phe Cys Ala Arg Lys Thr Ile Ser Ser Val Val Asp Phe Tyr Phe Asp
```

```
            115                 120                 125
Tyr Trp Gly Gln Gly Thr Thr Val Thr Val Ser Ser Gly Gly Gly
    130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Ile Glu Val Met Tyr Pro
            260                 265                 270

Pro Pro Tyr Leu Asp Asn Glu Lys Ser Asn Gly Thr Ile Ile His Val
        275                 280                 285

Lys Gly Lys His Leu Cys Pro Ser Pro Leu Phe Pro Gly Pro Ser Lys
    290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser Arg Val Lys Phe Ser Arg Ser Ala Glu Pro Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg Xaa
                485

<210> SEQ ID NO 16
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 16

| | | |
|---|---|---|
| ccatggctct cccagtgact gccctactgc ttccctagc gcttctcctg catgcagagg | 60 |
| tgaagctgca gcagtctggg gctgagctgg tgaggcctgg gtcctcagtg aagatttcct | 120 |
| gcaaggcttc tggctatgca ttcagtagct actggatgaa ctgggtgaag cagaggcctg | 180 |
| gacagggtct tgagtggatt ggacagattt atcctggaga tggtgatact aactacaatg | 240 |
| gaaagttcaa gggtcaagcc acactgactg cagacaaatc ctccagcaca gcctacatgc | 300 |
| agctcagcgg cctaacatct gaggactctg cggtctattt ctgtgcaaga agaccatta | 360 |
| gttcggtagt agatttctac tttgactact ggggccaagg gaccacggtc accgtctcct | 420 |
| caggtggagg tggatcaggt ggaggtggat ctggtggagg tggatctgac attgagctca | 480 |
| cccagtctcc aaaattcatg tccacatcag taggagacag ggtcagcgtc acctgcaagg | 540 |
| ccagtcagaa tgtgggtact aatgtagcct ggtatcaaca gaaaccagga caatctccta | 600 |
| aaccactgat ttactcggca acctaccgga acagtggagt ccctgatcgc ttcacaggca | 660 |
| gtggatctgg gacagatttc actctcacca tcactaacgt gcagtctaaa gacttggcag | 720 |
| actatttctg tcaacaatat aacaggtatc cgtacacgtc cggaggggg accaagctgg | 780 |
| agatcaaacg ggcggccgca attgaagtta tgtatcctcc tccttaccta gacaatgaga | 840 |
| agagcaatgg aaccattatc catgtgaaag ggaaacacct ttgtccaagt cccctatttc | 900 |
| ccggaccttc taagcccttt tgggtgctgg tggtggttgg tggagtcctg gcttgctata | 960 |
| gcttgctagt aacagtggcc tttattattt tctgggtgag gagtaagagg agcaggctcc | 1020 |
| tgcacagtga ctacatgaac atgactcccc gccgccccgg gcccacccgc aagcattacc | 1080 |
| agccctatgc cccaccacgc gacttcgcag cctatcgctc cagagtgaag ttcagcagga | 1140 |
| gcgcagagcc ccccgcgtac cagcagggcc agaaccagct ctataacgag ctcaatctag | 1200 |
| gacgaagaga ggagtacgat gttttggaca agagacgtgg ccgggaccct gagatggggg | 1260 |
| gaaagccgag aaggaagaac cctcaggaag gcctgtacaa tgaactgcag aaagataaga | 1320 |
| tggcggaggc ctacagtgag attgggatga aggcgagcg ccggagggggc aaggggcacg | 1380 |
| atggccttta ccagggtctc agtacagcca ccaaggacac ctacgacgcc cttcacatgc | 1440 |
| aggccctgcc ccctcgcg | 1458 |

<210> SEQ ID NO 17
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

| | | |
|---|---|---|
| atggtgagca agggcgagga ggataacatg gccatcatca aggagttcat gcgcttcaag | 60 |
| gtgcacatgg agggctccgt gaacggccac gagttcgaga tcgagggcga gggcgagggc | 120 |
| cgcccctacg agggcaccca gaccgccaag ctgaaggtga ccaagggtgg ccccctgccc | 180 |
| ttcgcctggg acatcctgtc ccctcagttc atgtacggct ccaaggccta cgtgaagcac | 240 |
| cccgccgaca tccccgacta cttgaagctg tccttcccg agggcttcaa gtgggagcgc | 300 |
| gtgatgaact cgaggacgg cggcgtggtg accgtgaccc aggactcctc cctgcaggac | 360 |
| ggcgagttca tctacaaggt gaagctgcgc ggcaccaact tcccctccga cggccccgta | 420 |

```
atgcagaaga agaccatggg ctggaggcc tcctccgagc ggatgtaccc cgaggacggc      480
gccctgaagg gcgagatcaa gcagaggctg aagctgaagg acggcggcca ctacgacgct      540
gaggtcaaga ccacctacaa ggccaagaag cccgtgcagc tgcccggcgc ctacaacgtc      600
aacatcaagt tggacatcac ctcccacaac gaggactaca ccatcgtgga acagtacgaa      660
cgcgccgagg ccgccactc accggcggc atggacgagc tgtacaag                     708
```

<210> SEQ ID NO 18
<211> LENGTH: 3123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18

```
atggtgagca agggcgagga gctgttcacc ggggtggtgc ccatcctggt cgagctggac       60
ggcgacgtaa acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccttcggcta cggcctgatg tgcttcgccc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagct accagtccgc cctgagcaaa gaccccaacg agaagcgcga tcacatggtc      660
ctgctggagt tcgtgaccgc cgccgggatc actctcggca tggacgagct gtacaaggga      720
tctggagcaa caaacttctc actactcaaa caagcaggtg acgtggagga gaatcccggc      780
cctatgcccc tcaacgttag cttcaccaac aggaactatg acctcgacta cgactcggtg      840
cagccgtatt tctactgcga cgaggaggag aacttctacc agcagcagca gcagagcgag      900
ctgcagcccc cggcgcccag cgaggatatc tggaagaaat cgagctgct gcccacccccg      960 cccctgtccc ctagccgccg ctccgggctc tgctcgccct cctacgttgc ggtcacaccc     1020
ttctcccttc ggggagacaa cgacggcggt ggcgggagct ctccacggc cgaccagctg     1080 gagatggtga ccgagctgct gggaggagac atggtgaacc agagtttcat ctgcgacccg     1140
gacgacgaga ccttcatcaa aaacatcatc atccaggact gtatgtggag cggcttctcg     1200
gccgccgcca gctcgtctc agagaagctg gcctcctacc aggctgcgcg caaagacagc     1260
ggcagcccga accccgcccg cggccacagc gtctgctcca cctccagctt gtacctgcag     1320
gatctgagcg ccgccgcctc agagtgcatc gaccctcgg tggtcttccc ctaccctctc     1380
aacgacagca gctcgcccaa gtcctgcgcc tcgcaagact ccagcgcctt ctctccgtcc     1440
tcggattctc tgctctcctc gacggagtcc tcccgcagg gcagccccga gccctggtg     1500 ctccatgagg agacaccgcc caccaccagc agcgactctg aggaggaaca agaagatgag     1560
gaagaaatcg atgttgtttc tgtggaaaag aggcaggctc ctggcaaaag gtcagagtct     1620
ggatcacctt ctgctggagg ccacagcaaa cctcctcaca gccccactggt cctcaagagg     1680
```

```
tgccacgtct ccacacatca gcacaactac gcagcgcctc cctccactcg gaaggactat    1740
cctgctgcca agagggtcaa gttggacagt gtcagagtcc tgagacagat cagcaacaac    1800
cgaaaatgca ccagccccag gtcctcggac accgaggaga atgtcaagag gcgaacacac    1860
aacgtcttgg agcgccagag gaggaacgag ctaaaacgga gcttttttgc cctgcgtgac    1920
cagatcccgg agttggaaaa caatgaaaag gcccccaagg tagttatcct taaaaaagcc    1980
acagcataca tcctgtccgt ccaagcagag gagcaaaagc tcatttctga agaggacttg    2040
ttgcggaaac gacgagaaca gttgaaacac aaacttgaac agctacggaa ctcttgtgcg    2100
ggatctggac aatgtactaa ctacgctttg ttgaaactcg ctggcgatgt tgaaagtaac    2160
cccggtccca tgtacaacat gatggagacg gagctgaagc cgccgggccc gcagcaaact    2220 tcgggggggcg gcggcggcaa ctccaccgcg gcggcggccg gcggcaacca gaaaaacagc    2280
ccggaccgcg tcaagcggcc catgaatgcc ttcatggtgt ggtcccgcgg gcagcggcgc    2340
aagatggccc aggagaaccc caagatgcac aactcggaga tcagcaagcg cctgggcgcc    2400
gagtggaaac ttttgtcgga cacggagaag cggccgttca tcgacgaggc taagcggctg    2460
cgagcgctgc acatgaagga gcacccggat tataaatacc ggccccggcg gaaaaccaag    2520
acgctcatga agaaggataa gtacacgctg cccggcgggg tgctggcccc cggcggcaat    2580
agcatggcga gcggggtcgg ggtgggcgcc ggcctgggcg cgggcgtgaa ccagcgcatg    2640
gacagttacg cgcacatgaa cggctggagc aacggcagct acagcatgat gcaggaccag    2700
ctgggctacc cgcagcaccc gggcctcaat gcgcacggcg cagcgcagat gcagcccatg    2760
caccgctacg acgtgagcgc cctgcagtac aactccatga ccagctcgca gacctacatg    2820
aacggctcgc ccacctacag catgtcctac tcgcagcagg gcacccctgg catggctctt    2880
ggctccatgg gttcggtggt caagtccgag gccagctcca gccccctgt ggttacctct    2940 tcctcccact ccagggcgcc ctgccaggcc ggggacctcc gggacatgat cagcatgtat    3000
ctccccggcg ccgaggtgcc ggaacccgcc gcccccagca gacttcacat gtcccagcac    3060
taccagagcg gcccggtgcc cggcacggcc attaacggca cactgcccct ctcacacatg    3120
tga                                                                  3123
```

<210> SEQ ID NO 19
<211> LENGTH: 3339
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 19

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca cctttcagcta cggcgtgcag tgcttcagcc gctaccccga ccacatgaag     240
cagcacgact tcttcaagtc cgccatgccc gaaggctacg tccaggagcg caccatcagc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg cgaacttcaa gatccgccac aacatcgagg acggcagcgt gcagctcgcc     540
```

```
gaccactacc agcagaacac ccccatcggc gacggcccecg tgctgctgcc cgacaaccac      600
tacctgttca tccagtccgc cctgagcaaa gaccccaacg agaagcgcga tcacatggtc      660
ctgctggagt tcgtgaccgc cgccgggatc actcacggca tggacgagct gtacaaggga      720
tctggagcaa caaacttctc actactcaaa caagcaggtg acgtggagga gaatcccggc      780
cctatggcgg gacacctggc ttcggatttc gccttctcgc ccctccagg tggtggaggt       840 gatgggccag ggggggccgga gccgggctgg gttgatcctc ggacctggct aagcttccaa     900
ggccctcctg gagggccagg aatcgggccg ggggttgggc caggctctga ggtgtggggg      960
attcccccat gccccccgcc gtatgagttc tgtgggggga tggcgtactg tgggccccag     1020
gttggagtgg ggctagtgcc ccaaggcggc ttggagacct ctcagcctga gggtgaagca     1080
ggagtcgggg tggagagcaa ctccgatggg gcctccccgg agccctgcac cgtcaccect     1140 ggtgccgtga agctggagaa ggagaagctg gagcaaaacc cggaggagtc ccaggacatc     1200
aaagctctgc agaaagaact cgagcaattt gccaagctcc tgaagcagaa gaggatcacc     1260
ctgggatata cacaggccga tgtggggctc accctggggg ttctatttgg gaaggtattc     1320
agccaaacga ccatctgccg ctttgaggct ctgcagctta gcttcaagaa catgtgtaag     1380
ctgcggccct tgctgcagaa gtgggtggag gaagctgaca caatgaaaaa tcttcaggag    1440
atatgcaaag cagaaaccct cgtgcaggcc cgaaagagaa agcgaaccag tatcgagaac    1500
cgagtgagag gcaacctgga gaatttgttc ctgcagtgcc cgaaaccac actgcagcag     1560 atcagccaca tcgcccagca gcttgggctc gagaaggatg tggtccgagt gtggttctgt     1620
aaccggcgcc agaagggcaa gcgatcaagc agcgactatg cacaacgaga ggattttgag     1680
gctgctgggt ctccttttctc aggggaccca gtgtcctttc ctctggccccc agggccccat   1740 tttggtaccc caggctatgg gagccctcac ttcactgcac tgtactcctc ggtcccttc     1800 cctgagggggg aagccttcc ccctgtctct gtcaccactc tgggctctcc catgcattca    1860
aacggatctg gagagggcag aggaagtctt ctaacatgcg gtgacgtgga ggagaatccc    1920
ggccccatgg ctgtcagcga cgcgctgctc ccatctttct ccacgttcgc gtctggcccg    1980
gcgggaaggg agaagacact gcgtcaagca ggtgccccga ataaccgctg gcgggaggag    2040
ctctcccaca tgaagcgact tccccagtg cttcccggcc gccctatga cctggcggcg      2100 gcgaccgtgg ccacagacct ggagagcggc ggagccggtg cggcttgcgg cggtagcaac    2160
ctggcgcccc tacctcggag agagaccgag gagttcaacg atctcctgga cctggacttt    2220
attctctcca attcgctgac ccatcctccg gagtcagtgg ccgccaccgt gtcctcgtca    2280
gcgtcagcct cctcttcgtc gtcgccgtcg agcagcggcc ctgccagcgc gccctccacc    2340
tgcagcttca cctatccgat ccgggccggg aacgacccgg cgtggcgcc gggcggcacg     2400 ggcggaggcc tcctctatgg cagggagtcc gctccccctc cgacggctcc cttcaacctg    2460
gcggacatca cgacgtgag cccctcgggc ggcttcgtgg ccgagctcct gcggccagaa     2520
ttggacccgg tgtacattcc gccgcagcag ccgcagccgc caggtggcgg gctgatgggc    2580
aagttcgtgc tgaaggcgtc gctgagcgcc cctggcagcg agtacggcag cccgtcggtc    2640
atcagcgtca gcaaaggcag ccctgacggc agccaccccg tggtggtggc gccctacaac    2700
ggcgggccgc cgcgcacgtg ccccaagatc aagcaggagg cggtctcttc gtgcacccac    2760
ttgggcgctg gaccccctct cagcaatggc caccggccgg ctgcacacga cttccccctg    2820
gggcggcagc tccccagcag gactaccccg accctgggtc ttgaggaagt gctgagcagc    2880
```

-continued

```
agggactgtc accctgccct gccgcttcct cccggcttcc atccccaccc ggggcccaat    2940
tacccatcct tcctgcccga tcagatgcag ccgcaagtcc cgccgctcca ttaccaagag    3000
ctcatgccac ccggttcctg catgccagag gagcccaagc caaagagggg aagacgatcg    3060
tggccccgga aaaggaccgc cacccacact tgtgattacg cgggctgcgg caaaacctac    3120
acaaagagtt cccatctcaa ggcacacctg cgaacccaca caggtgagaa accttaccac    3180
tgtgactggg acggctgtgg atggaaattc gcccgctcag atgaactgac caggcactac    3240
cgtaaacaca cggggcaccg cccgttccag tgccaaaaat gcgaccgagc attttccagg    3300
tcggaccacc tcgccttaca catgaagagg catttttaa                          3339
```

<210> SEQ ID NO 20
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
agaacctaga acctcgctgg a                                              21

<210> SEQ ID NO 21
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
ctgcgatgcc gttctacttt g                                              21

<210> SEQ ID NO 22
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
tgaaacatac gttcccaaag agttt                                          25

<210> SEQ ID NO 23
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
ctctccttct cagaaagtgt gcatat                                         26

<210> SEQ ID NO 24
<211> LENGTH: 24
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic probe"

<400> SEQUENCE: 24
aggaccttac acagtcctgc tgac                                          24

<210> SEQ ID NO 25
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 25
tgctgaaaca ttcaccttcc atgcaga                                       27

<210> SEQ ID NO 26
<211> LENGTH: 4
<212> TYPE: PRT
<213> ORGANISM: Homo sapiens

<400> SEQUENCE: 26

Tyr Val Lys Met
1

<210> SEQ ID NO 27
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Gly Gly Ser Gly Gly Gly Ser Gly Gly Gly Ser Gly Gly Gly Ser
1               5                   10                  15
```

EFFECTIVE GENERATION OF TUMOR-TARGETED T CELLS DERIVED FROM PLURIPOTENT STEM CELLS

PRIORITY CLAIM

This application is a continuation of International Patent Application No. PCT/US2014/032883, filed Apr. 3, 2014, and claims priority to U.S. Provisional Application Nos. 61/808,092, filed Apr. 3, 2013, and 61/808,992, filed Apr. 5, 2013, to each of which priority is claimed and the contents of each of which are incorporated herein in their entireties.

SEQUENCE LISTING

The specification further incorporates by reference the Sequence Listing submitted via EFS on Oct. 2, 2015. Pursuant to 37 C.F.R. § 1.52(e)(5), the Sequence Listing text file, identified as SEQLISTING0727340325_SL.txt is 49.18 Kb and was created on Oct. 2, 2015. The Sequence Listing does not extend beyond the scope of the specification and thus does not contain new matter.

FIELD OF THE INVENTION

The present invention relates to the field of adoptive immunotherapy. The invention provides methods for generating phenotypically defined, functional, and/or expandable T cells from pluripotent stem cells (embryonic stem cells or induced pluripotent stem cells) engineered through safe genetic modifications. The engineered cells may provide one or more of: 1) targeting a specific predetermined antigen expressed on the cell surface of a target cell in an HLA-independent manner, 2) enhanced survival and functional potential 3) "off-the-shelf" T cells for administration to multiple recipients, eventually across immunogenic barriers, and/or 4) cytotoxic potential and anti-tumor activity.

BACKGROUND OF THE INVENTION

T lymphocytes are essential components of the immune system whose malfunction or absence are central to multiple pathologies, including inborn and acquired immune deficiencies, autoimmunity and cancer. A clinically relevant supply of functional antigen-specific T cells is thus useful for the treatment of a number of disorders, especially in the adoptive cancer immunotherapy setting.

Essential characteristics of adoptively transferred T lymphocytes (as in adoptive immunotherapy) required for the successful eradication of established tumors include their specificity for the tumor, their stimulatory capability, the number of tumor antigen-specific T cells, and their in vivo persistence. Current adoptive T cell therapies are limited by the lack of patient and tumor-specific T cells, including their rarity in the body, their failure to overcome a number of tumor immunoescape mechanisms, and their short life span, especially when using terminally differentiated or "exhausted" effector T cells, i.e. non proliferating T cells even when exposed to specific antigen.

Leukapheresis of patients or allogeneic donors are current sources of T lymphocytes used for adoptive cell therapy. However it is difficult to isolate and expand the typically low numbers of T cells reactive to a desired antigen, i.e. generate antigen-specific functional T cell clones. Furthermore, in some cases peripheral blood lymphocytes are not available, for example from immunodeficient patients.

Therefore, there is a need for therapeutically sufficient and functional antigen-specific T cells for effective use in immunotherapy.

SUMMARY OF THE INVENTION

The present invention relates to the field of adoptive immunotherapy. The invention provides methods for generating phenotypically defined, functional, and/or expandable T cells from pluripotent stem cells (embryonic stem cells (ESCs) or induced pluripotent stem cells (iPSCs) engineered through safe genetic modifications. The engineered cells may provide one or more of: 1) targeting a specific predetermined antigen expressed on the cell surface of a target cell in an HLA-independent manner, 2) enhanced survival and functional potential, and/or 3) cytotoxic potential and anti-tumor activity. In non-limiting embodiments, the engineered cells may be used as "off-the-shelf" T cells for administration to multiple recipients, eventually across immunogenic barriers.

As shown herein, engineering an iPSC or ESC to express a chimeric antigen receptor (CAR), which binds to a predetermined antigen for stimulating proliferation and function, dramatically augments T cell yield and provides (e.g., after differentiation into an effector cell by cell culture systems described in the present inventions) T cells with enhanced therapeutic properties. Such engineered and expanded T cells, which may or not express CD4 or CD8, and may share phenotypic features of either $\alpha\beta$ or $\gamma\delta$ T cells, are capable of antigen specific stimulation by target cells in an HLA-independent manner to provide T cell functional activity including cytokine production, cytotoxicity and cytostatic inhibition of tumor growth, e.g. as activity that reduces the amount of tumor load, along with continued proliferation over numerous generations of cell division. Enhanced T cell function can be delivered to the engineered cells through a range of costimulatory signals (e.g. CD28) provided by the CAR. Safe genetic modification of the T-iPSC is possible by targeting a safe genomic harbor site in the human genome. Specifically, compositions and methods for generating CAR-modified T-iPSC-derived T cells (or "iPSC-derived, CAR-expressing T cells) are provided for use in adoptive immunotherapy such as adoptive cancer immunotherapy. In some embodiments, CAR-modified T-iPSC-derived T cells are engineered for use in allogeneic setting by genetic manipulation of HLA cell surface expression.

The present invention provides a T cell that is generated from a pluripotent stem cell that expresses a chimeric antigen receptor (CAR). In certain embodiments, said T cell targets specifically to one antigen and antigen specificity of said T cell is HLA-independent. In one embodiment, said T cells express the CAR. In one embodiment, said CAR is encoded by a nucleic acid sequence that is a heterologous sequence. In one embodiment, said heterologous sequence is integrated into said T cell's' genome at a genomic safe harbor site. In some embodiments, the antigen is a tumor antigen or a pathogen antigen. In certain embodiments, the tumor antigen is selected from the group consisting of carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, an antigen of a cytomegalovirus (CMV) infected cell (e.g., a cell surface antigen), epithelial glycoprotein2 (EGP 2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma antigen family A, 1 (MAGE-AI), Mucin 16 (Muc-16), Mucin 1 (Muc-1), Mesothelin (MSLN), NKG2D ligands, cancer-testis antigen NY-ESO-1, oncofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), and Wilms tumor protein (WT-1). In one non-limiting embodiment, said T cells comprises a silenced gene selected from the group consisting of a HLA gene transcription factor and a beta-2 microglobulin for an HLA gene. In some embodiments, said CAR comprises an extracellular domain, a transmembrane domain and an intracellular domain. In some embodiments, said extracellular domain comprises an antigen-binding portion. In certain embodiments, said antigen-binding portion comprises single-chain variable fragments (scFv). In some embodiments, said transmembrane domain comprises a CD3ζ polypeptide, a CD4 polypeptide, a CD8 polypeptide, a CD28 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, and a BTLA polypeptide. In some embodiments, the said intracellular domain comprises a CD3ζ; polypeptide. In certain embodiments, said intracellular domain further comprises at least one costimulatory signaling region. Said costimulatory signaling region can comprise a CD28 polypeptide, a 4-1BB polypeptide, an OX40 polypeptide, an ICOS polypeptide, a PD-1 polypeptide, a LAG-3 polypeptide, a 2B4 polypeptide, a BTLA polypeptide, or a CTLA-4 polypeptide. In one embodiment, said CAR is 1928z. In certain embodiments, said T cells can be selected from the group consisting of T helper cells, cytotoxic T cells, memory T cells, regulatory T cells, Natural killer T cells, Mucosal associated invariant T cells, γδ T cells, and a combination thereof. In certain embodiments, the pluripotent stem cell is an embryonic stem cell or an induced pluripotent stem cell. In one embodiment, the pluripotent stem cell is an induced pluripotent stem cell.

The present invention also provides a cell population comprising the above-described T cell.

The present invention provides methods of using above-described T cell for the treatment of neoplasia, infectious disease, and other pathologies.

The present invention provides a method of reducing tumor burden in a subject. In one non-limiting embodiment, said method comprises administering a T cell generated from a pluripotent stem cell that expresses a chimeric antigen receptor (CAR) to a subject having tumor, thereby inducing tumor cell death in said subject. In certain embodiments, said T cell expresses the CAR. In some embodiments, antigen specificity of said T cell is HLA-independent. In certain embodiments, said T cell is cytotoxic to said tumor and does not induce graft vs. host disease in said subject. In one embodiment, said tumor cell expresses an tumor antigen and said T cell targets specifically to said tumor antigen. In one embodiment, said tumor antigen is selected from the group consisting of carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, an antigen of a cytomegalovirus (CMV) infected cell (e.g., a cell surface antigen), epithelial glycoprotein2 (EGP 2), epithelial glycoprotein-40 (EGP-40), epithelial cell adhesion molecule (Ep-CAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma antigen family A, 1 (MAGE-AI), Mucin 16 (Muc-16), Mucin 1 (Muc-1), Mesothelin (MSLN), NKG2D ligands, cancer-testis antigen NY-ESO-1, oncofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), and Wilms tumor protein (WT-1). In certain embodiments, the pluripotent stem cell is an embryonic stem cell or an induced pluripotent stem cell. In one embodiment, the pluripotent stem cell is an induced pluripotent stem cell. In one embodiment, said method reduces the number of tumor cells. In one embodiment, said method reduces tumor size. In one embodiment, said method eradicates the tumor in the subject. In certain embodiments, said T cell is selected from the group consisting of T helper cells, cytotoxic T cells, memory T cells, regulatory T cells, Natural killer T cells, Mucosal associated invariant T cells, γδ T cells, and a combination thereof. In one embodiment, said T cell has a silenced gene selected from the group consisting of a HLA gene transcription factor, class II transactivator (CIITA), a RAG gene, and a beta-2 microglobulin for an HLA gene. In certain embodiments, the subject is a human. In some embodiments, wherein said T cell expresses Foxp3. In certain embodiments, said pluripotent stem cell is derived from a T cell. In one embodiment, said pluripotent stem cell expresses one ligand for immunoregulatory T cell receptor, wherein said ligand is selected from the group consisting of PD-L1, CD48 and TNFRSF14. In another embodiment, said pluripotent stem cell expresses HLA-G. In certain embodiments, said pluripotent stem cell is derived from a viral-specific T cell. The viral-specific T cell can be a EBV-specific T-cell or a CMV-specific T-cell. In certain embodiments, said pluripotent stem cell is derived from a T cell that does not express a rearranged T-cell receptor (TCR).

The present invention provides a method of increasing survival of a subject having neoplasia. In one non-limiting embodiment, said method comprises administering a T cell generated from a pluripotent stem cell that expresses a chimeric antigen receptor to said subject diagnosed with neoplasia, thereby treating or preventing a neoplasia in said subject. In certain embodiments, the pluripotent stem cell is an embryonic stem cell or an induced pluripotent stem cell. In one embodiment, the pluripotent stem cell is an induced pluripotent stem cell. In certain embodiments, said T cell is cytotoxic to said neoplasia. In certain embodiments, said T cell expresses the CAR. In certain embodiments, said neoplasia cell expresses a tumor antigen and said T cell targets specifically to said tumor antigen. In certain embodiments, antigen-specificity of said T cell is HLA-independent. In certain embodiments, said neoplasia is selected from the group consisting of blood cancer, B cell leukemia, multiple myeloma, lymphoblastic leukemia (ALL), chronic lymphocytic leukemia, non-Hodgkin's lymphoma, ovarian cancer, prostate cancer, pancreatic cancer, lung cancer, breast cancer, and sarcoma, acute myeloid leukemia (AML). In certain embodiments, said T cell is selected from the group consisting of T helper cells, cytotoxic T cells, memory T cells, regulatory T cells, Natural killer T cells, Mucosal associated invariant T cells, γδ T cells, and a combination thereof. In one embodiment, said T cell has a silenced gene selected from the group consisting of a HLA gene transcription factor, class II transactivator (CIITA), a RAG gene, and a beta-2 microglobulin for an HLA gene. In certain embodiments, said subject is a human. In some embodiments, wherein said T cell expresses Foxp3. In certain embodiments, said pluripotent stem cell is derived from a T cell. In one embodiment, said pluripotent stem cell expresses one ligand for immunoregulatory T cell receptor, wherein said ligand is selected from the group consisting of PD-L1, CD48 and TNFRSF14. In another embodiment, said pluripotent stem cell expresses HLA-G. In certain embodiments, said pluripotent stem cell is derived from a viral-specific T cell. The viral-specific T cell can be a EBV-specific T-cell or a CMV-specific T-cell. In certain embodiments, said pluripotent stem cell is derived from a T cell that does not express a rearranged T-cell receptor (TCR).

The present invention provides a method of producing a pluripotent stem cell bearing a rearranged T-cell receptor (TCR) locus and expressing a chimeric antigen receptor (CAR). In one non-limiting embodiment, said method comprises a) providing, i) a pluripotent stem cell bearing a rearranged TCR locus (T-PSCs), and ii) a CAR expression vector encoding an antigen binding domain and a CD3ζ polypeptide, and b) transducing said cell with said CAR expression vector under conditions such that a CAR-expressing T-PSC (CAR-T-PSC) is produced. In certain embodiments, said CAR expression vector comprises a heterologous gene encoding at least one costimulatory signaling region or a costimulatory ligand. Said at least one costimulatory ligand can be selected from the group consisting of CD80, CD86, CD70, OX40L, 4-1BBL, CD48, TNFRSF14, and PD-L1. Said costimulatory signaling region can comprise a CD28 polypeptide, a 4-1BB polypeptide, an OX40 polypeptide, an ICOS polypeptide, or a PD-1 polypeptide, a LAG-3 polypeptide, a 2B4 polypeptide, a BTLA polypeptide, or a CTLA-4 polypeptide. In certain embodiments, the pluripotent stem cell is an embryonic stem cell or an induced pluripotent stem cell. In one embodiment, the pluripotent stem cell is an induced pluripotent stem cell.

The present invention provides a method of producing a T cell. In one non-limiting embodiment, said method comprises a) providing, i) a pluripotent stem cell bearing a rearranged T-cell receptor (TCR) locus (T-PSCs), and ii) a chimeric antigen receptor (CAR) expression vector encoding an antigen binding domain and a CD3ζ polypeptide, b) transducing said T-PSC with said CAR expression vector under conditions such that a CAR-expressing T-PSC (CAR-T-PSC) is produced; and c) culturing said CAR-T-PSC under conditions such that a CAR-T-PSC-derived T cell is produced. In certain embodiments, said c) culturing said CAR-T-PSC under conditions such that a CAR-T-PSC-derived T cell is produced comprises: (a) providing, i) said CAR-T-PSC, ii) a first cell culture medium for mesoderm induction, iii) a second cell culture medium for hematopoietic specification and expansion, iii) a third cell culture medium for T-lymphoid differentiation, and iv) a feeder cell line that induces T lymphoid commitment in hematopoietic cells, and (b) incubating said CAR-T-PSC with said first cell culture medium for up to about 4 days under conditions such that a mesoderm cell is produced, (c) incubating said mesoderm cell with said second cell culture medium for up to about 6 days under conditions such that a hematopoietic cell is produced and expanded, (d) incubating said expanded hematopoietic cell and said feeder cell line with said third cell culture medium for at least about 5 days for inducing T lymphoid commitment in said expanded hematopoietic cell to produce a CAR-T-PSC-derived T cell. In certain embodiments, the pluripotent stem cell is an embryonic stem cell or an induced pluripotent stem cell. In one embodiment, the pluripotent stem cell is an induced pluripotent stem cell. In certain embodiments, said T cell expresses the CAR. In some embodiments, said T cell targets specifically to one antigen and antigen specificity of said T cell is HLA-independent. In one embodiment, the first cell culture medium comprises bone morphogenetic protein 4 (BMP-4) and basic fibroblast growth factor (bFGF). In one embodiment, the second cell culture medium comprises Vascular endothelial growth factor (VEGF), bFGF, stem cell factor (SCF), FMS Like Tyrosine Kinase 3 Ligand (Flt3L), and at least one Th1 cytokine, which can be selected from the group consisting of Interleukin-3 (IL-3), IL-15, IL-7, IL-12 and IL-21. In one embodiment, the third cell culture medium comprises SCF, Flt3L, and at least one Th1 cytokine, which can be selected from the group consisting of IL-15, IL-7, IL-12 and IL-21. In certain embodiments, said method further comprises d) exposing said CAR-T-PSC-derived T cell to an antigen-presenting cell under conditions for stimulating an activity of said CAR-T-PSC-derived T cell. In one embodiment, said activity is selected from the group consisting of cytokine secretion, cell division, cytotoxicity, cytostatic inhibition, and inhibition of cell growth. In one embodiment, said cytokine is a Th1 cytokine selected from the group consisting of IFN-γ, IL-2 and TNF-α. In one embodiment, said cytotoxicity is determined by killing a target cell expressing an antigen that binds to said CAR and measuring target cell death. In one embodiment, said inhibition of cell growth comprises inhibition of growth of a tumor cell. In one embodiment, said inhibition of cell growth comprises reduction in tumor size. Said CAR can comprise an antigen binding domain. In one embodiment, said antigen binding domain of said is specific for an antigen. Said antigen can be a tumor antigen or a pathogen antigen. In certain embodiments, said antigen is selected from the group consisting of carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, an antigen of a cytomegalovirus (CMV) infected cell (e.g., a cell surface antigen), epithelial glycoprotein2 (EGP 2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), melanoma antigen family A, 1 (MAGE-AI), Mucin 16 (Muc-16), Mucin 1 (Muc-1), Mesothelin (MSLN), NKG2D ligands, cancer-testis antigen NY-ESO-1, oncofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), and Wilms tumor protein (WT-1). In one embodiment, said CAR expression vector comprises a nucleic acid sequence that is integrated into said CAR-T-PSC's genome at a genomic safe harbor site. In one embodiment, said CAR expression vector further encodes a fluorescent protein for expressing in said CAR-T-PSC. In one embodiment, said fluorescent protein is mCherry. In one embodiment, said method further comprises e) inducing florescence in said CAR-T-PSC for tracking said CAR-T-PSC. In one embodiment, said method further comprises f) tracking said CAR-T-PSC in vitro. In one embodiment, said method further comprises g) tracking said CAR-T-PSC in vivo.

The present invention provides a method of producing a pluripotent stem cell. In one non-limiting embodiment, said method comprises a) providing, i) a cell selected from the group consisting of an isolated peripheral blood lymphocyte (PBL) and an isolated peripheral blood T-cell, and a combination thereof, and ii) at least one retroviral vector encoding at least one reprogramming factor selected from the group consisting of octamer-binding transcription factor 4 (OCT4), Kruppel-like factor 4 (KLF4), myelocytomatosis viral oncogene homolog (c-MYC), and transcription factor SOX-2, and b) transducing said cell with said at least one retroviral vector under conditions for producing a pluripotent stem cell. In certain embodiments, said pluripotent stem cell is an embryonic stem cell or an induced pluripotent stem cell. In one embodiment, said pluripotent stem cell is an induced pluripotent stem cell. In one embodiment, said retroviral vector encodes in 5' to 3' direction OCT4 and KLF4. In another embodiment, said retroviral vector encodes in 5' to 3' direction c-MYC and SOX-2. In some embodiments, said retroviral vector is excisable. In some embodiments, said retroviral vector comprises a loxP site located in the 3' long terminal repeat (LTR) for use by Cre recombinase for excising said at least one reprogramming factor. In certain embodiments, said retroviral vector further encodes a fluorescent marker e. In one embodiment, said fluorescent marker is green fluorescent protein. In another embodiment, the fluorescent marker is Citrine. A pluripotent stem cell and a cell population comprising thereof produced by the above-described method are also provided in the present invention.

The present invention provides an excisable retroviral vector encoding in 5' to 3' direction, at least one reprogramming factor selected from the group consisting of octamer-binding transcription factor 4 (OCT4), Kruppel-like factor 4 (KLF4), myelocytomatosis viral oncogene homolog (c-MYC), and transcription factor SOX-2. In certain embodiments, the retroviral vector encodes two reprogramming factors. In some embodiments, the retroviral vector encodes in 5' to 3' direction OCT4 and KLF4. In some embodiments, the retroviral vector encoding in 5' to 3' direction cMYC and SOX2. In certain embodiments, said retroviral vector further encodes a fluorescent marker. In one embodiment, the fluorescent marker is Citrine. In one embodiment, the fluorescent marker is GFP. In certain embodiments, the retroviral vector comprises a loxP site in the 3' long terminal repeat (LTR) for use by Cre recombinase for excising said at least one reprogramming factor. In some embodiments, said retroviral vector further comprises a promoter in operable combination with a nucleic acid sequence encoding said at least one reprogramming factor.

The present invention provides a pluripotent stem cell that expresses a chimeric antigen receptor (CAR). In certain embodiments, the pluripotent stem cell is an embryonic stem cell or an induced pluripotent stem cell. In one embodiment, the pluripotent stem cell is an induced pluripotent stem cell. The present invention also provides a cell population comprising the above-described pluripotent stem cell.

In a related aspect, the present invention provides a pharmaceutical composition containing an effective amount of a cell population of T cells of any aspect of the present invention delineated herein in a pharmaceutically acceptable excipient. In another related aspect, the invention provides a pharmaceutical composition for the treatment of a neoplasia containing an effective amount of tumor antigen-specific T cells of any aspect of the invention delineated herein in a pharmaceutically acceptable excipient.

In an additional aspect, the invention provides a kit for treatment of a neoplasia, pathogen infection, an autoimmune disorder, or an allogeneic transplant, the kit comprising a cell population comprising T cells that are generated from induced pluripotent stem cells (iPSCs), wherein said T cells target specifically to one antigen, and antigen recognition by said T cells is HLA-independent. In certain embodiments, the kit further comprises written instructions for using the cell for the treatment of a subject having a neoplasia, a pathogen infection, an autoimmune disorder, or an allogeneic transplant.

DEFINITIONS

To facilitate understanding of the present invention, a number of terms are defined below.

As used herein, "a" or "an" means "at least one" or "one or more."

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells expressing similar or different phenotypes.

As used herein, the term "clone" in reference to a cell clone refers to a cell that is genetically identical to another cell, for example T cell clones are daughter cells genetically identical to the parental cell.

As used herein, the term "peripheral blood lymphocyte(s)" or "PBL(s)" refers to white blood cell(s) comprising T cells and B cells of a range of differentiation and functional stages, plasma cells, monocytes, macrophages, natural killer cells, basocytes, eosinophyils, etc.

As used herein, the term "isolated" in reference to a population refers to the removal of a smaller desired cell population from a larger starting population. As one example, isolated peripheral blood lymphocytes may refer to a specific white blood cell layer located in a gradient of Ficol. As another example, "isolated peripheral blood T-cells" may refer to a population of $CD3^+$ cells isolated from a larger white blood cell population, as one example, $CD3^+$ cells may be isolated using anti $CD3^+$ antibodies, such as by flow cytometry sorting or magnetic bead separation, etc. As one example, a $CD3^+$ T cell population may be isolated from peripheral blood mononuclear cells (PBMCs)

or other cell population by magnetic separation using CD3 antibody directly or indirectly attached to magnetic particles.

As used herein, the term "pluripotent" refers to a cell line capable of differentiating into multiple differentiated cell types.

As used herein, the term "pluripotent stem cell (PSC)" or "pluripotent stem cells (PSCs)" refers to stem cell(s) that have the potential to differentiate into any of the three germ layers: endoderm (interior stomach lining, gastrointestinal tract, the lungs), mesoderm (muscle, bone, blood, urogenital), or ectoderm (epidermal tissues and nervous system). In non-limiting examples, a PSC can be an embryonic stem cell or an induced pluripotent stem cell.

As used herein, the term "multipotent" refers to a cell line capable of differentiating into at least two differentiated cell types.

As used herein, the term "embryonic stem cell (ESC)" or "embryonic stem cells (ESCs)" refers to a pluripotent stem cell derived from the inner cell mass of a blastocyst.

As used herein, the term "adult stem cell" or "adult stem cells" refers to stem cell(s) derived from an organism after birth.

As used herein, the term "T lymphocyte" or "T cell" refers to a cell expressing CD3 ($CD3^+$) and a T Cell Receptor ($TCR^+$).

As used herein, the term "TCR" or "T cell receptor" refers to a dimeric heterologous cell surface signaling protein forming an alpha-beta or gamma-delta receptor typically involved in recognizing an antigen presented by an MHC molecule (i.e. antigen recognition in the context of an MHC molecule).

As used herein, the term "CD3 complex" refers to a cell surface molecule assembly comprising numerous proteins for transmembrane signaling of TCR activation.

As used herein, the terms "region" or "portion" when used in reference to a nucleic acid molecule refers to a set of linked nucleotides that is less than the entire length of the molecule, such as a CD3ζ signaling region described herein.

As used herein, the term "cell culture system" refers to compositions and methods of culturing cells to produce a more specific homogenous cell type. A cell culture system can comprise certain cell culture factors in cell growth medium, and methods of incubation for a time period for culturing cells in specific culture factors for producing specific cells. In one non-limiting example, a cell culture system can provide compositions and methods for producing cells of a non-default cell type, such as producing more differentiated T cells with a specific antigen recognition. In another non-limiting example, a cell culture system can be used for dedifferentiating T cells for producing induced pluripotent T cells.

As used herein, the term "precursor T cell" in reference to a cell produced by compositions and methods of the present inventions refers to a cell expressing CD34 ($CD34^+$) and $CD7^-$ ($CD7^-$).

As used herein, the term "induced pluripotent stem cell(s)" or "iPSC(s)" refers to pluripotent stem cell(s) artificially derived in vitro from a somatic cell through forced expression (transformed or induced) of specific reprogramming transcription factors (such as, OCT-4, KLF-4, SOX-2, c-Myc). iPSCs are similar to embryonic stem cells in morphology, stem cell gene expression pattern, chromatin methylation pattern and pluripotency (teratoma formation, embryoid body formation, etc.).

As used herein, the term "T-PSC" or "T-PSCs" refers to pluripotent stem cell(s) bearing a rearranged TCR locus, such that a T cell is reprogrammed or dedifferentiated to a pluripotent stem cell (PSC). A T-PSC cell may derive from any isolated endogenously developed mature T cell.

As used herein, the term "T-iPSC" or "T-iPSCs" refers to induced pluripotent stem cell(s) bearing a rearranged TCR locus, such that a T cell is reprogrammed or dedifferentiated to an iPSC. A T-iPSC cell may derive from any isolated endogenously developed mature T cell.

As used herein, the term "CAR-T-PSC" or "CAR-T-PSCs" refers to pluripotent stem cell(s) bearing a pre-rearranged TCR locus and expressing a chimeric antigen receptor (CAR) ($CAR^+$). The CAR-T-PSC does not express a TCR on the cell surface. There typically is expression of the TCR after re-differentiation using a cell culture method for producing committed T cells and effector T cells. CAR-T-PSC can be produced by transducing T-PSC with a CAR vector.

As used herein, the term "CAR-T-iPSC" or "CAR-T-iPSCs" refers to induced pluripotent stem cell(s) bearing a pre-rearranged TCR locus and expressing a chimeric antigen receptor (CAR) ($CAR^+$). The CAR-T-iPSC does not express a TCR on the cell surface. There typically is expression of the TCR after re-differentiation using a cell culture method for producing committed T cells and effector T cells. CAR-T-iPSCs can be produced by transducing T-iPSC with a CAR vector.

As used herein, the term "CAR-T-PSC-derived T cell(s)" refers to T cell(s) produced or derived from CAR-T-PSC(s) as described above. For example, CAR-T-PSC-derived T cell can be derived from CAR-T-PSC after induction of differentiation using a cell culture system of the present invention. CAR-T-PSC-derived T cell can recognize an antigen, for which the CAR is specific or which can be recognized by the CAR.

As used herein, the term "CAR-T-iPSC-derived T cell(s)" refers to T cell(s) produced or derived from CAR-T-iPSC(s) as described above. For example, CAR-T-iPSC-derived T cells can be derived from CAR-T-iPSCs after induction of differentiation using a cell culture system of the present invention. CAR-T-iPSC-derived T cells can recognize an antigen, for which the CAR is specific or which can be recognized by the CAR.

As used herein, the term "CAR-T-PSC-derived T cell(s)" refers to T cell(s) produced or derived from CAR-T-PSC(s) as described above. For example, CAR-T-PSC-derived T cell can be derived from CAR-T-PSC after induction of differentiation using a cell culture system of the present invention. CAR-T-PSC-derived T cell can recognize an antigen, for which the CAR is specific or which can be recognized by the CAR.

As used herein, the term "CAR-T-PSC effector T cell(s)" refers to effector T cell(s) produced from CAR-T-PSC(s) as described above, e.g., CAR-T-PSC-derived T cells. CAR-T-PSC effector T cells can possess at least one of the following activities: cytokine secretion (including, but not limited to, IL-2, IFN-γ, TNF-α), proliferation when exposing an antigen that can be recognized by the CAR, cytoxicity, and cytostatic inhibition.

As used herein, the term "CAR-T-iPSC effector T cell(s)" refers to effector T cell(s) produced from CAR-T-iPSC(s), e.g., CAR-T-iPSC-derived T cells. CAR-T-iPSC effector T cells can possess at least one of the following activities: cytokine secretion (including, but not limited to, IL-2, IFN-γ, TNF-α), proliferation when exposing an antigen that can be recognized by the CAR, cytoxicity, and cytostatic inhibition.

As used herein, the term "cytotoxic" or "cytostatic" or "cytostatic inhibition" refers to one or more of an inhibition of tumor growth and a reduction in tumor load, i.e. the amount of tumor cells in a subject, such as measured by diagnostic means.

As used herein, the term "contacting" or "exposing" in reference to an antigen and its binding region on a CAR refers to the interaction between the antigen binding region expressed by a CAR and its antigen that stimulates a response in a $CAR^+$ cell.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::VL heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10: 31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')$_2$" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

As used herein, the term "Cluster of Differentiation" or "CD" refers to a cell surface marker, e.g., a leukocyte. CD can be used to distinguish cell lineages, developmental stages, and functional subsets. The CAR of the present invention can target to a CD, including, but not limited to, CD10, CD19, etc.

As used herein, the term "selectable marker" refers to the use of a gene that encodes a protein which delivers a distinguishable activity to the cell such as the ability to grow in medium containing an antibiotic that would otherwise kill a cell (e.g. a neomycin phosphoryltransferase (Neo) gene in transformed or transduced cells) or the ability to emit fluorescent light. For one example, a selectable marker may confer resistance to an antibiotic or drug upon the cell, such as when a selectable marker, such as a neomycin phosphoryltransferase (Neo) gene, is expressed. Another type of marker is a fluorescent marker, such as enhanced GFP (eGFP), mCherry, etc., which can be detected by flow cytometry or fluorescence microscopy. Fluorescent markers include green fluorescent protein, blue fluorescent protein, cyan fluorescent protein, and yellow fluorescent protein. Blue fluorescent proteins include EBFP, EBFP2, Azurite, and mKalama1. Cyan fluorescent proteins include ECFP, Cerulean, and CyPet. Yellow fluorescent proteins include YFP, Citrine, Venus, and YPet.

As used herein, the term "differentiation" as used with respect to cells in a differentiating cell system refers to a process by which cells differentiate from one cell type (e.g., a multipotent, totipotent or pluripotent differentiable cell) to another cell type such as a target differentiated cell (e.g., a T cell). As such, differentiation may be by default or a nondefault cell type. In vitro, a default cell type is the majority cell type in a cell population when not exposed to a certain differentiation factor or group of factors in contrast to a non-default cell type or different cell type in the majority of cells when exposed to certain differentiation factor(s).

As used herein, "inducing hematopoietic differentiation" in reference to a cell culture system refers to compositions and methods of the present inventions as described herein, for producing $CD34^+$ hematopoietic precursor cells from T-iPSCs, see Example I for an exemplary description.

As used herein, "reprogramming" in reference to a cell culture system refers to compositions and methods for producing T-PSC cells from peripheral blood mature T lymphocytes of the present inventions as described herein, wherein said reprogrammed cells initially express reprogramming transcription factors (consisting of Oct-4, KLF-4, Sox-2 and c-Myc), see Example I for an exemplary description.

As used herein, "re-differentiate" or "T lymphoid differentiation" or "T lymphoid commitment" in reference to a cell culture system refers to compositions and methods described herein, for producing cells with T lymphoid specific markers that were expressed but then silenced during reprogramming (CD7, CD5, CD3, TCR) from T-PSC-derived $CD34^+$ cells. In particular, T cells of the present inventions were produced by compositions and methods of a re-differentiation or cell culture system as describe in Example I.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including stem cells, embryonic cord blood cells, transduced cells, etc.

As used herein, "Embryoid body" or "EB" refers to three-dimensional aggregates of pluripotent stem cells that form during certain cell culture systems.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

The term "expression vector" as used herein refers to a recombinant nucleic acid sequence, i.e. recombinant DNA molecule, containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "Lentivirus" refers to a virus that can transduce both actively proliferating and non-dividing cells.

As used herein, the term "SFG vectors" refer to gammaretroviral vectors which also find use in the present inventions, such vectors include but are not limited to vectors derived from the Moloney murine leukemia virus, including vectors and vector construction described, for examples, by Riviere, PNAS, 1995, Gallardo, Blood, 1997, herein incorporated by reference in their entirety.

As used herein, the term "excisable" in reference to a vector refers to a vector that can be removed from a genome after integration (transduction), wherein said vector has a loxP site in a 3'LTR for use by Cre recombinase for excising the vector sequences.

As used herein, the term "lentiviral" or "lentivirus" in reference to a vector refers to viral vectors derived from the Lentiviridae family that are capable of integrating into dividing and non-dividing cells, including but not limited to pLM vectors, (For examples, see, e.g., Papapetrou & Sadelain, Nature Protocols, 6(9):1274-1289 (2011); U.S. Pat. Nos. 5,994,136 and 6,013,516, all of which are incorporated herein by reference). A variety of lentiviral vectors and packaging cell lines are known in the art and find use in the present invention (See, e.g., U.S. Pat. Nos. 5,994,136 and 6,013,516, both of which are herein incorporated in their entirety by reference) however it is not meant to limit the type of vector so long as it is capable of stably integrating a CAR into the genome of a cell.

The term "transduction" as used herein refers to the process where heterologous nucleic acid sequences are introduced into another cell using a viral vector.

The term "transfection" as used herein refers to the process of introducing nucleic acids into cells by non-viral methods. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, and biolistics.

The term "stable transduction" or "stably transduced" refers to a cell that has stably integrated the foreign DNA into the genome after infection with a viral vector.

The term "silenced" in reference to a gene or protein refers to the downregulation or absence of gene expression and/or protein expression. The term "silenced" in reference to a cell having a silenced gene refers to a cell that has at least one downregulated or absent gene as compared to an equivalent cell that does not have the silenced gene.

As used herein, "adoptive cell transfer therapy" or "ACT" refers to administration of ex vivo-activated and -expanded autologous tumor-reactive T lymphocytes.

As used herein, "autologous" refers to genetically identical cells derived from the same donor.

As used herein, "allogeneic" refers to cells derived from a genetically non-identical donor. Allogeneic cells typically cause graft-host disease when used for cell or organ transplantation.

As used herein, "MHC" or "major histocompatibility complex" refers to cell surface molecules encoded by a large number of genes in mammals. MHC molecules include Class I and Class II. Class I molecules are alternatively referred to in humans as "HLA" or "human leukocyte antigen." In part due to the complexity of HLA molecule expression HLA may also be referred to as an HLA system. Humans express HLA-A, HLA-B and HLA-C molecules that are typically involved with presenting processed antigen to CD8 cells, i.e. HLA restricted. Class II molecules, such as DR, DQ, DP, etc., are typically involved with presenting externally derived peptides to CD4+ cells, i.e. MHC Class II restricted. MHC restricted in general encompasses both Class I and Class II as in transplantation (bone marrow) matching.

As used herein, "HLA-restricted" or "MHC-restricted" refers to antigen recognition requiring both MHC molecule and it's peptide. Unlike antigen recognition that is "not HLA-restricted" or "HLA-independent" or "not MHC-restricted."

As used herein, the term "in vitro" refers to an artificial environment and to processes or reactions that occur within an artificial environment. In vitro environments can consist of, but are not limited to, test tubes and cell culture. Alternatively, the term "in vivo" refers to the natural environment (e.g., an animal or a cell) and to processes or reaction that occur within a natural environment.

As used herein, the term "subject" refers to any animal (e.g., a mammal), including, but not limited to, humans, non-human primates, rodents, and the like (e.g., which is to be the recipient of a particular treatment, or from whom cells are harvested).

As used herein, the term "effective amount" refers to an amount sufficient to have a therapeutic effect. In one embodiment, an "effective amount" is an amount sufficient to arrest, ameliorate, or inhibit the continued proliferation, growth, or metastasis (e.g., invasion, or migration) of a neoplasia. An effective amount can be administered in one or more administrations, applications or dosages and is not intended to be limited to a particular formulation or administration route.

As used herein, the term "therapeutically effective amount" refers to an amount sufficient to reduce by a least about 15 percent, preferably by at least 50 percent, more preferably by at least 90 percent, and most preferably prevents a clinically significant harmful effect or activity or response of disease causing cells in a host patient, such as a reduction in tumor load or cancer, or at least slowing or stopping the development of additional tumor growth or spread of cancer. Alternatively, a therapeutically effective amount is sufficient to cause an improvement in a clinically significant condition in a host patient, i.e. such as when a CAR+ cell of the present inventions is administered to a patient having cancer and cancer cells are killed.

As used herein, the term "treatment" or "treating" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests. The subject may be in need of anticancer adoptive immunotherapy comprising the T cells of the present invention.

As used herein, the term "administered" or "administering" refers to any method of providing a composition (i.e., for example, a biological cell) to a patient such that the composition has its intended effect on the patient. For example, one method of administering is by an indirect mechanism using a medical device such as, but not limited to a catheter, applicator gun, syringe etc. A second exemplary method of administering is by a direct mechanism such as, local tissue administration (i.e., for example, extravascular placement), oral ingestion, transdermal patch, topical, inhalation, suppository, etc, however it is not meant to limit the type of administering a cell produced by methods of the present inventions to a patient.

As used herein, the term "cancer cells" or "cancerous cells" refers to individual cells of a cancer. Such cells may include, for example, tumorigenic cells (e.g., capable of generating a tumor), leukemogenic cells (e.g., capable of generating leukemia), cancer stem cells (e.g., capable of forming new tumors or transferring disease upon transplantation into an immunocompromised host), as well as cells that are not tumorigenic, leukemogenic or that are capable of forming new tumors or transferring disease upon transplantation (e.g., mesenchymal and endothelial cells) including but not limited to prostate cancer, breast cancer, etc.

As used herein, the term "nucleic acid molecule" refers to any nucleic acid containing molecule, including but not limited to, DNA or RNA. The term encompasses sequences that include any of the known base analogs of DNA and RNA As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). As another example, a heterologous gene includes a gene expressed in a previous or future cell lineage or differentiation state of a cell. Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, "amino acid sequence" and terms such as "polypeptide" or "protein" are not meant to limit the amino acid sequence to the complete, native amino acid sequence associated with the recited protein molecule.

As used herein, the term "substantially identical" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

As used herein, the term "ligand" refers to a molecule that binds to a receptor. In particular, the ligand binds a receptor on another cell, allowing for cell-to-cell recognition and/or interaction.

As used herein, the term "neoplasia" is meant a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells).

As used herein, the term "pathogen" is meant a virus, bacteria, fungi, parasite or protozoa capable of causing disease.

Exemplary viruses include, but are not limited to, Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Caliciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Naira viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2 parenterally transmitted (i.e. Hepatitis C); Norwalk and related viruses, and astroviruses).

Exemplary bacteria include, but are not limited to, *Pasteurella, Staphylococci, Streptococcus, Escherichia coli, Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelli*.

As used herein, the term "receptor" refers to a polypeptide, or portion thereof, present on a cell membrane that selectively binds one or more ligand.

As used herein, the term "reduce" is meant to alter negatively by at least 5%. An alteration may be by 5%, 10%, 25%, 30%, 50%, 75%, or even by 100%.

As used herein, the term "recognize" refers to selectively binds a target. A T cell that recognizes a virus typically expresses a receptor that binds an antigen expressed by the virus.

As used herein, the term "tumor antigen" refers to an antigen (e.g., a polypeptide) that is uniquely or differentially expressed on a tumor cell compared to a normal or non-IS neoplastic cell. With reference to the invention, a tumor antigen includes any polypeptide expressed by a tumor that is capable of activating or inducing an immune response via an antigen recognizing receptor (e.g., CD19, MUCI) or capable of suppressing an immune response via receptor-ligand binding (e.g., CD47, PD-L1/L2, B7.1/2).

As used herein, the term "virus antigen" refers to a polypeptide expressed by a virus that is capable of inducing an immune response.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

Other aspects of the present invention are described in the following disclosure and are within the ambit of the present invention.

BRIEF DESCRIPTION OF THE DRAWINGS

The following Detailed Description, given by way of example, but not intended to limit the present invention to specific embodiments described, may be understood in conjunction with the accompanying drawings.

FIGS. 4A-4G show generation of T-iPSCs. (A) Schematic representation of the two tricistronic retroviral vectors used for reprogramming peripheral blood T lymphocytes (PBL). Each of the vectors encodes 2 of the Yamanaka's reprogramming factors and a fluorescent marker (vexGFP or mCitrine) linked with 2A peptides. LTR: long terminal repeat, wpre: woodchuck hepatitis virus posttranscriptional regulatory element. (B) Reprogramming vector copy number in different T-iPSC lines assessed by qPCR. (C) Silencing of reprogramming vectors in T-iPSCs assessed by qRT-PCR. Expression of the vector-encoded transcripts vexGFP-P2A-Oct4-E2A-KLF4 and mCitrine-P2A-cMyc-T2A-SOX2 in PBL before transduction (PBL d0), 3 days post-transduction (PBL d3) and in 3 different T-iPSC clones. (D) Expression of pluripotent cell markers Tra-1-81, Tra-1-60, SSEA-3 and SSEA-4 in clone T-iPSC-1.10 assessed by flow cytometry. The pluripotency marker-negative/HLA-ABC-negative population corresponds to MEFs. (E) Expression of endogenous pluripotency-associated genes in clone TiPSC-1.10 (listed below the X axis) assessed by qRT-PCR. Data were normalized to the values of endogenous GAPDH and are shown as relative expression against the expression levels of PBL d0. hES: human embryonic stem cell line HI. (F) Karyotypic analysis of clone TiPSC-1.10. (G) Representative hematoxylin and eosin staining of histological sections of a teratoma derived from clone T-iPSC-1.10 comprising tissues of all three germ layers. Black arrows show ectoderm: neuronal rosettes, mesoderm: cartilage and mesoderm: gland-like epithelium.

FIGS. 7A and 7B show generation of hematopoietic progenitors with lymphoid potential. a) Expression of Notch1 and GATA-3 in isolated CD34+ cells from day 10 and day 12 of differentiation of clone T-iPSC-1.10, assessed by qRT-PCR using Taqman Gene Expression Assays (Applied Biosystems). Data were normalized to the values of endogenous GAPDH and are shown as relative expression against the expression levels of clone T-iPSC-1.10. b) Flow cytometric analysis of Notch1 and CD127 (IL-7Rα) expression in the CD34+CD43− hematopoietic progenitors and CD34−CD43− cells at day 10 of differentiation of clone T-iPSC-1.10. Representative plots of at least 5 independent differentiations.

FIGS. 8A-8C show expression of surface markers and receptors on 1928z-T-cells. (A) Expression of TCRγδ and CD3 by flow cytometry. (B) Expression of NK cell-specific surface markers and receptors was assessed by flow cytometry on 1928z-T-iPSC-T cells before (pre-expansion) and 7 days after (post-expansion) stimulation with irradiated 3T3-CD19 cells. (C) Expression of CD27 and CD28 on 1928z-T-iPSC-T cells before and 7 days after stimulation with irradiated 3T3-CD19 cells.

DESCRIPTION OF THE INVENTION

Figure 1A:
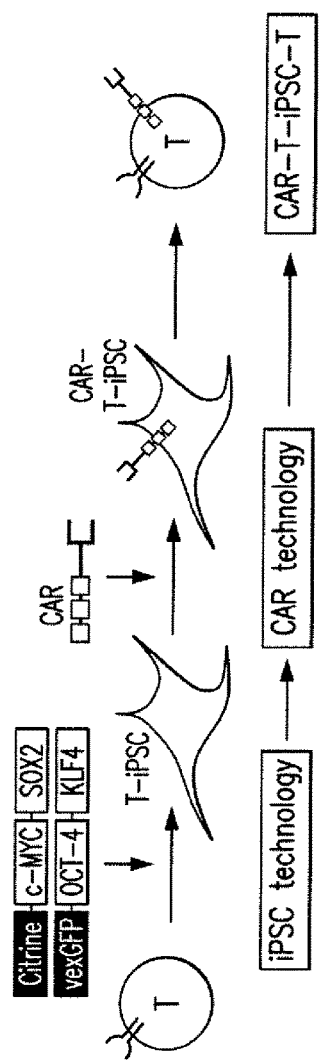
FIGS. 1A-1F show differentiation of 1928z CAR-engineered T-iPSCs into CD19-specific functional T lymphocytes. (A) The study concept. Peripheral blood lymphocytes are reprogrammed to pluripotency by transduction with retroviruses encoding c-MYC, SOX2, KLF4 and OCT-4 (7). The resulting T-iPSCs are genetically engineered to express a CAR and are then differentiated into T cells that express both the CAR and an endogenous TCR. (B) In vitro T-lymphoid differentiation protocol. T-iPSCs were stably transduced with a bicistronic lentiviral vector encoding the 19-28z CAR and the fluorescent marker mCherry. mCherry+ CAR+T-iPSCs are differentiated in three steps: (i) mesoderm formation (days 1-4), (ii) hematopoietic specification and expansion (days 5-10) and (iii) T-lymphoid commitment (days 10-30). Fluorescence microscopy images (below) show mCherry expression was maintained throughout the differentiation process. Scale bars, 100 µM. (C) Flow cytometric analysis of 1928z-T-iPSC-derived cells at day 30 of differentiation. Representative plots are of at least five independent differentiations. (D) 1928z-T-iPSC-T cells were seeded into cultures of 3T3 cells or 3T3 cells expressing CD19 (3T3-CD19). Co-cultures shown 24 h after T-cell seeding; formation of T-cell clusters and elimination of the 3T3-CD19 monolayer are visible. Scale bars, 100 mM. (E) Flow cytometric analysis of CD25 and CD69 expression on the surface of 1928z-T-iPSC-T cells 48 h after exposure to 3T3 or 3T3-CD19 cells. (F) Luminex multiplex cytokine analysis of culture supernatant 24 h after seeding of 1928z-T-iPSC-T cells on 3T3 or 3T3-CD19 cells. Data are presented as mean of two independent experiments±s.d.

The present invention relates to the field of adoptive immunotherapy. The present invention provides phenotypically defined, functional, and/or expandable T cells that possess at least one of the following immunotherapeutic features: 1) targeting a specific predetermined antigen expressed on the cell surface of a target cell in an HLA independent manner, 2) enhanced survival and functional potential and 3) available "off-the-shelf" T cells for administration to multiple recipients, eventually across immunogenic barriers, and 4) cytotoxic potential and anti-tumor activity.

In summary, although there are numerous examples of publications describing the generation of antigen-specific T cells or NK cells from human ESCs and iPSCs, none of these examples of publications describe the production and use of an iPSC or ESC expressing a CAR (including an antigen recognition region (domain), a CD3z chain, and optionally at least one costimulatory signal provided either within in the CAR protein or as a costimulatory ligand protein co-expressed with a CAR protein, i.e. to provides at least two proteins with extracellular binding sites, the CAR protein and the costimulatory ligand protein) as an in vitro determined antigen-specificity that is further differentiated then expanded by using CAR stimulation for use as described herein. The present invention relates to engineering antigen-specificity through the use of vectors comprising CARs transduced into T-iPSCs or NK cells produced by compositions and methods the present invention.

The present invention also provides methods for generating phenotypically defined, functional, and/or expandable T cells from human T-iPSCs engineered through safe genetic modifications, e.g., iPSCs that are modified to express a chimeric antigen receptor (CAR) (CAR-T-iPSCs). The CAR-T-iPSCs can be further differentiated and expanded in cell numbers using a CAR binding antigen for stimulation (instead of through TCR activation or non-specific activation) of the CAR$^+$ cell for producing CAR-T-iPSC-derived T cells (CAR-T-iPSC-T cells) having effector activity (function) in numbers contemplated for therapeutically effective adoptive cell therapy, e.g., CAR-T-iPSC-derived effector T cells.

The present invention provides antigen-specific T lymphocytes for immunotherapy including but not limited to antigen-specific T lymphocytes capable of removing established tumor cells in vivo. In accordance with the present invention, the antigen-specific T lymphocytes can reduce the growth of cancerous cells. In some embodiments, the antigen-specific T lymphocytes can kill virus infected cells, including but not limited to HIV infected cells in vivo.

Currently, use of T cells that express an endogenous antigen-specific TCR (or other antigen presenting molecule) in adoptive immunotherapy relies upon MHC-dependent self-recognition and antigen (i.e. in the context of antigen) for stimulation. This MHC matching requirement along with antigen-specific binding results in limitations of effector function when a tumor (cancer) cell escapes immunoregulation when expression of its MHC molecules containing antigen is reduced or absent, i.e. one example of a tumor escape mechanism. Therefore, use of CAR$^+$ cells of the present inventions can overcome such tumor escape because CAR based antigen recognition does not depend upon MHC recognition, merely the capability of an extracellular expressed antigen to bind to the CAR.

Further, use of T cells and other effector cells that express endogenous MHC molecules in adoptive immunotherapy limits such cells for immunotherapy to autologous use, i.e. subject to the limitations of MHC haplotypes matching as does tissue transplantation. In certain embodiments, the CAR$^+$ cells of the present invention have reduced or undetectable cell surface expression of MHC molecules. In certain embodiments, the CAR$^+$ cells of the present invention have reduced or undetectable cell surface expression of HLA molecules. In some embodiments, the CAR$^+$ cells of the present invention have reduced or undetectable cell surface expression of HLA class I molecules.

The antigen-specific T lymphocytes of the present invention express CAR, and target specifically to one antigen through the interaction between CAR and the antigen. The CAR of the present invention can provide antigen-specific stimulation to the T lymphocytes expressing the CAR, which results in cell proliferation and/or an effector function. The CAR-expressing T cells of the present invention can overcome the limitations of T cells having an endogenous antigen-specific TCR, which have limited proliferative and functional capability in vivo even if an antigen-specific T cell present in vivo and then happens to be present in isolated PBMCs. The CAR-expressing T cells of the present invention have long term survival rates (increased proliferative capability) both in vitro and in vivo for providing therapeutically relevant numbers of antigen-specific cells for both short term and long term adoptive cell therapies. This is unlike the shorter term (fewer cycles of proliferation) when mature (endogenously isolated) source effector cells are used for in vitro expansion methods. Cells having shorter term survival rates result in antigen "exhaustion" when they have reduced or non-existent proliferation in vitro. The present invention provides methods for producing therapeutically relevant (effective) numbers of antigen-specific T cells from small amounts of isolated blood cells isolated from one sample of blood cells drawn from a subject. In some embodiments, the amount of the blood sample drawn from a patient is at least about 0.5 mls, at least about 1 ml, at least about 5 mls, or up to about 10 mls of blood, in contrast to collecting multiple tubes of blood from the subject. In some embodiments, the methods for producing antigen-specific CAR$^+$ T cells of the present invention comprise producing up to about $10^8$, up to about $10^9$, up to about $10^{10}$, up to about $10^{11}$, up to about $10^{12}$, or greater than $10^{12}$ antigen-specific CAR$^+$ T cells from one subject. The present invention provides dedifferentiation (reprogramming) of peripheral blood T cells to T-PSCs (ESCs or iPSCs) for use with engineered vector constructs comprising a chimeric antigen-specific regions CAR to produce CAR-expressing T-PSCs. Furthermore, the present invention provides methods of producing CAR-expressing T cells from CAR-expressing or CAR-modified PSCs (e.g., ESCs or iPSCs). In some embodiments, the methods comprises providing a differentiation cell culture system for producing CAR-PSC-T-derived T effector cells from CAR-T-PSCs. The produced CAR-PSC-T-derived T effector cells can be used immunotherapy treatments.

In certain embodiments, the present invention includes providing genetic modifications to T cells. The genetically modified (engineered) T cells can be used in clinical therapy, as they are considered "safe" for in vivo use. The genetic modification includes inserting of one or more heterologous genes in one or more genomic safe harbour sites. As used herein, a "a genomic safe harbor site" refers to a location in the human genome where foreign genetic material can be added where transgene expression is sustained (i.e., not silenced) and does not perturb expression of endogenous genes. See Sadelain, Nat Rev Cancer, 2012.

Furthermore, the present invention provides methods of producing PSCs (e.g., ESCs, iPSCs, T-iPSCs) that can be used to produce naïve T cells, e.g., phenotypically defined, functional, and/or expandable T cells that possess at least one of the following immunotherapeutic features: 1) targeting one specific predetermined antigen expressed on the cell surface of a target cell in an HLA independent manner, 2) enhanced survival and functional potential and 3) available "off-the-shelf" T cells for administration to multiple recipients, eventually across immunogenic barriers, and 4) cytotoxic potential and anti-tumor activity.

I. Differentiation of T Lymphocytes Having Antigen-Specificity from Endogenous TCR Gene Rearrangements.

T cells gain antigen-specificity through functional rearrangements of antigen recognition regions in their T cell receptors (TCRs). The T cell receptor or TCR is a molecule found on the surface of T lymphocytes (or T cells) that is responsible for recognizing antigens bound to major histocompatibility complex (MHC) molecules. The TCR can be composed of two different protein chains (e.g., a heterodimer). In most (e.g., 95%) T cells, this consists of an alpha ($\alpha$) and beta ($\beta$) chain, whereas in some (e.g., 5%) of T cells, this consists of gamma ($\gamma$) and delta ($\gamma/\delta$) chains. Such T cells having antigen-specificity in cell surface TCR molecules differentiate in vivo into different phenotypic subsets, including, but not limited to, classical CD3$^+$ alpha-beta TCR CD4$^+$, CD3$^+$ alpha-beta TCR CD8$^+$, gamma-delta T cells, Natural Killer T cells, etc. In addition, T cell populations have numerous types for activation states, including, but not limited to, naive, central memory, effector memory, terminal effector, etc. each with distinct functional properties and proliferative capacities in response to antigen-specific interactions, i.e. stimulation. T cells have antigen-specific interactions (reactions) that can be triggered when a specific antigen recognition region on the TCR (including the variable region of each chain which governs antigen-specificity) interacts with a major histocompatibility complex (MHC) molecule capable of triggering the TCR's activation with or without TCR recognition with regions on MHC molecules. The interaction between TCR and a MHC molecule must be just right for certain types of functional activation. The type of activation triggered by the TCR is controlled by many factors, including, but not limited to, strength of antigen to antigen binding/recognition region, e.g., TCR binding to an antigenic peptide within the context of an MHC molecule, the location or binding strength of the antigenic peptide within the MHC molecule, the degree, if any, of HLA or MHC matching to the TCR in the context of the antigenic peptide, costimulatory molecule binding (e.g., CD28), the phenotype of the T cell when it is activated, and cytokines present in the environment. Some of these activation factors can be controlled at least in part, by a target cell, e.g., a tumor or cancerous cell, which often limits cytotoxic activities of T cells (e.g., harming or killing the target cell). In one non-limiting example, T cell activation by a target cell can alternatively result in suppressor T cell activity, where the T cell becomes activated but this activation may not result in harming or killing the target cell. In fact, under certain conditions of stimulation, TCR binding and signaling may result in triggering suicide of the activated T cell (e.g., cell death). Therefore, there is a delicate balance of T cell antigen recognition, TCR signaling, and costimulatory molecule action, along with co-factor contributions for producing functional antigen-specific effector T cells. In addition, similar considerations related to producing antigen-specific effector memory T cells for long term control of tumor cells or viruses.

When the TCR engages with an antigenic peptide and a MHC molecule, the T lymphocyte can be activated through a series of biochemical events mediated by associated enzymes, co-receptors, specialized adaptor molecules, and activated or released transcription factors. Furthermore, activation of a T cell can induce cell proliferation, e.g., cell mitosis to produce daughter cells (e.g., clones). Depending upon the differentiation stage of a T cell and types of activation factors present, activation can result in any of the phenotypic subsets as mentioned above.

Similar to transplantation, adoptive immunotherapy (e.g., adoptive T cell therapy) is often restricted by HLA/MHC matching. Thus, there is often a requirement for HLA/MHC matched T cells in adoptive immunotherapy. Both autologous and non-autologous (e.g., allogeneic, syngenic, or xenogenic) T cells can be used in the adoptive T cell therapy (e.g., methods for treating cancers) of the present invention. In certain embodiments, at least one Human leukocyte antigen (HLA) gene is silenced, knocked out or absent in the CAR-expressing T cells of the present invention.

Known methods for generating autologous functional antigen-specific T cells include activating antigen (including a tumor antigen and a pathogen antigen) specific cytotoxic T lymphocytes (CTLs) isolated from a subject ex vivo in order to increase cell numbers and provide functionally active killer T cells to boost that immune function of the subject. These activated antigen-specific CTLs can be phenotypically characterized as CD3+CD4−CD8+(CD8 single positive: CD8SP) cells (Sensi and Anichini, 2006). Although the activated CTLs can kill or harm tumor cells in vitro, they often are not sufficiently substantial enough to stop tumor cell growth or stop tumor development in the subject. A major limiting factor in this type of approach is the short life span of activated CTLs, which are frequently inactivated quite rapidly by antigen-induced cell death (Mescher et al., 2007; Willimsky and Blankenstein, 2005). For example, isolated $CD8^+$ T cells at least of the naïve subset reactive to a specific antigen are of limited use in adoptive immunotherapy since they have limited in vitro expansion and in vivo persistence. Furthermore, use of these activated CTLs ex vivo in cell therapy is limited mostly due to the difficulty in finding a $CD8^+$ T cell that can target specifically to one specific antigen. Antigen-specific T cells can be obtained by isolation from a subject and non-specific stimulation with CD3 and CD28 or other stimulatory factors. These activated T cells may divide in the present of the antigen for producing endogenously generated antigen-specific T cells. However, these antigen-specific T cells do not always continue to expand in sufficient numbers when further stimulated, e.g., they do not always divide in cell culture to produce more antigen-specific T cells for use in adoptive immunotherapy. For example, the antigen-specific T cells can be exposed to factors preventing expansion in vitro and/or in vivo due to prolonged effect of tumor cell factors present when the T cells are exposed to at least one tumor antigens. Alternatively, these T cell may be terminally differentiated such that they cannot undergo further proliferation. Furthermore, the endogenous numbers of antigen-specific T cells may be limited. Other limitations include, but are not limited to, the target antigen (e.g., a tumor antigen)'s capability to continue to evade or escape from the cytotoxicity of the injected functional T cells from in vitro expansion and activation even when present in higher numbers in the subject.

Isolation of peripheral blood T lymphocytes (PBL) through leukapheresis can provide a source of T lymphocytes (cells) for use in producing antigen-specific T cells that are suitable for adoptive T cell therapy. However, in many cases, e.g., in the case of immune-deficient subjects, autologous T-cell isolation and expansion is problmatic or impossible. Also, in cases of rare HLA/MHC subtypes, it is difficult to obtain HLA/MHC-matched autologous donors.

The antigen-specific T cells generated from CAR-expressing T-iPSCs can circumvent the tolerance (escape) mechanisms utilized by tumor antigens. Differentiated $CAR^+$ T cells of the present invention can target specifically to one specific antigen, including, but not limited to, a tumor antigen and a pathogen antigen. Furthermore, the antigen-specificity of the T cells of the present invention is, not HLA-restricted or is HLA-independent. CARs used in producing the T cells of the present invention do not requires MHC/HLA antigen recognition e.g., CAR does not require the antigen to be presented by a specific MHC/HLA molecule in order to activate or stimulate T cells because antigen-specific stimulation or activation is through the CAR. $CAR^+$ T cells undergo differentiation and commitment to a T cell lineage, and no antigen stimulation is required or necessary before at least about 20 days or at least about 30 days after T lymphoid differentiation. Therefore, CAR+ T cells can be used in adoptive immunotherapy, including treating cancers and treating viral infections, etc.

II. CAR-Expressing PSCs and Methods of Producing Thereof

The present invention provides compositions and methods for producing (providing) precursor T cells, e.g., dedifferentiated (reprogrammed) T cells for producing T-PSCs (e.g, ESCs or iPSCs) that can be modified by a CAR, and compositions and methods for providing a differentiation system including differentiation, expansion, and T cell commitment from dedifferentiated T-PSCs (e.g, ESCs or iPSCs) and CAR-T-PSCs. Compositions include, but are not limited to, cell culture systems and expression vectors. The cell culture systems of the present invention include, but are not limited to, cell culture system for reprogramming a cell's differentiation state (e.g., directing a committed somatic cell to express markers of pluripotent cells). cell culture system for mesoderm induction (e.g., initiating embryoid body formation for mesoderm induction), cell culture systems for hematopoietic specification and expansion, and cell culture systems for T-lymphoid differentiation (inducing committed to a T cell lineage, including inducing effector function in a redifferentiated T cell). The compositions of the present invention include an expression vector (e.g., a CAR vector) for transducing T-PSCs with a CAR.

Human embryonic stem cells (ESCs) and human induced pluripotent stem cells (iPSCs) can be produced by various methods known in the art. PSCs (ESCs or iPSCs) can be used to produce or generate T-PSCs that can be modified by a CAR by, e.g., transducing T-PSCs with a CAR.

PSCs include ESCs and iPSCs. iPSCs can be generated directly from adult cells (e.g., somatic cells). PSCs can be used broadly in regenerative medicine. Since PSCs can propagate indefinitely, as well as give rise to every other cell type in the body (such as neurons, heart, pancreatic, and liver cells), they represent a single source of cells that could be used to replace those lost to damage or disease. iPSCs can be derived or generated by introducing a specific set of pluripotency-associated genes, or "reprogramming factors", into a given cell type. Reprogramming factors include, but are not limited to, OCT4 (also known as "POU5FL"), SOX2, cMYC, and KLF4, which are also known as Yamanaka factors. See Takahashi, K; Yamanaka, S (2006). "Induction of pluripotent stem cells from mouse embryonic and adult fibroblast cultures by defined factors". Cell 126 (4): 663-76. Each of the reprogramming factors can be functionally replaced by related transcription factors, miRNAs, small molecules, or even non-related genes such as lineage specifiers. Upon introduction of reprogramming factors, cells begin to form colonies that resemble PSCs, which can be isolated based on their morphology, conditions that select for their growth, or through expression of surface markers or reporter genes. In certain embodiments, the PSCs used in the methods of the present invention are subject-specific.

There are known technologies for producing PSCs from various types of somatic cells by reprogramming using the Yamanaka factors (OCT4, SOX2, KLF4, and cMYC). For example, reprogramming of mature lymphocytes into iPSCs was accomplished for murine B cells (Hanna et al., 2008; Wada et al., 2011), for murine T cells and mature NK T cells (Watarai et al., 2010a), and for human T cells (Loh et al., 2010; Seki et al., 2010). iPSCs can be produced from human T cells by using whole peripheral mononuclear cells (PB-MCs) or $CD3^+$ cells as a source cell population (Loh et al., 2010; Seki et al., 2010, Staerk et al. 2010. Brown et al, 2010)). The starting T cell population of the known technology often includes about one million cells. In contrast, T-PSCs of the present invention (prior to cell number expansion) can be obtained from about 0.5 million PBMCs or less, which can be from less than about 1 ml of whole blood drawn from a subject.

The CAR-expressing T-PSCs of the present invention can be generated by transducing peripheral blood lymphocytes collected from a subject with at least one retroviral vector. In some embodiments, the retroviral vector is excisable. The retroviral vector can encode at least one reprogramming factors as described above, e.g., ones selected from the group consisting of OCT4, SOX2, KLF4, and cMYC. The retroviral vector can encode a florescent marker. Said fluorescent marker can be selected from the group consisting of green fluorescent protein, blue fluorescent protein, cyan fluorescent protein, yellow fluorescent protein, and a combination thereof. Blue fluorescent protein can be selected from the group consisting of EBFP, EBFP2, Azurite, and mKalama1. Said cyan fluorescent protein can be selected from the group consisting of ECFP, Cerulean, and CyPet. Said yellow fluorescent protein can be selected from the group consisting of YFP, Citrine, Venus, and YPet. In one embodiment, said fluorescent marker is green fluorescent protein. In another embodiment, the fluorescent marker is Citrine.

Use of CAR-expressing T-PSCs to produce T cells can avoid HLA restriction. In accordance with the present invention, the CAR-expressing T-PSCs can be engineered for specific clinical uses. In some embodiments, CAR-expressing T-PSCs can be engineered to down regulate or knock out HLA expression and down regulate or knock out Rag gene expression, in order to generate CAR-expressing T cells that can be used in multiple hosts without rejection or symptoms of graft vs. host disease or to be used as immunosuppressive drugs (e.g., for allogenic cell immunotherapy). In some embodiments, the CAR-expressing T-PSCs can be engineered to not express the transactivator CIITA, which is necessary for transcription of HLA class II genes (e.g., CIITA can be knocked down). In some embodiments, the CAR-expressing T-PSCs can be engineered to not express beta-2 microglobulin, which is necessary for a HLA class 1 molecules' surface expression (e.g., beta-2 microglobulin can be knocked down). The engineered CAR-expressing T-PSCs can be used to generate T cells suitable for many subjects regardless of their HLA haplotypes, and can be used to target tumor cells that have downregulated HLA expression. In addition, the CAR-expressing PSCs can be engineered to express cell surface molecules for effecting the type of activation, for example by transducing cells to express suppressive or tolerogenic ligands using known methods.

III. T Cells Derived from CAR-Expressing PSCs

Use of the T cells derived from ESCs and/or iPSCs by known technologies is limited. The functional characterization of T cells derived from ESCs and iPSCs is complicated by not knowing their antigen-specificity (i.e. TCR antigen-specificity) and/or HLA restriction. For example, T cells generated in vitro from ESCs or iPSCs have an unpredictable TCR repertoire because TCR gene rearrangements are random and the cells are positively selected by unclear mechanisms during their in vitro differentiation (Timmermans, 2009). For example, there is difficulty in finding a $CD8^+$ T cell that target specifically to an antigen (e.g., a tumor antigen or a pathogen antigen) on the cell surface. One or more of the limitations can be circumvented by using iPSCs bearing a rearranged endogenous TCR of known antigen specificity (Vizcardo, 2013; and Nishimura, 2013). However, this approach requires laborious cloning of antigen-specific T cells and is limited to antigens for which patient-specific T cells can be detected.

Additionally, the procedure for isolating a T cell clone typically takes about 4-6 months. Furthermore, although numerous attempts have been made to expand antigen-specific T cells ex vivo in order to boost levels of antigen-responsive T cells that are sufficient to induce a response to a virus or cancerous cell, expanded antigen-specific T cells have been found not effective mainly due to rapid loss of function and low cell numbers (June, C. H. J. Clin. Invest. 117, 1466-1476 (2007)). For example, Brown reported treating patients with advanced melanoma with $CD8^+$ T cell adoptive immunotherapy, eradication of tumors correlated with increased presence of stem cell-like $CD8^+$ T cells (Brown, M. E. et al. PLoS ONE 5, e11373; published online Jun. 29, 2010). Further limitations of using T cells derived from ESCs or iPSCs include 1) not being able to find endogenous T cell clones for every desired antigen, 2) even when a T cell clone for a specific antigen is obtained, it takes months to expand and establish the cell line for use in characterization and/or therapy, 3) antigen recognition is still subject to HLA-restriction or is still HLA-dependent. Thus, these T cells derived from ESCs or iPSCs only recognize antigen in autologous or MHC/HLA-matched systems and these T cells derived from ESCs or iPSCs do not overcome tumor escape of MHC/HLA-downregulation. Furthermore, as TCRs recognize antigens presented by specific HLA molecules, the clinical use of T cells that recognize antigen through an endogenous TCR is constrained by the need to match their specificity to the HLA of the recipient.

Additionally, while numerous attempts have been made to produce iPSCs-derived T cells having endogenous antigen-specificity for use in adoptive immunotherapy, these cells cannot be differentiated into committed effector T cells (Brown, et al. PLoS ONE 5, e11373 2010; Loh, Cell Stem Cell 7, 15-19 (2010); Seki, Cell Stem Cell 7, 11-14 (2010); and Staerk, et al. Cell Stem Cell 7, 20-24 (2010)). Use of mature antigen-specific $CD8^+$ T cells isolated from patients then reprogrammed into iPSCs are reported in Nishimura (2013) and Vizcardo (2013). As reported in Nishimura (2013) and Vizcardo (2013, these antigen-specific iPSCs-derived T cells were redifferentiated into "rejuvenated" proliferative T cells. Nishimura (2013) used mature HIV p27 (nef)-specific $CD8^+$ T cells obtained from a patient infected with HIV-1 to produce iPSCs. Vizcardo (2013) used a melanoma patient-derived T cell line expressing the melanoma epitope melan-A (MLANA; MART1) to produce iPSCs. These iPSCs were then differentiated into mature $CD8^+$ T cells by cytokine exposure along with co-culturing with mouse feeder cells. Because these cells were exposed to murine feeder cells prior to use in mice, these cells may not be acceptable for use in human clinical therapy. Antigen-specificity encoded in the genomic DNA of the parent mature T cells was shown to be conserved in the reprogrammed iPSCs and then by the differentiated mature $CD8^+$ cells.

Further, use of known systems relies upon finding and culturing antigen-specific T cell clones from a subject for each desired antigen. This takes painstaking culturing efforts over long time periods. This process may include multiple blood draws from a subject, especially when the antigen-specificity is in a rare T cell population. Success of this type of method depends upon the presence of antigen-specific T cells, and the number of these antigen-specific T cells circulating in the blood of the subject. The present invention provides T cells that are derived from T-PSCs (ESCs or iPSCs) modified by a chimeric antigen receptor (CAR), e.g., CAR-expressing T-PSCs. These T cells target specifically to one antigen, and antigen-specificity of these T cells is HLA-independent. One advantage of the methods of the present invention for producing CAR-expressing T cells by using CAR-expressing T-PSCs is that no antigen-specific T cell clones are necessary in the starting cell population because antigen-specificity is achieved through interaction of the antigen and the antigen-binding domain of the CAR. In some embodiments, CAR-expressing T cells are produced from one blood draw not multiple blood draw from a subject. Therefore, a few peripheral blood T cells are necessary or required in the starting cell population. In accordance with the present invention, starting cell population can have cell numbers ranging from about $2 \times 10^5$ to about $5 \times 10^5$ peripheral blood T cells from about 0.5 ml to about 1 ml of peripheral blood from a subject.

In addition, one advantage of the methods of the present invention for producing CAR-expressing T cells by using CAR-expressing T-PSCs (ESCs or iPSCs) is the expansion of antigen-specific effector T cells. Unlike known methods for producing T cells from ESCs or iPSCs, where there is no expansion of antigen-specific effector T cells (e.g., using non-antigen-specific T-PSCs, or co-culturing T-PSCs with allo-PBMCs to stimulate cell division to expand T cell populations), CAR-induced antigen-specific signals can stimulate cell division that results in significant expansion of effector T cells.

The methods of the present invention include engineering or modifying T-PSCs with a CAR, which includes an antigen binding or recognition region that binds to one specific antigen. Thus, another advantage of the methods of the present invention is that the target of the T cells does not depend upon the subject's endogenous T cell repertoire or frequency of antigen-specific T cells.

An obstacle of TCRα chain further rearrangement due to Rag gene expression during differentiation, was reported. This type of event typically leads to altered specificity of an antigen recognition region of the TCR. Altered antigen recognition during cell proliferation can be overcome in the methods of the present invention including the use of CAR-expressing T-PSCs through, for example, the constant (stable) expression of the CAR.

In some embodiments, t using a subject's blood cells (e.g., peripheral blood lymphocytes) as a source for reprogramming antigen-specific T cell (e.g., effector T cells) complies with the same rules of HLA compatibility that exist for BMT. Antigen recognition/specificity of CAR-expressing T cells is not dependent on HLA presentation. When using cells from a single clone with the same TCR then the antigen typically must be presented by a certain matching HLA-type in order to be recognized by the T cell, i.e. stimulation. In this situation, tumor cells that frequently down regulate their HLA expression then escape T cell recognition. However, since CAR-based stimulation does not rely upon HLA presentation, the methods of the present invention can overcome HLA down-regulation by tumor cells.

Additionally, phenotypic and functional characterization of the T cells produced by the known technologies are limited. This limitation can be overcome by using CAR-expressing T-PSCs of the present invention, as the CAR-expressing T-PSCs can be expanded in substantial amounts used for in vitro and in vivo functional characterization, phenotyping and for future use in the clinic.

There are known technologies for generating T lymphocytes from human ESCs and/or iPSCs: Galić, et al., Stem Cells, 2009; Timmermans, et al., Journal of Immunology, 2009; Kennedy, et al., Cell Reports, 2012, Nishimura et al. Cell Stem Cell 2013, Vizcardo et al, Cell Stem Cell 2013 and Wakao et al. Cell Stem Cell 2013. However, as the antigen-specificity of these T cells is not known, their therapeutic utility is not known or limited. Further, none of the known technologies use a CAR-expressing ESCs or iPSCs. Since the yield of mature T cells in the known technologies is often extremely low, the potential for further functional investigation is limited and the possibility for in vivo therapeutic application in animal models or for use in generating cells for human immunotherapy is extremely low.

Galić, et al., Stem Cells. 27(1):100-107 (2009) describe using human embryonic stem cells (hESC) as a source through embryoid body (EB) formation for producing T-cell progenitor cells. Galic et al. reported T-cell differentiation from human ESCs through EB-derived T-cell progenitors gave rise to phenotypically and functionally normal cells of the T lineage when transferred into human thymic tissue implanted in immunocompromised mice. Furthermore, Galic et al. showed that following lentiviral-mediated introduction of a vector expressing enhanced green fluorescent protein into hESC, stable transgene expression was maintained throughout differentiation. However, unlike the cell culture systems of the present invention, Galic, et al., added BMP-4 into the cell culture media at Day 4 instead of at the start of differentiation. Further, T cell differentiation in Galic et al. used a murine carrier which renders the produced T cells incompatible for clinical application.

Timmermans, et al. (2009). Generation of T cells from human embryonic stem cell-derived hematopoietic zones. Journal of Immunology, 182, 6879-6888 reported hESC-derived T cells that proliferated in response to PHA stimulation, suggesting that hESCs can give rise to functional T cells. However, Timmermans, et al. used an OP9 feeder culture to induce hematopoietic differentiation instead of the defined cytokine cocktail used in the present invention.

Nishimura (2013), Vizcardo (2013) and Wakao (2013) reported the generation of T cells from T-iPSCs bearing specific TCRs. However the functional characterization of those T cells is limited. Nishimura (2013) and Vizcardo (2013) merely showed in vitro functionality as IFN-γ production and cytotoxic activity against peptide pulsed EBV-transformed B cell lines. The T cells generated in Wakao (2013) showed in vivo function, however they targeted mycobacterium infection in a non-antigen-specific manner. In contrast, the CAR-expressing T cells of the present invention possess not only cytokine secretion activity (e.g., secretion of type 1 cytokines, including IL-2, TNF-α, and IFN-γ), but also in vitro and in vivo cytotoxic activity against tumor cells in mouse and in humans.

However, major issues remain to be resolved before the T cells generated from ESCs and iPSCs of the known technologies can be applied to human regenerative medicine. In addition, T cells generated from ESCs display a polyclonal TCR pattern as random TCR rearrangements take place during differentiation. Therefore, without knowing the TCR specificity, testing the antigen-specific mediated cytotoxic capacity of the generated T cells becomes a random chance occurrence if the matching antigen happens to be present in the assay. It becomes futile when a desired antigen-specific cell is not present. Antigen recognition is an important component of functional evaluation of T cells. In addition, no effective positive selection can take place in such an in vitro differentiation system due to the lack of HLA presentation of matching peptide antigens.

In accordance with the present invention, the T cells derived from CAR-expressing T-PSCs can be any type of T cells, including, but not limited to, T helper cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells), Regulatory T cells (also known as suppressor T cells), Natural killer T cells, Mucosal associated invariant T cells, and γδ T cells. In some embodiments, the CAR-T-PSCs express Foxp3 to achieve and maintain a T regulatory phenotype. Foxp3-expressing regulatory T cells hold the promise to replace and/or supplement indiscriminatory immunosuppression by the CAR-T-PSCs.

IV. Natural Killer (NK) Cells Derived from CAR-Expressing PSCs.

Embryonic stem cell (ESC)-derived natural killer (NK) cells and iPSCs-derived natural killer (NK) cells are another source of anti-tumor lymphocytes for use as immunotherapeutic CAR$^+$ cells. In some embodiments, ESC-derived or iPSC-derived NK cells are used as a source for inducing with a CAR.

NK cells can be derived from ESCs and/or iPSCs, as described in Woll, et al., Journal of Immunology 175:5095-103(2005); Ni, et al., Journal of Virology 85:43-50 (2011); and Knorr, et al., Translational Research 156:147-154 (2010). hESC-derived and iPSC-derived NK cells can have the ability to kill diverse tumor cells both in vitro and in vivo (See Woll (2005); Ni (2011); Woll, et al., Blood 113:6094-6101 (2009)). ESC-derived NK cells can mediate complete tumor clearance in mice engrafted with human leukemia cells (See Woll (2009).

1. Production of NK Cells from ESCs and iPSCs Lines.

ESCs (e.g., H9 line) can be maintained on low-density (90,000 cells/well of a 6 well plate) mouse embryonic fibroblasts (MEF). Generation of hematopoietic progenitor cells from ESCs can be accomplished by using any suitable methods known in the art, e.g., the method described in Ng, et al., (2008). A protocol describing the use of a recombinant protein-based, animal product-free medium (APEL) for human embryonic stem cell differentiation as spin embryoid bodies. Nature Protocols 3:768-776. As described in Ng (2008), spin EBs amenable to aggregation generate can be generated for ESCs and iPSCs lines by passage in TrypLE Select (Invitrogen) on low density mouse embryonic fibroblasts (MEFs, 90,000 cells/well). TrypLE adapted ESCs around 60-70% confluency can be dissociated and filtered through a 70 micron sterile filter. Cells can be counted and placed at a concentration of 3000 cells per well (100 µl volume) of a round-bottom 96-well plate in BPEL medium containing stem cell factor (SCF, 40 ng/ml), vascular endothelial growth factor (VEGF, 20 ng/ml), and bone morphogenic protein 4 (BMP4, 20 ng/ml). The outer wells of the plate can be filled with sterile water to prevent any evaporation of the media. Plates can be spin aggregated at 1,500 RPMs for 5 minutes at room temperature and placed undisturbed in a 37° C. incubator with 5% $CO_2$.

2. NK Cell Differentiation from Spin EBs.

As described in Woll, et al., (2009). Human embryonic stem cells differentiate into a homogeneous population of natural killer cells with potent in vivo antitumor activity. Blood 113:6094-6101, at day 11 differentiation, 6 wells of a 96 well plate can be directly transferred to one well of a 24-well plate in NK cell initiating cytokines (IL-3, IL-7, IL-15, stem cell factor (SCF), fins-like tyrosine kinase receptor-3 ligand (FLT3L). NK cell cultures can be refreshed with 0.5 mL of cytokine containing media every 4-5 days. Mature NK cells can be measured at 28-35 days of culture. Following 4 weeks of NK cell culture, cells can be further expanded using artificial antigen presenting cells (aAPCs) (See Denman, et al., (2012). Membrane-bound IL-21 promotes sustained ex vivo proliferation of human natural killer cells. PLoS ONE 7:e30264).

V. Cell Culture Systems

There are known cell culture systems for T-cell differentiation. See e.g., Salvagiotto, et al., describes a Defined, Feeder-Free, Serum-Free System to Generate In Vitro Hematopoietic Progenitors and Differentiated Blood Cells from hESCs and hiPSCs. PLoS One 2011, and Brown et al. Derivation of induced pluripotent stem cells from human peripheral blood T lymphocytes. PLoS One 5: e11373 (2010).

The cell culture systems for generating CAR-expressing T cells used in the present invention can be serum-free, feeder-free, and/or include feeder cells that are compatible for co-culturing cells for human clinical therapy. In certain embodiments, the cell culture system for generating hematopoietic precursors from human cells is serum-free and feeder-free. This serum-free and feeder-free system relies upon the formation of embryoid bodies (EBs) in cultures of starting cell populations. Starting cell populations include human pluripotent stem cells, e.g., human ESCs and human iPSCs. The cell culture system of the present invention can overcome limitations of known cell culture systems, including but not limited to, donor cell shortages, viral contamination of cells, such as when a patient has in vivo infected cells.

In certain embodiments, the cell culture system of the present invention uses erythroid body (EB) formation in defined serum-free and/or feed-free conditions for generating hematopoietic precursors from T-PSCs (e.g., CAR-expressing T-PSCs). Such cell culture system can result in at least about 70% or at least about 80% of CD3$^+$TCR$^+$ cells in about 30 days of differentiation. For example, in some embodiments, as early as about day 25 of differentiation, CD3$^+$TCR$^+$ can be detected. At about day 30 of differentiation, about 80% CD3$^+$TCR$^+$ cells all express a CAR. Therefore, CAR-expressing T-PSCs can be generated in about 20 days to about 30 days, which is much shorter than the time period (several months or more) required to establish a T cell clone reactive to a specific antigen, if one is found, by known technologies. T-PSCs can be expanded for about 10 days, about 20 days, or for up to about one month. The expanded T-PSCs can be cultured for about 10 days, about 20 days, or up to about one month. Subsequently, for about 10 days, about 20 days, about 30 days, or up to about 35 days, these T-PSCs (e.g., CAR-expressing T-PSCs) can be differentiated into functional T cells (e.g., CAR-expressing T-iPSC-derived effector T cells). Thus, functional CAR-expressing T cells (e.g., CAR-expressing PSCs-derived effector T cells) can be produced within about 4 months, or about 5 months, or up to 6 months after removal of a blood sample from a subject.

T cell differentiation can include four stages: 1) Mesoderm induction (at about days 1-4), 2) Hematopoietic Specification (at about days 4-8) and 3) Hematopoietic commitment and expansion (at about days 8-10), and 4) T-lymphoid differntiation. The cell culture system of the present invention use CAR-expressing undifferentiated PSCs (iPSCs or ESCs) as starting cell population for mesoderm differentiation. These CAR-expressing iPSCs are further differentiated into mesoderm cells. The mesoderm cells are further differentiated into Hematopoietic cells which are expanded in cell numbers followed by inducing these CAR-expressing T-PSCs-derived cells into committed CAR-expressing T-PSC-derived T cells for producing effector T cells capable of long term survival in culture. The cell culture systems of the present invention include, but are not limited to, a first cell culture media for mesoderm induction, a second cell culture media for hematopoietic specification and expansion, and a third cell culture media for T-lymphoid differentiation. The first cell culture media can include BMP-4 (e.g., human BMP-4) and bFGF (e.g., human bFGF). Undifferentiated T-iPSCs or undifferentiated ESCs can be used as the starting cell population. Undifferentiated T-iPSCs or ESCs can be transferred to low-attachment plates to allow for the formation of embryoid bodies (EBs). The formation of EBs during the first stage can be facilitated by an overnight incubation in the presence of hBMP-4. EBs can then be cultured with BMP-4 and bFGF until day 4 to allow for mesoderm induction. The successful induction of mesoderm can be tested by, e.g., measuring the percentage of KDR$^+$PDGFR$^-$ cells.

The second cell culture media can include VEGF (e.g., hVEGF), and a cocktail of hematopoietic cytokines. The cocktail of hematopoietic cytokines can include SCF (e.g., hSCF), Flt3L (e.g., hFlt3L), at least one cytokine, and bFGF for hematopoietic specification. The cytokine can be a Th1 cytokine, which includes, but is not limited to IL-3, IL-15, IL-7, IL-12 and IL-21. EBs can be cultured in the second cell culture media for hematopoietic specification until about day 10. The EBs can be immunophenotypically analyzed by FACS for expression of CD34, CD31, CD43, CD45, CD41a, ckit, Notch1, IL7Rα. In some embodiments, CD34$^+$ cells from about day 10 EBs express the highest levels of key transcription factors for lymphoid differentiation, e.g., CD127 (IL7Rα) and Notch1. The cell culture system of the present invention can produce a surprisingly high yield of hematopoietic progenitors from in vitro directed differentiation of iPSCs or ESCs.

The third cell culture media can include a feeder cell and SCF, Flt3L and at least one cytokine. The cytokine can be a Th1 cytokine, which includes, but is not limited to, IL-3, IL-5, IL-7, IL-12 and IL-21. In some embodiments, the cytokine can add genetic modification(s) to the CAR-T-PSCs in order to enhance the survival and functional potential of the CAR-T-PSC-T cells. In some embodiments, at about day 10, the EBs are dissociated and the hematopoietic precursors are transferred onto a feeder cell to induce T-lymphoid differentiation in an established co-culture system in the presence of the SCF, Flt3L and Th1 cytokine(s) (e.g., IL-7). In some embodiments, the feeder cell is compatible for co-culturing cells for human clinical therapy and expresses a recombinant protein, including, but not limited to, a Delta-like protein (DL)-1, or a delta-like (DL) protein-4 (DL-4). In one embodiment, the feeder cell is a DL-1-expressing OP9 (IP9-DL1) feeder cell.

VI. Chimeric Antigen Receptor (CAR).

Chimeric antigen receptors (CARs) are engineered receptors, which graft an arbitrary specificity onto an immune effector cell. CARs can be used to graft the specificity of a monoclonal antibody onto a T cell; with transfer of their coding sequence facilitated by retroviral vectors.

Any CARs that are suitable for engineering effector cells (e.g., T cells or NK cells) for use in adoptive immunotherapy therapy can be used in the present invention. CARs that can be used in the present invention to engineer or modify PSCs (iPSCs or ESCs) include those described in Sadelain, et al., "The Basic Principles of Chimeric Antigen Receptor Design." Cancer Discovery, OF1-11, (2013), Chicaybam, et al., (2011), Brentjens et al. Nature Medicine 9:279-286 (2003), and U.S. Pat. No. 7,446,190, which are herein incorporated by reference in their entireties, Non-limiting examples of suitable CDRs include, but are not limited to, CD19-targeted CARs (see U.S. Pat. No. 7,446,190; United States Patent Application Publication No. 2013/0071414), HER2-targeted CARs (see Ahmed, et al., Clin Cancer Res., 2010), MUC16-targeted CARs (see Chekmasova, et al., 2011), prostate-specific membrane antigen (PSMA)-targeted CARs (for example, Zhong, et al., Molecular Therapy, 18(2):413-420 (2010), all of which are herein incorporated by reference in their entireties.

CARs can include an extracellular domain, a transmembrane domain and an intracellular domain. The extracellular domain can include an antigen binding/recognition region/domain. The antigen binding domain of the CAR can bind to a specific antigen, e.g., a tumor antigen, a pathogen antigen (e.g., viral antigen), a CD antigen. The extracellular domain can also include a signal peptide that directs the nascent protein into the endoplasmic reticulum. Signal peptide can be essential if the CAR is to be glycosylated and anchored in the cell membrane. The transmembrane domain is a hydrophobic alpha helix that spans the membrane. Different transmembrane domains result in different receptor stability. After antigen recognition, receptors cluster and a signal is transmitted to the cell. The most commonly used intracellular component is CD3ζ which contains 3 ITAMs. This transmits an activation signal to the T cell after antigen is bound. CARs can also include a spacer region that links the antigen binding domain to the transmembrane domain. The spacer region should be flexible enough to allow the antigen binding domain to orient in different directions to facilitate antigen recognition. The spacer can be the hinge region from IgG1, or the $CH_2CH_3$ region of immunoglobulin and portions of CD3.

When used to reprogram T-cell specificity, CARs permit MHC-independent and/or HLA-independent recognition of native rather than processed antigen (Eshhar, et al., Specific activation and targeting of cytotoxic lymphocytes through chimeric single chains consisting of antibody-binding domains and the gamma or zeta subunits of the immunoglobulin and T-cell receptors. Proc. Natl. Acad. Sci. USA 90, 720-724 (1993); Altenschmidt, et al., Specific cytotoxic T lymphocytes in gene therapy. J. Mol. Med. 75, 259-266 (1997); Paillard, F. Immunotherapy with T cells bearing chimeric antitumor receptors. Hum. Gene Ther. 10, 151-153 (1999)).

After antigen recognition, the intracellular domain of the CARs delivers or transmits an activation stimulus or signal to the T cells (Eshhar, (1993); Altenschmidt (1999)). In certain embodiments, one or more costimulatory receptors are included in the intracellular domain other than CD3ζ chain to provide optimal lymphocyte activation. In some examples, lack of a costimulatory signaling can result in poor T-cell proliferative response or in the induction of anergy or apoptosis (Hardin, et al., CD28-mediated signaling co-stimulates murine T cells and prevents induction of anergy in T cell clones. Nature 356, 607-609 (1992); Lenschow, et al., CD28/B7 system of T cell co-stimulation. Annu. Rev. Immunol. 14, 233-258 (1996); Ward, S. G. CD28: a signaling perspective. Biochem. J. 318, 361-377 (1996); Greenfield, et al., CD28/B7 co-stimulation: a review. Crit. Rev. Immunol. 18, 389-418 (1998)). Therefore, it may be valuable to engineer human T cells so that they receive a costimulatory signal in an antigen-dependent manner. An important development in this regard has been the successful design of ScFv-CD28 fusion receptors that transduce a functional antigen-dependent costimulatory signal in human primary T cells, permitting sustained T-cell proliferation when both the endogenous TCR and the chimeric CD28 receptor are engaged (Krause, et al. Antigen-dependent CD28 signaling selectively enhances survival and proliferation in genetically modified activated human primary T lymphocytes. J. Exp. Med. 188, 619-626 (1998). U.S. Patent Publication No. 2002/0018783, which are herein incorporated by reference in their entireties.

There are three generations of CARs. "First generation" CARs are typically composed of an antibody derived antigen recognition domain (e.g., a single-chain variable fragments (scFv)) fused to a transmembrane domain, fused to cytoplasmic signaling domain of the T cell receptor chain. "First generation" CARs typically have the intracellular domain from the CD3 ζ-chain, which is the primary transmitter of signals from endogenous TCRs. "First generation" CARs can provide de novo antigen recognition and cause activation of both CD4$^+$ and CD8$^+$ T cells through their CD3ζ chain signaling domain in a single fusion molecule, independent of HLA-mediated antigen presentation. In one non-limiting example, T lymphocytes can be genetically engineered to express artificial TCRs that direct cytotoxicity toward tumor cells (See Eshhar, et al., Specific activation and targeting of cytotoxic lymphocytes through chimeric single chains consisting of antibody-binding domains and the gamma or zeta subunits of the immunoglobulin and T-cell receptors. Proc. Natl. Acad. Sci. USA 90, 720-724 (1993); Altenschmidt, et al., Specific cytotoxic T lymphocytes in gene therapy. J. Mol. Med. 75, 259-266 (1997)).

"Second generation" CARs add intracellular signaling domains from various costimulatory protein receptors (e.g., CD28, 41BB, ICOS, OX40) to the cytoplasmic tail of the CAR to provide additional signals to the T cell. Maher, Nat Biotechnol, 2002; Brentjens, et al., Clin Cancer Res. (2007) and Stephan, et al., Nat Med., 13(12):1440-9 (2007). "Second generation" CARs can. Preclinical studies have indicated that the "Second generation" CARs improve the antitumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL).

Antigen-specific CAR receptor stimulation does not induce "exhaustion" as demonstrated with TCR-based antigen stimulation or non-specific anti-CD3 antibody based stimulation or allo-PBMC stimulation. Thus, CAR antigen recognition is not limited to endogenous TCR-based antigen recognition but depends upon the antigen-specificity chosen for engineering into antigen specific CAR$^+$ cells.

In accordance with the present invention, the CAR can include an extracellular domain, a transmembrane domain, and an intracellular domain. The extracellular domain of the CAR can include an antigen-binding region that binds to an antigen, which can be, e.g., a tumor antigen or a pathogen antigen. Examples of suitable tumor antigens include, but are not limited to, carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, an antigen of a cytomegalovirus (CMV) infected cell (e.g., a cell surface antigen), epithelial glycoprotein2 (EGP 2), epithelial glycoprotein-40 (EGP-40), epithelial cell adhesion molecule (Ep-CAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), melanoma antigen family A, 1 (MAGE-AI), Mucin 16 (Muc-16), Mucin 1 (Muc-1), Mesothelin (MSLN), NKG2D ligands, cancer-testis antigen NY-ESO-1, oncofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), and Wilms tumor protein (WT-1). In certain embodiments, the antigen-binding region of CAR includes a single-chain variable fragment (scFv). The scFv can be derived from a heavy chain variable region and a light chain variable region of an antibody that binds to the desired antigen. Alternatively, ScFvs can be derived from Fab's (e.g., from Fab libraries). In some embodiments, the CAR is selected to have high affinity or avidity for the antigen.

The transmembrane domain of the CAR can include a CD3ζ polypeptide, a CD4 polypeptide, a CD8 polypeptide, a CD28 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, and a BTLA polypeptide.

The CD3ζ polypeptide can have an amino acid sequence that is at least about 85%, about 90%, about 95%, about 96%, about 97%, about 98%, about 99% or about 100% homologous to SEQ ID NO. 1, or the sequence having a NCBI Reference No: NP_932170, or fragments thereof, which has activating or stimulatory activity.

SEQ ID NO:1 is provided below:

```
  1 mkwkalftaa ilqaqlpite aqsfglldpk lcylldgilf iygviltalf lrvkfsrsad 61 apayqqgqnq lynelnlgrr eeydvldkrr grdpemggkp qrrknpqegl ynelqkdkma 121 eayseigmkg errrgkghdg lyqglstatk dtydalhmqa lppr
```

In accordance with the present invention, a "CD3ζ nucleic acid molecule" refers to a polynucleotide encoding a CD3ζ polypeptide.

The CD8 polypeptide can have an amino acid sequence that is at least about 85%, about 90%, about 95%, about 96%, about 97%, about 98%, about 99% or about 100% homologous to SEQ ID NO: 2 as provided below:

```
MALPVTALLLPLALLLHAARPSQFRVSPLDRTWNLGETVELKCQVLLSNP

TSGCSWLFQPRGAAASPTFLLYLSQNKPKAAEGLDTQRFSGKRLGDTFVL

TLSDFRRENEGYYFCSALSNSIMYFSHFVPVFLPAKPTTTPAPRPPTPAP

TIASQPLSLRPEACRPAAGGAVHTRGLDFACDIYIWAPLAGTCGVLLLSL

VITLYCNHRNRRRVCKCPRPVVKSGDKPSLSARYV
```

In some embodiments, the transmembrane domain of the CAR includes a CD8 polypeptide having an acid sequence of amino acids 137 to 209 of SEQ ID NO: 2.

In accordance with the present invention, a "CD8 nucleic acid molecule" refers to a polynucleotide encoding a CD8 polypeptide.

The intracellular domain of the CAR can include a CD3ζ polypeptide that can activate or stimulate a cell (e.g., a cell of the lymphoid lineage, e.g., a T cell). In certain embodiments, the intracellular domain of the CAR can further include at least one costimulatory signaling region comprising at least one costimulatory molecule. As used herein, "Costimulatory molecules" refer to cell surface molecules other than antigen receptors or their ligands that are required for an efficient response of lymphocytes to antigen. The costimulatory signaling region can include a CD28 polypeptide, a 4-1 BB polypeptide, an OX40 polypeptide, an ICOS polypeptide, a DAP-10 polypeptide, a PD-1 polypeptide, a LAG-3 polypeptide, a 2B4 polypeptide, a BTLA polypeptide, or a CTLA-4 polypeptide. For example, CARs containing the intracellular domain of 4-1BB, ICOS or DAP-10 are disclosed in U.S. Pat. No. 7,446,190 (e.g., the nucleotide sequence encoding 4-1BB is set forth in SEQ ID No: 15, the nucleotide sequence encoding ICOS is set forth in SEQ ID No: 16, and the nucleotide sequence encoding DAP-10 is set forth in SEQ ID No: 17 in U.S. Pat. No. 7,446,190), which is herein incorporated by reference in its entirety. In some embodiments, the intracellular domain of the CAR includes two costimulatory signaling regions comprising CD28 and 4-1BB (Sadelain, et al., Cancer Discovery, OF1-11, (2013)), and CD28-OX40. The costimulatory molecule can bind to a costimulatory ligand, which is a protein expressed on cell surface that upon binding to its receptor produces a costimulatory response, i.e. an intracellular response that effects the stimulation provided when an antigen binds to its CAR molecule of the present invention. Costimulatory ligands, include, but is not limited to CD80, CD86, CD70, OX40L, 4-1BBL, CD48, TNFRSF14, and PD-L1. As one example, a 4-1BB ligand (i.e., 4-1BBL) may bind to 4-1BB (also known as "CD137") for providing an intracellular signal that in combination with a CAR signal induces an effector cell function of the CAR+ T cell.

A CD28 polypeptide can have an amino acid sequence that is at least about 85%, about 90%, about 95%, about 96%, about 97%, about 98%, about 99% or 100% homologous to the sequence having a NCBI Reference No: or P10747 or NP_006130 (SEQ ID No. 3), or NP_001230006 (SEQ ID NO:4), or fragments thereof, which has stimulatory activity.

SEQ ID NO:3 is provided below:

```
  1 MLRLLLALNL FPSIQVTGNK ILVKQSPMLV AYDNAVNLSC KYSYNLFSRE FRASLHKGLD
 61 SAVEVCVVYG NYSQQLQVYS KTGFNCDGKL GNESVTFYLQ NLYVNQTDIY FCKIEVMYPP
121 PYLDNEKSNG TIIHVKCKHL CPSPLFPGPS KPFWVLVVVG GVLACYSLLV TVAFIIFWVR
181 SKRSRLLHSD YMNMTPRRPG PTRKHYOPYA PPRDFAAYRS
```

SEQ ID NO:4 is provided below:

```
  1 MLRLLLALNL FPSIQVTGNK ILVKQSPMLV AYDNAVNLSW KHLCPSPLFP GPSKPFWVLV
 61 VVGGVLACYS LLVTVAFIIF WVRSKRSRLL HSDYMNMTPR RPGPTRKHYQ PYAPPRDFAA
121 YRS
```

In accordance with the present invention, a "CD28 nucleic acid molecule" refers to a polynucleotide encoding a CD28 polypeptide.

An OX40 polypeptide can have an amino acid sequence that is at least about 85%, about 90%, about 95%, about 96%, about 97%, about 98%, about 99% or 100% homologous to the sequence having a NCBI Reference No: P43489 or NP_003318 (SEQ ID No:5), or fragments thereof, which has stimulatory activity.

SEQ ID NO:5 is provided below:

```
  1 MCVGARRLGR GPCAALLLLG LGLSTVTGLH CVGDTYPSND RCCHECRPGN GMVSRCSRSQ
 61 NTVCRPCGPG FYNDVVSSKP CKPCTWCNLR SGSERKQLCT ATQDTVCRCR AGTQPLDSYK
121 PGVDCAPCPP GHFSPGDNQA CKPWTNCTLA GKHTLQPASN SSDAICEDRD PPATQPQETQ
181 GPPARPITVQ PTEAWPRTSQ GPSTRPVEVP GGRAVAAILG LGLVLGLLGP LAILLALYLL
241 RRDQRLPPDA HKPPGGGSFR TPIQEEQADA HSTLAKI
```

In accordance with the present invention, an "OX40 nucleic acid molecule" refers to a polynucleotide encoding an OX40 polypeptide.

A 4-BB polypeptide can have an amino acid sequence that is at least about 85%, about 90%, about 95%, about 96%, about 97%, about 98%, about 99% or 100% homologous to the sequence having a NCBI Reference No: P41273 or NP_001552 or fragments thereof (SEQ ID NO:6), which acts as s tumor necrosis factor (TNF) ligand and has stimulatory activity.

SEQ ID NO:6 is provided below:

```
  1 MGNSCYNIVA TLLLVLNFER TRSLQDPCSN CPAGTFCDNN RNQICSPCPP NSFSSAGGQR

61 TCDICRQCKG VFRTRKECSS TSNAECDCTP GFHCLGAGCS MCEQDCKQGQ ELTKKGCKDC

121 CFGTENDQKR GICRPWTNCS LDGKSVLVNG TKERDVVCGP SPADLSPGAS SVTPPAPARE

181 PGHSPQIISF FLALTSTALL FLLFFLTLRF SVVKRGRKKL LYIFKQPFMR PVQTTQEEDG

241 CSCRFPEEEE GGCEL
```

In accordance with the present invention, a "4-1BB nucleic acid molecule" refers to a polynucleotide encoding a 4-1BB polypeptide.

An ICOS polypeptide can have an amino acid sequence that is at least about 85%, about 90%, about 95%, about 96%, about 97%, about 98%, about 99% or 1000/homologous to the sequence having a NCBI Reference No: NP_036224 (SEQ ID NO:7) or fragments thereof, which has stimulatory activity.

SEQ ID NO:7 is provided below:

```
  1 MKSGLWYFFL FCLRIKVLTG EINGSANYEM FIFHNGGVQI LCKYPDIVQQ FKMQLLKGGQ

61 ILCDLTKTKG SGNTVSIKSL KFCHSQLSNN SVSFFLYNLD HSHANYYFCN LSIFDPPPFK

121 VTLTGGYLHI YESQLCCQLK FWLPIGCAAF VVVCILGCIL ICWLTKKKYS SSVHDPNGEY

181 MFMRAVNTAK KSRLTDVTL
```

In accordance with the present invention, a "ICOS nucleic acid molecule" refers to a polynucleotide encoding a ICOS polypeptide.

CTLA-4 is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion, enhanced the endogenous anti-tumor response albeit, in the clinical setting, with significant unforeseen toxicities.

CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM motif able to bind PI3K, PP2A and SHP-2 and one proline-rich motif able to bind SH3 containing proteins. One role of CTLA-4 in inhibiting T cell responses seem to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 has also been shown to bind and/or interact with PI3K, CD80, AP2M1, and PPP2R5A.

A CTLA-4 polypeptide can have an amino acid sequence as set forth in SEQ ID NO:8.

In accordance with the present invention, a CTLA-4 polypeptide can have an amino acid sequence that is at least 85%, 90%, 95%, 96%, 97%, 98%, 99% or 100% homologous to SEQ ID NO:8 (homology herein may be determined using standard software such as BLAST or FASTA). In non-limiting embodiments, a CTLA-4 polypeptide can have an amino acid sequence that is a consecutive portion of SEQ ID NO:8 which is at least 20, or at least 30, or at least 40, or at least 50, and up to 222 amino acids in length. Alternatively or additionally, in non-limiting various embodiments, the CTLA-4 polypeptide has an amino acid sequence of amino acids 1 to 223, 1 to 50, 50 to 100, 100 to 140, 141 to 161, 162 to 182, 183 to 223, 141 to 223, 162 to 223, or 183 to 223 of SEQ ID NO:8. In one embodiment, the CTLA-4 polypeptide has an amino acid sequence of amino acids 183 to 223 of SEQ ID NO:8. In certain embodiments, the intracellular signaling domain of the CAR includes a CTLA-4 polypeptide having an amino acid sequence of amino acids 183 to 223 of SEQ ID NO:8. In certain embodiments, the transmembrane domain of the CAR includes a CTLA-4 polypeptide having an amino acid sequence of amino acids 162 to 182 of SEQ ID NO:8.

In accordance with the present invention, a "CTLA-4 nucleic acid molecule" refers to a polynucleotide encoding a CTLA-4 polypeptide.

PD-1 is a negative immune regulator of activated T cells upon engagement with its corresponding ligands PD-L1 and PD-L2 expressed on endogenous macrophages and dendritic cells. PD-1 is a type I membrane protein of 268 amino acids. PD-1 has two ligands, PD-L1 and PD-L2, which are members of the B7 family. The protein's structure includes an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, that PD-1 negatively regulates TCR signals. SHP-1 and SHP-2 phosphatases bind to the cytoplasmic tail of PD-1 upon ligand binding. Upregulation of PD-L1 is one mechanism tumor cells may evade the host

```
  1 MACLGFQRHK AQLNLATRTW PCTLLPPLLF IPVFCKAMHV AQPAVVLASS RGIASFVCEY

51 ASPGKATEVR VTVLRQADSQ VTEVCAATYM MGNELTFLDD SICTGTSSGN QVNLTIQGLR

121 AMDTGLYICK VELMYPPPYY LGIGNGTQIY VIDPEPCPDS DFLLWILAAV SSGLFFYSFL

181 LTAVSLSKML KKRSPLTTGV YVKMPPTEPE CEKQFQPYFI PIN
``` immune system. In pre-clinical and clinical trials, PD-1 blockade by antagonistic antibodies induced anti-tumor responses mediated through the host endogenous immune system.

A PD-1 polypeptide can have an amino acid sequence as set forth in SEQ ID NO:9.

```
  1 mqipqapwpv vwavlqlgwr pgwfldspdr pwnpptfspa llvvtegdna tftcsfsnts
 61 esfvlnwyrm spsnqtdkla afpedrsqpg qdcrfrvtql pngrdfhmsv vrarrndsgt
121 ylcgaislap kaqikeslra elrvterrae vptahpspsp rpagqfqtlv vgvvggllgs
181 lvllvwvlav icsraargti garrtgqplk edpsavpvfs vdygeldfqw rektpeppvp
241 cvpeqteyat ivfpsgmgts sparrgsadg prsagplrpe dghcswpl
```

In accordance with the present invention, a PD-1 polypeptide can have an amino acid sequence that is at least 85%, 90%, 95%, 96%, 97%, 98%, 99% or 100% homologous to SEQ ID NO:9. In non-limiting embodiments, a PD-1 polypeptide can have an amino acid sequence that is a consecutive portion of SEQ ID NO:9 which is at least 20, or at least 30, or at least 40, or at least 50, and up to 287 amino acids in length. Alternatively or additionally, in non-limiting various embodiments, a PD-1 polypeptide has an amino acid sequence of amino acids 1 to 288, 1 to 50, 50 to 100, 100 to 144, 145 to 170, 171 to 191, 192 to 288, 145 to 288, 171 to 288, or 192 to 288 of SEQ ID NO:9. In one embodiment, the PD-1 polypeptide has an amino acid sequence of amino acids 192 to 288 of SEQ ID NO:9. In certain embodiments, the intracellular signaling domain of the CAR includes a PD-1 polypeptide having an amino acid sequence of amino acids 192 to 288 of SEQ ID NO:9. In certain embodiments, the transmembrane domain of the CAR includes a PD-1 polypeptide having an amino acid sequence of amino acids 171 to 191 of SEQ ID NO:9.

In accordance with the present invention, a "PD-1 nucleic acid molecule" refers to a polynucleotide encoding a PD-1 polypeptide.

Lymphocyte-activation protein 3 (LAG-3) is a negative immune regulator of immune cells. LAG-3 belongs to the immunoglobulin (Ig) superfamily and contains 4 extracellular Ig-like domains. The LAG3 gene contains 8 exons. The sequence data, exon/intron organization, and chromosomal localization all indicate a close relationship of LAG3 to CD4. LAG3 has also been designated CD223 (cluster of differentiation 223).

A LAG-3 polypeptide can have an amino acid sequence as set forth in SEQ ID NO:10.

In accordance with the present invention, a LAG-3 polypeptide can have an amino acid sequence that is at least 85%, 90%, 95%, 96%, 97%, 98%, 99% or 100% homologous to SEQ ID NO: 10. In non-limiting embodiments, a LAG-3 polypeptide can have an amino acid sequence that is a consecutive portion of SEQ ID NO: 10 which is at least 20, or at least 30, or at least 40, or at least 50, and up to 524 amino acids in length. Alternatively or additionally, in non-limiting various embodiments, a LAG-3 polypeptide has an amino acid sequence of amino acids 1 to 525, 1 to 50, 50 to 100, 100 to 150, 150 to 200, 200 to 250, 250 to 300, 300 to 350, 350 to 400, 400 to 420, 421 to 450, 451 to 471, 472 to 525, 421 to 525, 451 to 525, or 472 to 525 of SEQ ID NO:10. In one embodiment, the LAG-3 polypeptide has an amino acid sequence of amino acids 472 to 525 of SEQ ID NO:10. In certain embodiments, the intracellular signaling domain of the CAR includes a LAG-3 polypeptide having an amino acid sequence of amino acids 472 to 525 of SEQ ID NO:10. In certain embodiments, the transmembrane domain of the CAR includes a LAG-3 polypeptide having an amino acid sequence of amino acids 451 to 471 of SEQ ID NO:10.

In accordance with the present invention, a "LAG-3 nucleic acid molecule" refers to a polynucleotide encoding a LAG-3 polypeptide.

Natural Killer Cell Receptor 2B4 (2B4) mediates non-MHC restricted cell killing on NK cells and subsets of T cells. To date, the function of 2B4 is still under investigation, with the 2B4-S isoform believed to be an activating receptor, and the 2B4-L isoform believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

A 2B4 polypeptide can have an amino acid sequence as set forth in SEQ ID NO: 11.

```
  1 mweagflgll flqplwvapv kplqpgaevp vvwaqegapa qlpcsptipl qdlsllrrag
 61 vtwqhqpdag ppaaapghpl apgphpaaps swgprprryt vlsvgpgglr sgrlplgprv
121 qldergrqrg dfslwlrpar radageyraa vhlrdralsc rlrlrlgqas mtasppgslr
181 asdwvilncs fsrpdrpasv hwfrnrgqgr vpvresphhh laesflflpq vspmdsgpwg
241 ciltyrdgfn vsimynltvl glepptpltv yagagsrvgl pcrlpagvgt rsfltakwtp
301 pgggpdllvt gdpgdftlrl edvsqaqagt ytchihlqeq qlnatvtlai itvtpksfgs
361 pgslgkllce vtpvsgqerf vwssldtpsq rsfsgpwlea qeaqllsqpw qcqlyqgerl
421 lgaavyftel sspgaqrsgr apgalpaghl llflilgvls lllltvtgafg fhlwrrqwrp
481 rrfsaleqgi hppqaqskie eleqepepep epepepepep epeql
```

```
  1 mlgqvvtlil llllkvyqgk gcqgsadhvv sisgvplqlq pnsiqtkvds iawkkllpsq 61 ngfhhilkwe ngslpsntsn drfsfivknl sllikaaqqq dsglyclevt sisgkvqtat 121 fqvfvfesll pdkvekprlq gqgkildrgr cqvalsclvs rdgnvsyawy rgskliqtag 181 nltyldeevd ingthtytcn vsnpvswesh tlnltqdcqn ahqefrfwpf lviivilsal 241 flgtlacfcv wrrkrkekqs etspkeflti yedvkdlktr rnheqeqtfp gggstiysmi 301 qsqssaptsq epaytlysli qpsrksgsrk rnhspsfnst iyevigksqp kaqnparlsr 361 kelenfdvys
```

In accordance with the present invention, a 2B4 polypeptide can have an amino acid sequence that is at least 85%, 90%, 95%, 96%, 97%, 98%, 99% or 100% homologous to SEQ ID NO:11. In non-limiting embodiments, a 2B4 polypeptide can have an amino acid sequence that is a consecutive portion of SEQ ID NO:11 which is at least 20, or at least 30, or at least 40, or at least 50, and up to 369 amino acids in length. Alternatively or additionally, in non-limiting various embodiments, a 2B4 polypeptide has an amino acid sequence of amino acids 1 to 370, 1 to 50, 50 to 100, 100 to 150, 150 to 215, 216 to 229, 230 to 250, 251 to 370, 216 to 370, 230 to 370, or 251 to 370 of SEQ ID NO:11. In one embodiment, the 2B4 polypeptide has an amino acid sequence of amino acids 251 to 370 of SEQ ID NO:11. In certain embodiments, the intracellular signaling domain of the CAR includes a 2B4 polypeptide having an amino acid sequence of amino acids 251 to 370 of SEQ ID NO:11. In certain embodiments, the transmembrane domain of the CAR includes a 2B4 polypeptide having an amino acid sequence of amino acids 230 to 250 of SEQ ID NO: 11.

In accordance with the present invention, a "2B4 nucleic acid molecule" refers to a polynucleotide encoding a 2B4 polypeptide.

B- and T-lymphocyte attenuator (BTLA) expression is induced during activation of T cells, and BTLA remains expressed on Th1 cells but not Th2 cells. Like PD1 and CTLA4, BTLA interacts with a B7 homolog, B7H4. However, unlike PD-1 and CTLA-4, BTLA displays T-Cell inhibition via interaction with tumor necrosis family receptors (TNF-R), not just the B7 family of cell surface receptors. BTLA is a ligand for tumour necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human CD8+ cancer-specific T cells. BTLA has also been designated as CD272 (cluster of differentiation 272).

A BTLA polypeptide can have an amino acid sequence as set forth in SEQ ID NO:12.

In accordance with the present invention, a BTLA polypeptide can have an amino acid sequence that is at least 85%, 90%, 95%, 96%, 97%, 98%, 99% or 100% homologous to SEQ ID NO:12. In non-limiting embodiments, a BTLA polypeptide can have an amino acid sequence that is a consecutive portion of SEQ ID NO:12 which is at least 20, or at least 30, or at least 40, or at least 50, and up to 288 amino acids in length. Alternatively or additionally, in non-limiting various embodiments, a BTLA polypeptide has an amino acid sequence of amino acids 1 to 289, 1 to 50, 50 to 100, 100 to 134, 135 to 157, 158 to 178, 179 to 289, 135 to 289, 158 to 289, or 179 to 289 of SEQ ID NO:12. In one embodiment, the BTLA polypeptide has an amino acid sequence of amino acids 179 to 289 of SEQ ID NO:12. In certain embodiments, the intracellular signaling domain of the CAR includes a BTLA polypeptide having an amino acid sequence of amino acids 179 to 289 of SEQ ID NO: 12. In certain embodiments, the transmembrane domain of the CAR includes a BTLA polypeptide having an amino acid sequence of amino acids 158 to 178 of SEQ ID NO:12.

In accordance with the present invention, a "BTLA nucleic acid molecule" refers to a polynucleotide encoding a BTLA polypeptide.

An OX40L polypeptide can have an amino acid sequence that is at least about 85%, about 90%, about 95%, about 96%, about 97%, about 98%, about 99% or 100% homologous to the sequence having a NCBI Reference No: BAB18304 or NP_003317 (SEQ ID NO: 13), or fragments thereof that is a tumor necrosis factor (TNF) ligand.

```
  1 MKTLPAMLGT GKLFWVFFLI PYLDIWNIHG KESCDVQLYI KRQSEHSILA GDPFELECPV

61 KYCANRPHVT WCKLNGTTCV KLEDRQTSWK EEKNISFFIL HFEPVLPNDN GSYRCSANFQ

121 SNLIESHSTT LYVTDVKSAS ERPSKDEMAS RPWLLYRLLP LGGLPLLITT CFCLFCCLRR

181 HQGKQNELSD TAGREINLVD AHLKSEQTEA STRQNSQVLL SETGIYDNDP DLCFRMQEGS

241 EVYSNPCLEE NKPGIVYASL NHSVIGPNSR LARNVKEAPT EYASICVRS
```

SEQ ID NO: 13 is provided below:

```
  1 mervqpleen vgnaarprfe rnklllvasv iqglglllcf tyiclhfsal qvshrypriq
 61 sikvqfteyk kekgfiltsq kedeimkvqn nsviincdgf ylislkgyfs qevnislhyq
121 kdeeplfqlk kvrsvnslmv asltykdkvy lnvttdntsl ddfhvnggel ilihqnpgef
181 cvl
```

In accordance with the present invention, an "OX40L nucleic acid molecule" refers to a polynucleotide encoding an OX40L polypeptide.

A 4-1BB polypeptide can have an amino acid sequence that is at least about 85%, about 90%, about 95%, about 96%, about 97%, about 98%, about 99% or 100%/c homologous to the sequence having a NCBI Reference No: P41273 or NP_001552.2 (SEQ ID NO: 14) or a fragment thereof that that acts as a tumor necrosis factor (TNF) ligand.

SEQ ID NO:14 is provided below:

```
  1 mgnscyniva tlllvlnfer trslgdpcsn cpagtfcdnn rngicspcpp nsfssaggqr
 61 tcdicrqckg vfrtrkecss tsnaecdctp gfhclgagcs mceqdckqgq eltkkgckdc
121 cfgtfndqkr gicrpwtncs ldgksvlvng tkerdvvcgp spadlspgas svtppapare
181 pghspqiisf flaltstall fllffltlrf svvkrgrkkl lyifkqpfmr pvqttqeedg
241 cscrfpeeee ggcel
```

In accordance with the present invention, a "4-1BB nucleic acid molecule" refers to a polynucleotide encoding a 4-1BB polypeptide.

In one embodiment, the CAR is 1928z, which comprises an antigen binding region that binds to a B-cell lineage antigen CD19, and a costimulatory signaling domain that comprises a CD28 polypeptide. "1928z" refers to a protein having at least about 85%, about 90%, about 95%, about 96%, about 97%, about 98%, about 99% or about 100% homologous to SEQ ID NO:15, which includes a CDS leader sequence at amino acids 1-18, and is able to bind to CD19.

SEQ ID NO: 15 is provided below:

MALPVTALLLPLALLLHAEVKLQQSGAELVRPGSSVKISCKASGYAFSSY

WMNWVKQRPGQGLEWIGQIYPGDGDTNYNGKFKGQATLTADKSSSTAYMQ

LSGLTSEDSAVYFCARKTISSVVDFYFDYWGQGTTVTVSSGGGGSGGGGS

GGGGSDIELTQSPKFMSTSVGDRVSVTCKASQNVGTNVAWYQQKPGQSPK

PLIYSATYRNSGVPDRFTGSGSGTDFTLTITNVQSKDLADYFCQQYNRYP

YTSGGGTKLEIKRAAAIEVMYPPPYLDNEKSNGTIIHVKGKHLCPSPLFP

GPSKPFWVLVVVGGVLACYSLLVTVAFIIFWVRSKRSRLLHSDYMNMTPR

RPGPTRKHYQPYAPPRDFAAYRSRVKFSRSAEPPAYQQGQNQLYNELNLG

RREEYDVLDKRRGRDPEMGGKPRRKNPQEGLYNELQKDKMAEAYSEIGMK

GERRRGKGHDGLYQGLSTATKDTYDALHMQALPPRX

An exemplary nucleic acid sequence encoding a 1928z polypeptide, including a CDS leader sequence, is provided in SEQ ID NO: 16, which is provided below.

```
ccatggctctcccagtgactgccctactgcttcccctagcgcttctcctg
catgcagaggtgaagctgcagcagtctggggctgagctggtgaggcctgg
gtcctcagtgaagatttcctgcaaggcttctggctatgcattcagtagct
actggatgaactgggtgaagcagaggcctggacagggtcttgagtggatt
ggacagatttatcctggagatggtgatactaactacaatggaaagttcaa
```

-continued

```
gggtcaagccacactgactgcagacaaatcctccagcacagcctacatgc
agctcagcggcctaacatctgaggactctgcggtctatttctgtgcaaga
aagaccattagttcggtagtagatttctactttgactactggggccaagg
gaccacggtcaccgtctcctcaggtggaggtggatcaggtggaggtggat
ctggtggaggtggatctgacattgagctcacccagtctccaaaattcatg
tccacatcagtaggagacagggtcagcgtcacctgcaaggccagtcagaa
tgtgggtactaatgtagcctggtatcaacagaaaccaggacaatctccta
aaccactgatttactcggcaacctaccggaacagtggagtccctgatcgc
ttcacaggcagtggatctgggacagatttcactctcaccatcactaacgt
gcagtctaaagacttggcagactatttctgtcaacaatataacaggtatc
cgtacacgtccggaggggggaccaagctggagatcaaacgggcggccgca
attgaagttatgtatcctcatccttacctagacaatgagaagagcaatgg
aaccattatccatgtgaaagggaaacacctttgtccaagtcccctatttc
ccggaccttctaagccttttgggtgctggtggtggttagtggagtcctg
gcttgctatagcttgctagtaacagtggcctttattattttctgggtgag
gagtaagaggagcaggctcccgcacagtgactacatgaacatgactcccc
gccgccccgggcccacccgcaagcattaccagccctatgccccaccacgc
gacttcgcagcctatcgctccagagtgaagttcagcaggagcgcagagcc
ccccgcgtaccagcagggccagaaccagctctataacgagctcaatctag
gacgaagagaggagtacgatgtttggacaagagacgtggccgggaccct
gagatggggggaaagccgagaaggaagaaccctcaggaaggcctgtacaa
```

-continued
```
tgaactgcagaaagataagatggcggaggcctacagtgagattgggatga aaggcgagcgccggaggggcaaggggcacgatggcctttaccagggtctc agtacagccaccaaggacacctacgacgcccttcacatgcaggccctgcc ccctcgcg
```

In some embodiments, the CAR of the present invention can further comprise an inducible promoter, for expressing nucleic acid sequences in human cells. Promoters for use in expressing CAR genes can be a constitutive promoters, such as ubiquitin C (UbiC) promoter.

In some embodiments, the extracellular domain of the CAR of the present invention can further include a signal peptide that directs the nascent protein into the endoplasmic reticulum. The CAR of the present invention can also include a spacer region that links the antigen binding domain to the transmembrane domain. The spacer region should be flexible enough to allow the antigen binding domain to orient in different directions to facilitate antigen recognition. The spacer can be the hinge region from IgG1, or the $CH_2CH_3$ region of immunoglobulin and portions of CD3

PSCs (iPSCs or ESCs) can be transduced with the CAR to generate CAR-expressing PSCs. The generation of CAR-expressing PSCs can be evaluated in stimulation assays with artificial antigen presenting cells (AAPCs) expressing the antigen to which the CAR antigen binding region can bind and recognize. The T cells derived from CAR-expressing T-PSCs have a TCR-like strong survival and proliferative signal through the CD3ζ chain and further through co-stimulation provided by CD28.

Using a CAR for antigen recognition can avoid the potential for future TCR gene rearrangement. Further, by reprogramming a T cell into a T-PSC which has a greater proliferation and differentiation potential than a T cell, these T-PSCs (e.g., CAR-expressing T-PSCs can be used for genetic manipulations. T-PSCs can be transduced by a molecule, including, but not limited to, a CAR, a specific TCR, a costimulatory ligand, a suicide gene (e.g., hsvtk, inducible caspase), an inducible cytokine and an imaging gene. In one embodiment, the T-PSC are transduced with a CAR. These molecules can be inserted within a genomic safe harbor such as the one identified in Papapetrou, Nat Biotech (2011). Targeting of a specific safe genomic harbor can be achieved by homologous recombination using a nuclease (e.g. Transcription activator-like effector nucleases (TALENs)). Additionally, MHC/HLA expression may be manipulated as described herein, and by knocking out or silencing Rag genes in order to provide the CAR+ T cell with a universal application potential, i.e. allogeneic use. Therefore, cell effector function of CAR+ T cells is amendable for manipulation and enhancement in a clinically safe manner. Moreover, the engineering process (vector construction) provides an opportunity to engineer the vector to integrate into a selected chromosomal integration site for the CAR by targeting specific "genomic safe harbor" sites (see, Papapetrou et al Nat Biotech 2011). In some embodiments, the vectors comprise targeting sequences for integration into a genomic safe harbor site.

In one non-limiting embodiment, T-PSCs are produced from peripheral blood T-cells, which are stably transduced with a vector encoding a CAR, and a fluorescent marker. Suitable vectors include, but are not limited to a lentiviral vector, a retroviral vector. Other approaches that can target DNAs to a selected "genomic safe harbor", e.g., Tha15.10 (Papapetrou, 2011 or 2012) and AAVS1, can also be used to produce T-PSCs from T cells. In some embodiments, the fluorescent marker is mCherry. An exemplary mCherry encoding sequence is provided in SEQ ID NO:17:

```
Atggtgagcaagggcgaggaggataacatggccatcatcaaggagttcat gcgcttcaaggtgcacatggagggctccgtgaacggccacgagttcgaga tcgagggcgagggcgagggccgcccctacgagggcacccagaccgccaag ctgaaggtgaccaagggtggcccctgcccttcgcctgggacatcctgtc ccctcagttcatgtacggctccaaggcctacgtgaagcacccgccgaca tccccgactacttgaagctgtccttccccgagggcttcaagtgggagcgc gtgatgaacttcgaggacggcggcgtggtgaccgtgacccaggactcctc cctgcaggacggcgagttcatctacaaggtgaagctgcgcggcaccaact tccctccgacggcccccgtaatgcagaagaagaccatgggctgggaggcc tcctccgagcggatgtaccccgaggacggcgccctgaagggcgagatcaa gcagaggctgaagctgaaggacggcggccactacgacgctgaggtcaaga ccacctacaaggccaagaagcccgtgcagctgcccggcgcctacaacgtc aacatcaagttggacatcacctcccacaacgaggactacaccatcgtgga acagtacgaacgcgccgagggccgccactccaccggcggcatggacgagc tgtacaag.
```

The fluorescent marker can be used to sort CAR-expressing T-PSCs by sorting for high expression of the fluorescent marker, identification, tracking, in vitro and in vivo. The CAR-expressing T-PSCs can be re-differentiated to hematopoietic precursors, which can be further differentiated to T lymphoid lineage. The T cells derived or produced from CAR-expressing T-PSCs of the present invention express the CAR on their surface and can respond to, target to, or recognize the specific antigen to which the antigen binding region of the CAR target. For example, the T cells produced or derived from 1928ZCAR-expressing T-PSCs can target to or recognize CD19, e.g., the CD19 expressed on cell surface of NIH-3T3 cells (AAPCs) (Latouche et al. Nat Biotech 2000). After antigen recognition, the intracellular domain of the CAR (e.g., CD3ζ alone or CD3ζ combined with one or more costimulatory signaling peptides (e.g., CD28, 4-1BB, ICOS, and/or OX40) transmits an activation signal to the T cells. The CAR-expressing T cells of the present invention can secrete cytokines, e.g., Th1 cytokines including, but not limited to IFN-γ, IL-2 and TNF-α. In addition, the CAR-expressing T cells of the present invention can be expanded 10- to 50-fold after one stimulation (e.g., day 30 differentiation) and up to about 1,000-fold after three rounds of stimulations. Additional activities possessed by the CAR-expressing T cells of the present invention include cytotoxicity and cytostatic inhibition of cell growth. Cytostatic inhibition of cell growth can result in killing the cells that express the antigen recognized by the CAR. Due to the cytostatic inhibition of cell growth activity, the CAR-expressing T cells of the present invention can be used for treating tumors or cancers. In addition, antigen recognition of CARs does not require HLA class I presentation, and thus, the CAR-expressing T cells derived from CAR-expressing T-PSCs can recognize tumors across MHC barriers. For at least the above, the CAR-expressing T cells of the present invention can be in adoptive immunotherapy (adoptive T cell therapy).

Through the use of cell culture systems described herein for differentiation and dedifferentiation of source cells, including, but not limited to, PSCs, iPSCs, ESCs, cord blood, peripheral blood cells, peripheral blood T cells, etc., the yield obstacle of in vitro T-cell differentiation of PSCs for a specific antigen reactivity was overcome. Thus, the CAR-expressing T cells of the present invention can be used for in vivo functional assessment in mouse models and for clinical use.

VII. Vectors

Genetic modification of cells (e.g., T cells, NK cells and iPSCs and ESCs) can be accomplished by transducing a substantially homogeneous cell composition with a recombinant DNA or RNA construct. Preferably, a retroviral vector (either gamma retroviral or lentiviral) is employed for the introduction of the DNA or RNA construct into the host cell genome. For example, a polynucleotide encoding a receptor that binds an antigen (e.g., a tumor antigen, or a variant, or a fragment thereof), can be cloned into a retroviral vector and expression can be driven from its endogenous promoter, from the retroviral long terminal repeat, or from an alternative internal promoter. Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide tumor or viral antigen-specific cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad Sci.* USA 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Transducing viral vectors can be used to express a co-stimulatory ligand in an immunoresponsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272: 263 267, 1996; and Miyoshi et al., Proc. Natl. Acad. Sci. U.S.A. 94:10319, 1997). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the expression of a protein in cell. For example, a nucleic acid molecule can be introduced into a cell by administering the nucleic acid in the presence of lipofection (Feigner et al., Proc. Nat!. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1 α enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

VIII. Administration

Cell populations comprising T cells derived from CAR-expressing T-PSCs and compositions comprising thereof of the present invention can be provided systemically or directly to a subject for the treatment of a neoplasia, pathogen infection, or infectious disease. In one embodiment, T cells of the present invention are directly injected into an organ of interest (e.g., an organ affected by a neoplasia). Alternatively, T cells and compositions comprising thereof of the present invention are provided indirectly to the organ of interest, for example, by administration into the circulatory system (e.g., the tumor vasculature). Expansion and differentiation agents can be provided prior to, during or after administration of cells and compositions to increase production of T cells in vitro or in vivo.

T cells and compositions comprising thereof of the present invention can be administered in any physiologically acceptable vehicle, normally intravascularly, although they may also be introduced into bone or other convenient site where the cells may find an appropriate site for regeneration and differentiation (e.g., thymus). Usually, at least $1\times10^5$ cells will be administered, eventually reaching $1\times10^{10}$ or more. A cell population comprising T cells can comprise a purified population of cells. Those skilled in the art can readily determine the percentage of T cells in a population using various well-known methods, such as fluorescence activated cell sorting (FACS). Preferable ranges of purity in populations comprising genetically modified immunoresponsive cells are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%. Dosages can be readily adjusted by those skilled in the art (e.g., a decrease in purity may require an increase in dosage). The cells can be introduced by injection, catheter, or the like. If desired, factors can also be included, including, but not limited to, interleukins, e.g. IL-2, IL-3, IL 6, IL-11, IL-7, IL-12, IL-15, IL-21, as well as the other interleukins, the colony stimulating factors, such as G-, M- and GM-CSF, interferons, e.g. gamma.-interferon and erythropoietin.

Compositions of the invention include pharmaceutical compositions comprising T cells derived from CAR-expressing T-PSCs and a pharmaceutically acceptable carrier. Administration can be autologous or non-autologous. For example, T cells and compositions comprising thereof can be obtained from one subject, and administered to the same subject or a different, compatible subject. Peripheral blood derived T cells of the present invention or their progeny (e.g., in vivo, ex vivo or in vitro derived) can be administered via localized injection, including catheter administration, systemic injection, localized injection, intravenous injection, or parenteral administration. When administering a therapeutic composition of the present invention (e.g., a pharmaceutical composition comprising T cells derived from CAR-expressing T-PSCs), it will generally be formulated in a unit dosage injectable form (solution, suspension, emulsion).

IX. Formulations

Cell populations comprising T cells derived from CAR-expressing T-PSCs and compositions comprising thereof of the present invention can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions comprising T cells derived from CAR-expressing T-PSCs of the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the present invention, however, any vehicle, diluent, or additive used would have to be compatible with the T cells derived from CAR-expressing T-iPSCs of the present invention.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the T cells as describe in the present invention. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of T cells of the present invention is the quantity of cells necessary to achieve an optimal effect. The quantity of cells to be administered will vary for the subject being treated. In a one embodiment, between $10^4$ to $10^{10}$ between $10^5$ to $10^9$ or between $10^6$ and $10^8$ T cells of the present invention are administered to a human subject. More effective cells may be administered in even smaller numbers. In some embodiments, at least about $1\times10^8$, $2\times10^8$, $3\times10^8$, $4\times10^8$, and $5\times10^8$ T cells of the present invention are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the invention. Typically, any additives (in addition to the active cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

X. Methods of Treatment

The present invention provides methods for treating neoplasia in a subject. The present invention also provides methods for treating a pathogen infection or other infectious disease in a subject, such as an immunocompromised human subject. The methods comprise administering T cells derived from CAR-expressing T-PSCs of the present invention in an amount effective to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

An "effective amount" (or, "therapeutically effective amount") is an amount sufficient to effect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the antigen-binding fragment administered.

For adoptive immunotherapy using antigen-specific T cells, cell doses in the range of $10^6$-$10^{10}$ (e.g., $10^9$) are typically infused. Upon administration of the T cells into the subject and subsequent differentiation, T cells are induced that are specifically directed against one specific antigen. "Induction" of T cells can include inactivation of antigen-specific T cells such as by deletion or anergy. Inactivation is particularly useful to establish or reestablish tolerance such as in autoimmune disorders. The T cells of the present invention can be administered by any methods known in the art, including, but not limited to, intravenous administration, subcutaneous administration, intranodal administration, intratumoral administration, intrathecal administration, intrapleural administration, intraperitoneal administration, and direct administration to the thymus.

The invention provides methods for increasing an immune response in a subject in need thereof. In one embodiment, the invention provides methods for treating or preventing a neoplasia in a subject. The invention provides therapies that are particularly useful for the treatment of subjects having blood cancers (e.g. leukemias, lymphomas, and myelomas) or ovarian cancer, that are not amenable to conventional therapeutic interventions. Suitable human subjects for therapy typically comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in this invention is administered to these subjects to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group." These are individuals who have had a history of neoplasia, but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor has invaded neighboring tissues, or who show involvement of lymph nodes.

Another group have a genetic predisposition to neoplasia but have not yet evidenced clinical signs of neoplasia. For instance, women testing positive for a genetic mutation associated with breast cancer, but still of childbearing age, can wish to receive one or more of the antigen-binding fragments described herein in treatment prophylactically to prevent the occurrence of neoplasia until it is suitable to perform preventive surgery.

Human neoplasia subjects having any of the following neoplasias: glioblastoma, melanoma, neuroblastom a, adenocarcinoma, glioma, soft tissue sarcoma, and various carcinomas (including prostate and small cell lung cancer) are especially appropriate subjects. Suitable carcinomas further include any known in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolar carcinoma, epithelial adenocarcinoma, and liver metastases thereof, lymphangiosarcoma, lymphangioendothelio sarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bile duct carcinoma, choriocarcinoma, seminoma, embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, and heavy chain disease, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence. In some embodiments, the subjects are immune-deficient patients, such as HIV-infected or highly immunosuppressed patients with malignancies, where autologous T-cell isolation and expansion is problematic or impossible. In some embodiments, the subjects have failed isolation of autologous tumor-infiltrating T lymphocytes. In some embodiments, the patients have acute leukemia and have relapsed after allogeneic hematopoietic cell transplantation, for whom the use of allogeneic donor lymphocyte infusions (DLI) is problematic. Thus, the methods can provide an additional option for patients who do not respond to DLI or for whom DLI use is not indicated due to high risk for graft-versus-host disease.

Accordingly, the invention provides a method of treating or preventing a neoplasia in a subject, the method comprising administering to the subject an effective amount of the T cells derived from CAR-expressing T-iPSCs of the present invention. Examples of neoplasia that can be treated or prevented by administration of the T cells of the present invention include, but are not limited to, blood cancers (e.g. leukemias, lymphomas, and myelomas), ovarian cancer, sarcoma, and acute myeloid leukemia (AML), prostate cancer, breast cancer, bladder cancer, brain cancer, colon cancer, intestinal cancer, liver cancer, lung cancer, pancreatic cancer, prostate cancer, skin cancer, stomach cancer, glioblastoma, and throat cancer. In another embodiment, the tumor antigen is one or more of carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, an antigen of a cytomegalovirus (CMV) infected cell (e.g., a cell surface antigen), epithelial glycoprotein2 (EGP 2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), melanoma antigen family A, 1 (MAGE-AI), Mucin 16 (Muc-16), Mucin 1 (Muc-1), Mesothelin (MSLN), NKG2D ligands, cancer-testis antigen NY-ESO-1, on cofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), or Wilms tumor protein (WT-1).

In other embodiments, the invention provides methods for treating subjects with a pathogen infection (e.g., viral infection, bacterial infection, fungal infection, parasite infection, or protozoal infection). The invention is particularly useful for enhancing an immune response in an immunocompromised subject. Exemplary viral infections susceptible to treatment using a method of the invention include, but are not limited to, Cytomegalovirus (CMV), Epstein Barr Virus (EBV), Human Immunodeficiency Virus (HIV), and influenza virus infections. Accordingly, the invention provides a method of treating or preventing a pathogen infection in a subject, the method comprising administering an effective amount of the CAR-expressing T cells of the present invention.

Several steps can be taken to avert or minimize the risks of immunological complications in the context of an "off-the-shelf" allogeneic CAR-T-PSC-T therapy. Generation of "off-the-shelf" T cells for administration to multiple recipients can be achieved by prevention of allo-rejection of adoptively transferred CAR-T-PSC T cells. For example, The alloreactivity of T-PSC-derived T cells, which express an endogenous TCR (FIG. 1A), can be minimized or pre-empted by generating PSCs from common HLA haplotypes to ensure their histocompatibility with matched unrelated recipients) or homozygous HLA haplotypes (Turner at al Cell Stem Cell 2013 and Stacey et al Cell Stem Cell 2013), and/or by repressing HLA expression on the CAR-T-PSC-derived T cells, e.g., knocking out the HLA transcription factor and/or b2-microglobulin, e.g., by using zinc-finger nucleases, meganucleases, TALENs or CRISPR. Rejection of CAR-T-PSC-derived T cells from the recipient's T lymphocytes can be prevented by genetic modification of the T-PSCs to express ligands for immunoregulatory T cell receptors, including, but not limited to, PD-L1, CD48, TNFRSF14. Furthermore, rejection of CAR-T-PSC-derived T cells from the recipient's NK cells can be prevented by genetic modification of the T-PSCs to express the non-classical class I, e.g., HLA-G. Additionally or alternatively, generation of "off-the-shelf" T cells for administration to multiple recipients can be achieved by prevention of graft versus-host disease (GvHD). For example, prevention of GvHD can be achieved by selection of a desirable endogenous TCR, e.g, by generating T-PSCs from virus-specific T cells, which due to their recognition of a pathogen-derived antigen, are less likely to cause GvHD. The already rearranged TCR is already directed against viral antigens, with which large population has been infected (e.g., EBV, CMV), and thus, there is little or no risk for GvHD reaction after administration of the product. There are already well-characterized banks of EBV- and CMV-specific T cells, which can be used for the generation of such PSCs. In addition, prevention of GvHD can be achieved by eliminating the expression of the endogenous TCR by disruption of the TRAC gene, e.g., by using zinc-finger nucleases, meganucleases, TALENs or CRISPR. Furthermore, prevention of GvHD can be achieved by preventing the surface expression of TCR, e.g., by knocking out (e.g., by zinc-finger nucleases, meganucleases, TALENs or CRISPR) or knocking down (e.g., with shRNAs) of the CD3 gene expression. The risk of insertional oncogenesis secondary to gene transfer can be decreased by integrating the CAR cDNA and other genes, such as suicide genes and noninvasive imaging reporters at genomic safe harbor sites. Suitable suicide genes include, but are not limited to, Herpes simplex virus thymidine kinase (hsv-tk) and inducible Caspase 9 Suicide gene (iCasp-9).

XI. Kits

The invention provides kits for the treatment or prevention of a neoplasia, pathogen infection, immune disorder or allogeneic transplant. In one embodiment, the kit includes a therapeutic or prophylactic composition containing an effective amount of T cells derived from CAR-expressing T-PSCs in unit dosage form. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the T cells is provided together with instructions for administering the T cells to a subject having or at risk of developing a neoplasia, pathogen infection, immune disorder or allogeneic transplant. The instructions generally include information about the use of the composition for the treatment or prevention of neoplasia, pathogen infection, immune disorder or allogeneic transplant. In other embodiments, the instructions include at least one of the following: description of the therapeutic agent; dosage schedule and administration for treatment or prevention of a neoplasia, pathogen infection, immune disorder or allogeneic transplant or symptoms thereof; precautions; warnings; indications; counter-indications; over-dosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The following examples serve to illustrate certain embodiments and aspects of the present invention and are not to be construed as limiting the scope thereof. In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); pg (picograms); L and (liters); ml (milliliters); μl (microliters); cm (centimeters); mm (millimeters); μm (micrometers); nm (nanometers); U (units); min (minute); s and sec (second); deg (degree); pen (penicillin), strep (streptomycin) and ° C. (degrees Centigrade/Celsius).

Example 1—Generation of Tumor-Targeted Human T Lymphocytes from Induced Pluripotent Stem Cells for Cancer Therapy 1. Summary This Example provides exemplary cell culture methods for use in producing exemplary cells of the present invention. These cell culture systems result in differentiation when using ES or iPS cells as starting populations. When peripheral blood T cells are used as a starting population this cell culture system additionally dedifferentiates T cells to iPS like cells that are then differentiated into T like cells for use with CARs of the present inventions.

Progress in adoptive T-cell therapy for cancer and infectious diseases (1, 2) is hampered by the lack of readily available, antigen-specific, human T lymphocytes. Pluripotent stem cells could provide an unlimited source of T lymphocytes, but the therapeutic potential of human pluripotent stem cell-derived lymphoid cells generated to date remains uncertain (3-6). As shown in this Example, induced pluripotent stem cell (iPSC) was combined with chimeric antigen receptor (CAR) technologies to generate human T cells targeted to CD19, an antigen expressed by malignant B cells, in tissue culture (7, 8). These iPSC-derived, CAR-expressing T cells display a phenotype resembling that of innate γδ T cells. Similar to CAR-transduced, peripheral blood γδ T cells, the iPSC-derived T cells potently inhibit tumor growth in a xenograft model. This approach of generating therapeutic human T cells 'in the dish' may be useful for cancer immunotherapy and other medical applications.

2. Introduction

Current approaches to adoptive T-cell therapy require the labor-intensive generation of T-cell lines from carefully selected donors or the genetic engineering of autologous T cells from each individual patient, hindering the facile and broad use of T cells with pre-determined antigen specificity. Having rapid access to unlimited antigen-specific T lymphocytes with optimized therapeutic features would greatly advance the scope and delivery of T-cell therapies. Previous studies support the feasibility of generating T lymphocytes from human embryonic stem cells (ESCs) and iPSCs in vitro, although the yield of lymphoid cells has been low and their nature only partially defined (3, 4). More specifically, the functional characterization of T cells derived from ESCs and iPSCs is complicated by not knowing their antigen specificity and HLA restriction. For example, T cells generated in vitro from ESCs or iPSCs have an unpredictable T-cell receptor (TCR) repertoire because TCR gene rearrangements are random and the cells are positively selected by unclear mechanisms during their in vitro differentiation (3). This limitation can be circumvented by using iPSCs bearing a rearranged endogenous TCR of known antigen specificity (5, 6). Unfortunately, this approach requires laborious cloning of antigen-specific T cells and is limited to antigens for which patient-specific T cells can be detected. Furthermore, as TCRs recognize antigens presented by specific HLA molecules, the clinical use of T cells that recognize antigen through an endogenous TCR is constrained by the need to match their specificity to the HLA of the recipient patient.

Genetic engineering of T lymphocytes to express CARs has recently emerged as a promising approach to rapidly generate tumor-targeted T cells endowed with enhanced anti-tumor properties (8). For example, CARs redirect T-cell specificity in HLA-independent fashion, thereby eliminating the need to consider HLA restriction and overcoming some tumor escape mechanisms (8). It was previously demonstrated that human T cells expressing a CAR targeted to the CD19 antigen, which is expressed on the vast majority of leukemias and lymphomas, can eradicate B-cell malignancies in mice (9). Importantly, second-generation CARs, combining both activation and co-stimulatory signaling domains, enhanced T-cell expansion and in vivo persistence (8, 10). It has been demonstrated in clinical trials that second-generation CD19 CAR-modified T cells efficiently induce complete remissions in patients with acute or chronic lymphoblastic leukemias (11-14).

It was hypothesized that genetic engineering of iPSCs with second-generation CARs would be an efficient strategy to concomitantly harness the unlimited availability of iPSCs and to generate phenotypically defined, functional and expandable T cells that are genetically targeted to a tumor antigen of interest (FIG. 1A) (8).

3. Methods and Materials 3.1. Generation of 1928z-T-iPSC

Figure 4D:
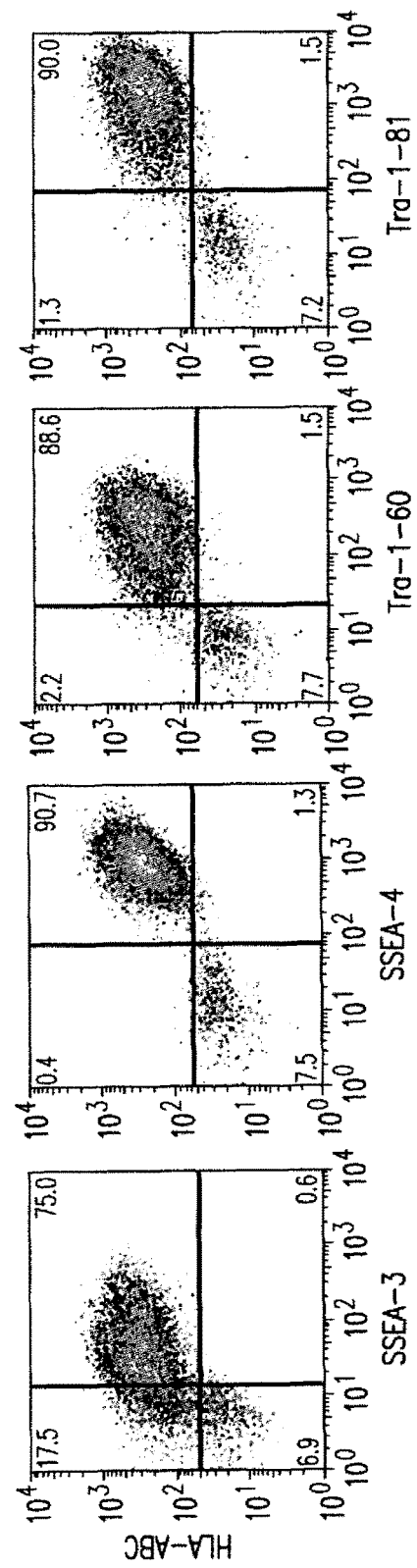
Figure 4G:
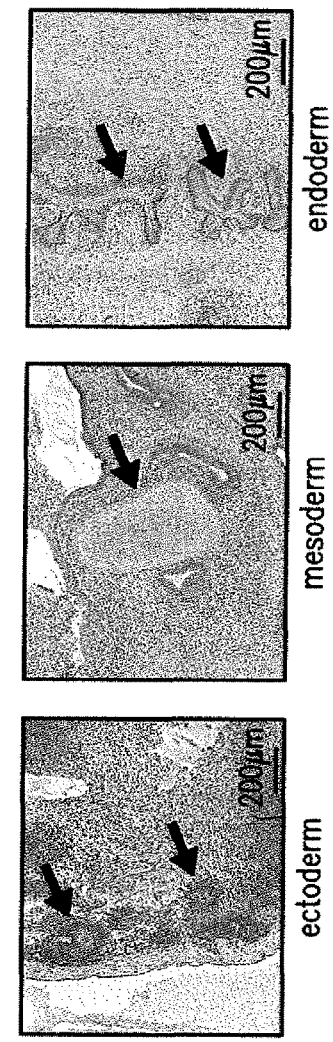
Figure 4E:
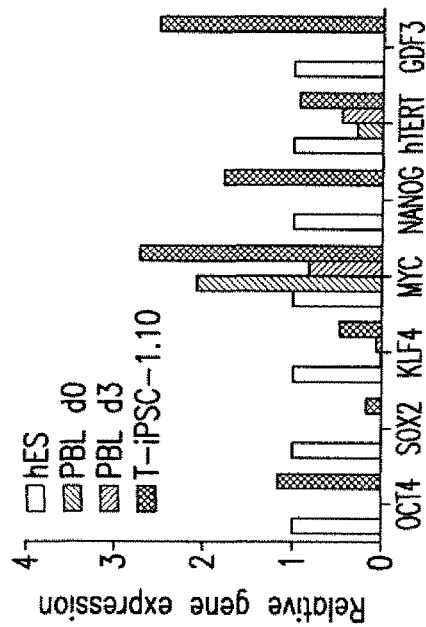
Figure 4F:
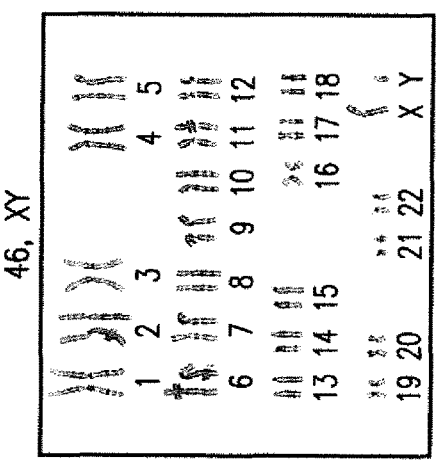

Peripheral blood lymphocytes (PBL) were collected from a volunteer donor after informed consent was obtained. PBLs were activated with phytohaemagglutinin (PHA, 2 g/ml) and transduced with two tri-cistronic excisable Moloney murine leukemia virus-based (SFG) retroviral vectors, each one encoding reprogramming factors and a different fluorescent marker (f-Citrine-P2A-cMYC-E2A-SOX2 and f-vexGFP-P2A-OCT4-T2A-KLF4) (FIG. 4A). The Citrine-P2A-cMYC-E2A-SOX2 sequence and vexGFP-P2A-OCT4-T2A-KLF4 were constructed by overlapping PCR fragments and introduced in the NcoI and BamHI sites of an SFG retroviral vector (see, Riviere et al PNAS 1995 for compositions and methods of constructing an SFG vector). A wpre element was introduced after the transgenes and before the 3'LTR. A loxP site was introduced in the 3'LTR, so that the vector can be excised by transient expression of Cre recombinase through an integrase-deficient lentiviral vector (IDLV) (43). A loxP site was introduced in the 3'LTR, so that the vector was excised by transient expression of Cre recombinase through an integrase-deficient lentiviral vector (IDLV).

An exemplary nucleic acid sequence for encoding reprogramming factors MYC and SOX-2, wherein an exemplary marker is Citrine: SFG-fCMS (f-Citrine-P2A-cMYC-E2A-SOX2) which includes:

[SEQ ID NO: 18]

```
atggtgagcaagggcgaggagctgttcaccggggtggtgcccatcctggtcgagctggacggcgacgtaaacggccacaag ttcagcgtgtccggcgagggcgagggcgatgcacctacggcaagctgaccctgaagttcatctgcaccaccggcaagctgc ccgtgccctggcccaccctcgtgaccacctcggctacggcctgatgtgcttcgcccgctaccccgaccacatgaagcagcac gacttcttcaagtccaccatgcccgaaggctacgtccaggagcgcaccatcttcttcaaggacgacggcaactacaagacccg cgccgaggtgaagttcgagggcgacaccctggtgaaccgcatcgagctgaagggcatcgacttcaaggaggacggcaacat cctggggcacaagctggagtacaactacaacagccacaacgtctatatcatggccgacaagcagaagaacggcatcaaggtg aacttcaagatccgccacaacatcgaggacggcagcgtgcagctcgccgaccactaccagcagaacacccccatcggcgac ggccccgtgctgctgcccgacaaccactacctgagctaccagtccgccctgagcaaagacccccaacgagaagcgcgatcaca tggtcctgctggagttcgtgaccgccgccgggatcactctcggcatggacgagctgtacaag
```
GGATCTGGAGCAA
CAAACTTCTCACTACTCAAACAAGCAGGTGACGTGGAGGAGAATCCCGGCCC
T
```
atgcccctcaacgttagcttcaccaacaggaactatgacctcgactacgactcggtgcagccgtatttctactgcgacg aggaggagaacttctaccagcagcagcagcagagcgagctgcagcccccggcgcccagcgaggatatctggaagaa attcgagctgctgcccaccccgcccctgtccctagccgccgctccgggctctgctcgccctcctacgttgcggtcacacc cttctcccttcggggagacaacgacggcggtggcgggagcttctccacggccgaccagctggagatggtgaccgagctg ctgggaggagacatggtgaaccagagtttcatctgcgacccggacgacgagaccttcatcaaaaacatcatcatccagg actgtatgtggagcggcttctcggccgccgccaagctcgtctcagagaagctggcctcctaccaggctgcgcgcaaaga cagcggcagcccgaacccgcccgcggccacagcgcgtgctccacctccagcttgtacctgcaggatctgagcgccgcc gcctcagagtgcatcgaccctcggtggtcttccctaccctctcaacgacagcagctcgcccaagtcctgcgcctcgca agactccagcgccttctctccgtcctcggattctctgctctcctcgacggagtcctccccgcagggcagcccgagcccct ggtgaccatgaggagacaccgcccaccaccagcagcgactctgaggaggaacaagaagatgaggaagaaatcgat gttgtttctgtggaaaagaggcaggctcctggcaaaaggtcagagtctggatcaccttctgaggaggccacagcaaac ctcctcacagcccactggtcctcaagaggtgccacgtctccacacatcagcacaactacgcagcgcctccctccactcgg aaggactatcctgagccaagagggtcaagttggacagtgtcagagtcctgagacagatcagcaacaaccgaaaatgc accagccccaggtcctcggacaccgaggagaatgtcaagaggcgaacacacaacgtcttggacgccagaggagga acgagctaaaacggagcttttttgccctgcgtgaccagatcccggagttggaaaacaatgaaaaggccccaaggtagt
```

-continued tatccttaaaaaagccacagcatacatcctgtccgtccaagcagaggagcaaaagctcatttctgaagaggacttgttgc ggaaacgacgagaacagttgaaacacaaacttgaacagctacggaactattgcgGGATCTGGACAATG

TACTAACTACGCTTTGTTGAAACTCGCTGGCGATGTTGAAAGTAACCCCGGTC

CC*atgtacaacatgatggagacggagctgaagccgccgggcagcagcaaacttcggggggcggcggcggcaactcc*

*accgcggcggcggccggcggcaaccagaaaaacagcccggaccgcgtcaagcggcccatgaatgccttcatggtgtgg*

*tcccgcgggcagcggcgcaagatggcccaggagaacccaagatgcacaactcggagatcagcaagcgcctgggcgc*

*cgagtggaaactttgtcggagacggagaagcggccgttcatcgacgaggctaagcggctgcgagcgctgcacatgaag*

*gagcaccggattataaataccggccccggcggaaaaccaagacgctcatgaagaaggataagtacacgctgcccggc*

*gggctgctggccccggcggcaatagcatggcgagcggggtcggggtgggcgccggcctgggcgcgggcgtgaaccag*

*cgcatggacagttacgcgcacatgaacggctggagcaacggcagctacagcatgatgcaggaccagctgggctacccgc*

*agcacccgggcctcaatgcgcacggcgcagcgcagatgcagcccatgcaccgctacgacgtgagcgccctgcagtaca*

*actccatgaccagctcgcagacctacatgaacggctcgcccacctacagcatgtcctactcgcagcagggcacccctggca*

*tggctcttggctccatgggttcggtggtcaagtccgaggccagctccagcccccctgtggttacctcttcctcccactccaggg*

*cgccctgccaggccggggacctccgggacatgatcagcatgtataccccggcgccgaggtgccggaacccgccgcccc*

*cagcagacttcacatgtcccagcactaccagagcggcccggtgcccggcacggccattaacggcacactgcccctacac*

*acatgtga.*

This annotated vector sequence shows an exemplary nucleic acid sequence of: underlined=fluorescent marker; Capital letters=2A peptides; bold=first reprogramming gene; italic=second reprogramming gene.

An exemplary nucleic acid sequence for encoding reprogramming factors OCT4 and OCT, wherein an exemplary marker is vexGFP: SFG-GOK (f-vexGFP-P2A-OCT4-T2A-KLF4):

[SEQ ID NO: 19]

<u>atggtgagcaagggcgaggagctgttcaccggggtggtgcccatcctggtcgagctggacggcgacgtaaacggccacaag</u>

<u>ttcagcgtgtccggcgagggcgagggcgatgccacctacggcaagctgaccctgaagttcatctgcaccaccggcaagctgc</u>

<u>ccgtgccctggcccaccctcgtgaccacctgagctacggcgtgcagtgcttcagccgctaccccgaccacatgaagcagcac</u>

<u>gacttcttcaagtccgccatgcccgaaggctacgtccapagcgcaccatcagcttcaaggacgacggcaactacaagacccg</u>

<u>cgccgaggtgaagttcgagggcgacaccaggtgaaccgcatcgagctgaagggcatcgacttcaaggaggacggcaacat</u>

<u>cctggggcacaagctggagtacaactacaacagccacaacgtctatatcacggccgacaagcagaagaacggcatcaaggc</u>

<u>gaacttcaagatccgccacaacatcgaggacggcagcgtgcaptcgccgaccactaccagcagaacacccccatcggcga</u>

<u>cggcccgtgctgagcccgacaaccactacctattcatccagtccgccctgagcaaagacccaacgagaagcgcgatcac</u>

<u>atggtcctgcggagttcgtgaccgccgccgggatcactcacggcatggacgagctgtacaag</u>GGATCTGGAGCA

ACAAACTTCTCACTACTCAAACAAGCAGGTGACGTGGAGGAGAATCCCGGCC

CT*atggcgggacacctggcttcggatttcgccttctcgcccctccaggtggtggaggtgatgggccaggggggccgg*

*agccgggctgggttgatcctcggacctggctaagcttccaaggccctcctggagggccaggaatcgggccgggggttgg*

*gccaggctctgaggtgtgggggattccccatgccccgccgtatgagttctgtgggggatggcgtactgtgggcccc*

*aggttggagtggggctagtgccccaaggcggcttggagacctctcagcctgagggTgaagcaggagtcggggtggag*

*agcaactccgatggggcctccccggagccctgcaccgtcaccctggtgccgtgaagctggagaaggagaagctggag*

*caaaacccggaggagtcccaggacatcaaagctctgcagaaagaactcgagcaatttgccaagctcctgaagcagaa*

*gaggatcaccctgggatatacacaggccgatgtggggctcaccctggggttctatttgggaaggtattcagccaaacg*

*accatctgccgctttgaggctctgcagcttagcttcaagaacatgtgtaagctgcggcccttgctgcagaagtgggtgga*

*ggaagctgacaacaatgaaaatcttcaggagatatgcaaagcagaaaccctcgtgcaggcccgaaagagaaagcga*

*accagtatcgagaaccgagtgagaggcaacctggagaatttgttcctgcagtgcccgaaacccacactgcagcagatc*

-continued

```
agccacatcgcccagcagcttgggctcgagaaggatgtggtccgagtgtggttctgtaaccggcgccagaagggcaag cgatcaagcagcgactatgcacaacgagaggattttgaggctgctgggtctcctttctcaggggaccagtgtcctttcct ctggccccagggcccatttggtacccaggctatgggagccctcacttcactgcactgtactcctcggtccctttcctg aggggaagcctttcccctgtctctgtcaccactctgggctctcccatgcattcaaac
```
GGATCTGGAGAGGG CAGAGGAAGTCTTCTAACATGCGGTGACGTGGAGGAGAATCCCGGCCCC*atggc*

*tgtcagcgacgcgctgctcccatctttctccacgttcgcgtctggcccggcgggaagggagaagacactgcgtcaagcaggt*

*gccccgaataaccgctggcgggaggagctctcccacatgaagcgacttcccccagtgcttcccggccgccctatgacctg*

*gcggcggcgaccgtggccacagacctggagagcggcggagccggtgcggcttgcggcggtagcaacctggcgcccta*

*cctcggagagagaccgaggagttcaacgatctcctggacctggactttattctctccaattcgctgacccatcctccggagtc*

*agtggccgccaccgtgtcctcgtcagcgtcagcctcctcttcgtcgtcgccgtcgagcagcggccctgccagcgcgcctcc*

*acctgcagcttcacctatccgatccgggccgggaacgacccgggcgtggcgccgggcggcacgggcggaggcctcctct*

*atggcagggagtccgctcccccctccgacggctcccttcaacctggcggacatcaacgacgtgagcccctcgggcggcttcg*

*tggccgagctcctgcggccagaattggaccgggtgtacattccgccgcagcagccgcagccgccaggtggcgggctgatg*

*ggcaagttcgtgctgaaggcgtcgctgagcgccctggcagcgagtacggcagcccgtcggtcatcagcgtcagcaaagg*

*cagccctgacggcagccacccggtggtggtggcgccctacaacggcgggccgccgcgcacgtgccccaagatcaagca*

*ggaggcggtctcttcgtgcacccacttgggcgctggaccccctctcagcaatggccaccggccggctgcacacgacttcccc*

*ctggggcggcagctcccagcaggactacccgaccctgggtcttgaggaagtgctgagcagcagggactgtcaccctgc*

*cctgccgcttcctcccggcttccatccccacccggggcccaattacccatccttcctgcccgatcagatgcagccgcaagtcc*

*cgccgctccattaccaagagctcatgccacccggttcctgcatgccagaggagcccaagccaaagaggggaagacgatc*

*gtggcccccgaaaaggaccgccacccacacttgtgattacgcgggctgcggcaaaacctacacaaagagttcccatctca*

*aggcacacctgcgaacccacacaggtgagaaaccttaccactgtgactgggacggctgtggatggaaattcgcccgctca*

*gatgaactgaccaggcactaccgtaaacacacggggcaccgcccgttccagtgccaaaaatgcgaccgagcattttccag*

*gtcggaccacctcgccttacacatgaagaggcatttttaa.*

This annotated vector sequence shows an exemplary nucleic acid sequence of: underlined=fluorescent marker; Capital letters=2A peptides; bold=first reprogramming gene; italic=second reprogramming gene.

Figure 6A:
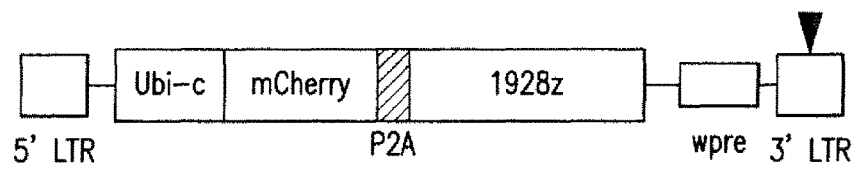
FIGS. 6A-6C show generation of 1928z CAR expressing T-iPSCs. (A) Schematic representation of the lentiviral vector encoding the 1928z CAR and the mCherry fluorescent marker linked with a P2A peptide. LTR: long terminal repeat, Ubi-c: Ubiquitin-C promoter, wpre: woodchuck hepatitis virus posttranscriptional regulatory element. (B) T-iPSC-1.10 line transduced with the mCherry-P2A-1928z lentiviral vector (1928z-T-iPSC) as seen under a fluorescent microscope. Top image: bright field, bottom image: epifluorescence. Scale bar, 100 µM. (C) Expression mCherry and the CAR in 1928z-T-iPSCs assessed by flow cytometry. Surface expression of the CAR was determined after staining with a goat-anti-mouse IgG F(ab')2 antibody that binds to the murine derived extracellular domain of the CAR.

Transduced cells were seeded on MEF feeder cells and cultured in T-cell medium (RPMI-1640 supplemented with 10% FBS, 2 mM 1-glutamine, 100 U/ml penicillin and 100 ng/ml streptomycin). The medium was changed to human ESC medium (DMEM/F12 with 20% of knockout serum replacement, 1 mM 1-glutamine, 1% nonessential amino acids, 10 mM 2-mercaptoethanol and 8 ng/ml basic fibroblast growth factor (bFGF)) on day 5 after transduction and was then refreshed daily. T-iPSC colonies appeared at ~22-25 days after transduction. Clone T-iPSC-1.10 was stably transduced with a lentiviral vector encoding 19-28z, a second-generation CAR, and a fluorescent marker (mCherry) linked by a 2A peptide (FIG. 6A). The 1928z-T-iPSC line was established after sorting for high expression of the mCherry marker. All T-iPSC lines were maintained in culture on MEF feeder cells with human ESC medium and passaged every 3 to 4 days. T-iPSC lines were tested for mycoplasma contamination every 2 months.

3.2. Characterization and Assessment of Pluripotency of T-iPSCs.

To determine the reprogramming vectors' copy numbers (VCN), isolated genomic DNA was isolated from the T-iPSC lines and multiplex quantitative PCR (qPCR) using sets of primers and probes specific for the SFG vector and for the human albumin gene (Table 1) was performed. To determine absolute VCN, a standard curve was generated using serial dilutions of a plasmid containing both SFG vector and albumin gene amplicons. Reactions were carried out in triplicate in an ABI 7500 detection system (Applied Biosystems).

TABLE 1

List of Oligonucleotides used for vector copy number qPCR

| | |
|---|---|
| SEG forward | 5'-AGAACCTAGAACCTCGCTGGA-3' (SEQ ID NO: 20) |
| SEG reverse | 5'-CTGCGATGCCGTTCTACTTTG-3' (SEQ ID NO: 21) |
| hALB forward | 5'-TGAAACATACGTTCCCAAAGAGTTT-3' (SEQ ID NO: 22) |
| hALB reverse | 5'-CTGTCCTTCTCAGAAAGTGTGCATAT-3' (SEQ ID NO: 23) |
| SEG probe | 5' FAM-AGGACCTTACACAGTCCTGCTGAC-3' (SEQ ID NO: 24) |
| hALB probe | 5' VIC-TGCTGAAACATTCACCTTCCATGCAGA-TAMRA-3' (SEQ ID NO: 25) |

For assessment of expression of endogenous pluripotency genes, total mRNA from T-iPSC was isolated with Trizol (Invitrogen). Reverse transcription was performed with Superscript III (Invitrogen) and qRT-PCR was performed with previously described primers using SYBR Green (38). Reactions were carried out in duplicate in an ABI PRISM 7500 Sequence Detection System (Applied Biosystems). Expression was calculated by relative quantification using the DDCt method with GAPDH as endogenous control.

For flow cytometric analysis, T-iPSCs were stained with the following fluorophore-conjugated antibodies: SSEA-3-AlexaFluor647 (MC-631) purchased from Biolegend, SSEA-4-AlexaFluor647 (MC813-70), Tra-1-81-AlexaFluor647 (TRA-1-81), Tra-1-60-AlexaFluor647 (TRA-1-60) and HLA-ABC-PE (Cat #555553) purchased from BD Biosciences. All flow cytometry analysis was done on a LSRII cytometer (BD Biosciences) and analyzed using FlowJo software, Ver. 9.5.2 (TreeStar).

For teratoma formation assays, undifferentiated T-iPSCs were suspended in human ESC medium containing 10 mM of the Rho-associated kinase (Rock) inhibitor Y-27632 (Tocris). Approximately $2 \times 10^6$ cells were injected subcutaneously into 6- to 12-week-old female NOD-SCID IL2R$\gamma$c$^{null}$ mice obtained from the MSKCC Mouse Genetics Core facility. Five to six weeks later, teratomas were surgically dissected and fixed in 4% formaldehyde. Paraffin-embedded samples were stained with hematoxylin and eosin for histological analysis.

For karyotyping, standard G-banding analysis was done at the MSKCC molecular cytogenetics core facility. Chromosome analysis was done on a minimum of 12 4,6-diamidino-2-phenylindole (DAPI)-banded metaphases.

For the assessment of silencing of the reprogramming vectors, qRT-PCR was done using primers and probes that detect GFP-derivative (vexGFP and mCitrine) transcripts as previously described (38). Reactions were carried out in duplicate in an ABI PRISM 7500 Sequence Detection System (Applied Biosystems). Expression was calculated by relative quantification using the DDCt method with GAPDH as endogenous control.

3.3 TCR $\beta$ and $\gamma$ Chain Rearrangement

Genomic DNA was isolated from T-iPSCs and 1928z-T-iPSC-T cells using Qiagen DNeasy Blood and Tissue kit (Qiagen). PCR was performed using multiplex primer kits (Invivoscribe Technologies, San Diego, Calif.) specific for a majority of clonal TCR $\beta$ and $\gamma$ chain rearrangements. Capillary electrophoresis and PCR product fragment analysis was performed at MSKCC Genomic's Core Facility using an ABI 3730 DNA analyzer. Data were analyzed using Peak Scanner software (ABI, Foster City, Calif.).

3.4 T-Cell Differentiation from 1928z-T-iPSCs and Expansion of 1928z-T-iPSC-T Cells For the differentiation of 1928z-T-iPSCs to hematopoietic precursors, an optimized serum- and feeder-free in vitro differentiation protocol was used. Briefly, undifferentiated T-iPSC colonies were treated with dispase (Worthington) for 6 min and transferred to low-attachment plates to allow for the formation of embryoid bodies (EBs) in embryoid body differentiation medium (StemPro-34, Invitrogen, with 2 mM l-glutamine, 1% nonessential amino acids, 10 mM 2-mercaptoethanol, 100 U/ml penicillin and 100 ng/ml streptomycin and 50 mg/ml ascorbic acid). The formation of embryoid bodies was facilitated by an overnight incubation in the presence of 30 ng/ml of hBMP-4, embryoid bodies were then cultured with BMP-4 and hbFGF (5 ng/ml) until day 4 to allow for mesoderm induction. Next, hematopoietic specification and expansion was achieved in the presence of hVEGF (20 ng/ml) and a cocktail of hematopoietic cytokines (hSCF 100 ng/ml, hFlt3L 20 ng/ml, hIL-3 20 ng/ml and bFGF 5 ng/ml) as indicated. Day 10 embryoid bodies containing hematopoietic progenitor cells were dissociated by treatment with Accutase for 20 min and single cells were then seeded on OP9-DL1 monolayers to allow for their T-lymphoid differentiation in OP9 medium (a-MEM with 20% FBS, 2 mM l-glutamine, 1% nonessential amino acids, 10 mM 2-mercaptoethanol, 100 U/ml penicillin and 100 ng/ml streptomycin and 50 mg/ml ascorbic acid) supplemented with SCF 10 ng/ml, IL-7 5 ng/ml and Flt3L 10 ng/ml (39). For the stimulation and expansion of 1928z-T-iPSC-T cells, we used previously described CD19-expressing 3T3 cells as artificial antigen presenting cells (3T3-CD19) (9, 40). The generated 1928z-T-iPSC-T cells were seeded on a monolayer of irradiated 3T3-CD19 in a 3:1 E/T ratio in T-cell medium with IL-7 (10 ng/ml) and IL-15 (10 ng/ml). All recombinant factors were purchased from R&D Systems (Minneapolis).

3.5 Flow Cytometric Analysis

The following conjugated antibodies were used for flow cytometric phenotyping and analysis: CD34-PECy.7 (8012), CD43-FITC (1G10), CD7-V450 (MT701), CD8$\beta$-PE (2ST8.5H7), CD69-PECy.7 (FN50), CD161-FITC (DX12), CD16-PerCPCy5.5 (3G8), TCR$\gamma\delta$-FITC (11F2), CD122-FITC (TU27), CD94-PE (HP-3D9) purchased from BD Biosciences, CD3-PE/FITC/Pacific Blue (UCTH1), CD5-PE (5D7), CD4-PECy.7 (S3.5), CD8$\alpha$-PE/FITC (3B5), CD25-APC (3G10), CD62L-PE (Dreg-56), CD27-APC (0323), CD28-PE (10F3), goat-anti-mouse-AlexaFluor647 purchased from Invitrogen, TCR$\alpha\beta$-APC (IP26), CD56-PECy.7 (CMSSB) and CD45RA-PerCPCy5.5 (HI100) purchased from eBioscience, NKp44-PE (P44-8), NKp46-PE (9E2), NKG2DAPC (1D11), CD158a/h-PE (HP-MA4), CD158b-PE (OX27) purchased from BioLegend, PLZF-APC (20102) and CCR7-FITC (150503) purchased from R&D. All antibodies were used in a 1:20 dilution. Dead cells were excluded from analysis in all experiments by staining with DAPI. All flow cytometry analysis was done on a LSRII cytometer (BD Biosciences) and analyzed on FlowJo software, Ver. 9.5.2 (TreeStar).

3.6. Cytokine Release and Cytotoxicity Assays

To measure cytokine production $6 \times 10^4$ 1928z-T-iPSC-T cells were seeded on irradiated CD19$^-$ or 3T3-CD19 cells in a 3:1 ratio (E/T ratio) per well of a 96-well plate in T-cell medium with IL-7 (10 ng/ml) and IL-15 (10 ng/ml). Culture supernatants were collected after 24 h and the concentration of type I and/or type II cytokines was quantified with a Luminex assay kit (Invitrogen) according to manufacturer instructions. Cytotoxic potential of 1928z-Ti-T cells was evaluated in standard $^{51}$Cr release assays. Target cells were labeled with $^{51}$Cr and co-cultured with 1928z-T-iPSC-T cells at decreasing effector/target (E/T) ratios. After 4 h of culture, supernatant was removed and radioactivity released from chromium was measured. Specific lysis was determined by subtracting background radioactivity of target cells not cultured with T cells and dividing by the radioactivity measured from target cells completely lysed by treatment with 0.2% Triton X-100. The murine lymphoma cell line EL4, engineered to express ovalbumin (EL4-OVA) or human CD19 (EL4-CD19), was used as target (41).

3.7 Microarray Procedure and Gene Expression Analysis

Whole PBLs were isolated from two healthy donors by Ficoll density centrifugation after informed consent was obtained. The following subpopulations: CD3$^+$CD4$^+$, CD3$^+$CD8$^+$, CD3$^+$CD56$^+$, CD3$^+$CD56$^+$ (NK) and CD3$^+$TCR$\gamma\delta^+$ ($\gamma\delta$ T cells) were purified (98%) from PBL by cell sorting.

Total mRNA was extracted from 1928z-T-iPSC-T cells at days 30-35 of differentiation and from the sorted PBL subpopulations using TRIzol™ Reagent (Invitrogen Life Technologies, Paisley, UK). Microarray analyses were performed at the MSKCC Genomics Core facility using 75 ng of total RNA as the starting material, amplified and labeled following the standard Affymetrix protocol (Affymetrix, Santa Clara, Calif., USA). The labeled complementary RNA was then fragmented and hybridized to Affymetrix GeneChip arrays HG-U133 plus 2.0.

For the gene expression analysis the raw data (Affymetrix CEL files) produced using HG U133-Plus 2.0 platform were used. For comparison purposes, additional raw data files obtained on the same platform were downloaded from the NCBI repository GEO database: five samples of normal naive B cells (GSE12195), five samples of $\alpha\beta$ $CD4^+$ cells (GSE15659), one sample of resting $\alpha\beta$ $CD8^+$ cells (GSE8059), one sample of resting NK cells (GSE8059), 12 samples of $TCRV\gamma9\gamma\delta$ T cells (GSE27291), before activation and after activation with BrHPP/IL-2 (bromohydrin pyrophosphate and IL-2) for 6 h or 7 d. Robust Multi-array Average (RMA) procedure was applied to all CEL files and comparisons of different samples were performed upon z-scores normalization. Gene-centric expression values were obtained using a CDF file based on remapping of probes to the human genome. Gene expression levels were compared both between single samples and by grouping samples of the same type in an unbiased way. Similarity between samples was evaluated by Pearson's correlation coefficient computed between a selected list of probes: 1,163 probes were selected based on their variability across samples (s.d.>0.75) and consistency among 1928z-T-iPSC-T cells (s.d.<1). Correlations between groups were computed after averaging probe expression levels of single samples of the same type. Using the computed set of correlations, hierarchical clustering of the single samples was performed. The clustering was performed using the R package hclust with the default settings (Euclidean distance). Second, a comparison between the analyzed samples on a selected panel of genes was performed.

3.8 Quantitative Real-Time PCR

Total mRNA was extracted using TRIzol™ Reagent (Invitrogen Life Technologies, Paisley, UK). Reverse transcription was done using the Superscript III First-Strand Synthesis supermix for qRT-PCR (Invitrogen). Quantitative-PCR for specific genes were done using the respective probe-based TaqMan Gene Expression assays (Applied Biosystems). Reactions were carried out in duplicate in an ABI PRISM 7500 Sequence Detection System (Applied Biosystems). Expression was calculated by relative quantification using the DDCt method with GAPDH as endogenous control.

3.9 Isolation and Retroviral Transduction of $\gamma\delta$ and $\alpha\beta$-T Cells PBL were isolated from the same donor as the T-iPSC. TCR$\gamma\delta$ T cells were isolated with magnetic cell sorting (negative selection) using the $TCR\gamma\delta^+$ T-cell Isolation Kit (Miltenyi Biotec) according the manufacturer's instructions. Next, TCR$\gamma\delta$ T cells were stimulated with 5 mM zoledronic acid (Zometa, Novartis) and 1,000 IU/ml IL-2 for 48 h. The TCR$\alpha\beta$ fraction of PBLs (obtained as the positive fraction after negative selection of TCR$\gamma\delta$ T cells) was activated with PHA 2 mg/ml for 48 h. Synthesis of the 1928z-CAR-encoding 1928z-IRES-LNGFR vector has been described (41). Retroviral producers were prepared from plasmid-transfected H29 cell supernatants as previously described (41). Activated $\gamma\delta$ and $\alpha\beta$ T cells were transduced with retroviral supernatants on two consecutive days by spin-infection in retronectin (Takara)-coated oncoretroviral vector-bound plates. Cells were fed every 3 d with T-cell medium supplemented with 1,000 IU/ml or 20 IU/ml of IL-2 for $\gamma\delta$ and $\alpha\beta$ T cells, respectively.

3.10 In Vivo Tumor Model 6- to 12-week-old male NOD-SCID $IL2R\gamma c^{null}$ mice, obtained from the MSKCC Mouse Genetics Core facility, were inoculated i.p. with $10^5$ Raji human CD19+ Burkitt lymphoma cells expressing a green fluorescent protein-firefly luciferase fusion protein (GFP/Luc) as previously described (9, 40). Four days later $4\times10^5$ expanded (1-week stimulation on irradiated 3T3-CD19) 1928z-T-iPSC-T cells or CAR-transduced syngeneic $\alpha\beta$ or $\gamma\delta$ T cells were injected i.p. along with IL-2 (50,000 U/mouse) and IL-15 (0.25 mg/mouse). Only mice that had equal tumor burden ($2\times10^6\pm0.5\times10^6$ photons/sec) before T-cell injection were used. Mice with lesser or greater tumor burden were excluded from the study. Tumor-bearing mice retained in the study were randomized to the different treatment groups (at least four mice per group). No blinding method was used. T-cell dose was based on the percentage of $CAR^+$ cells as measured by pre-injection flow cytometric analysis. IL-2 administration was continued daily and IL-15 every 2 d for 2 weeks. Tumor burden was monitored twice per week by in vivo bioluminescence imaging (IVIS 100 Imaging System). Living Image software Version 4.3.1 was used to acquire and quantify the bioluminescence imaging data sets. All animal experiments were conducted in accordance with protocols approved by MSKCC Institutional Animal Care and Use Committee (IACUC) and following National Institutes of Health guidelines for animal welfare.

3.11 Statistical Methods

No pre-specified effect size was used to determine sample sizes. The use of statistical tests was chosen according to the nature of the data. The Wilcoxon rank-sum test (Mann-Whitney U test) was used to compare the tumor burden across multiple groups. This test was chosen because of its robustness to the underlying distribution of the observations. Comparison of survival curves was done using the log-rank test. Partial likelihood ratio test from a Cox regression model was also used to compare the survival between 1928z-T-iPSCT and no treatment groups after ensuring that the data were consistent with the proportional hazards assumption (P=0.15 using the weighted-residuals test) (42). As it was unable to fit a Cox model for the remaining treatment groups due to the paucity of events, the reported P-values are those provided by the log-rank test. Statistical significance was defined as P<0.05. Statistical analyses were done on Prism software (GraphPad) (tumor burden comparison and log-rank) or R (microarray analysis and Cox proportional hazards regression).

Figure 1B:
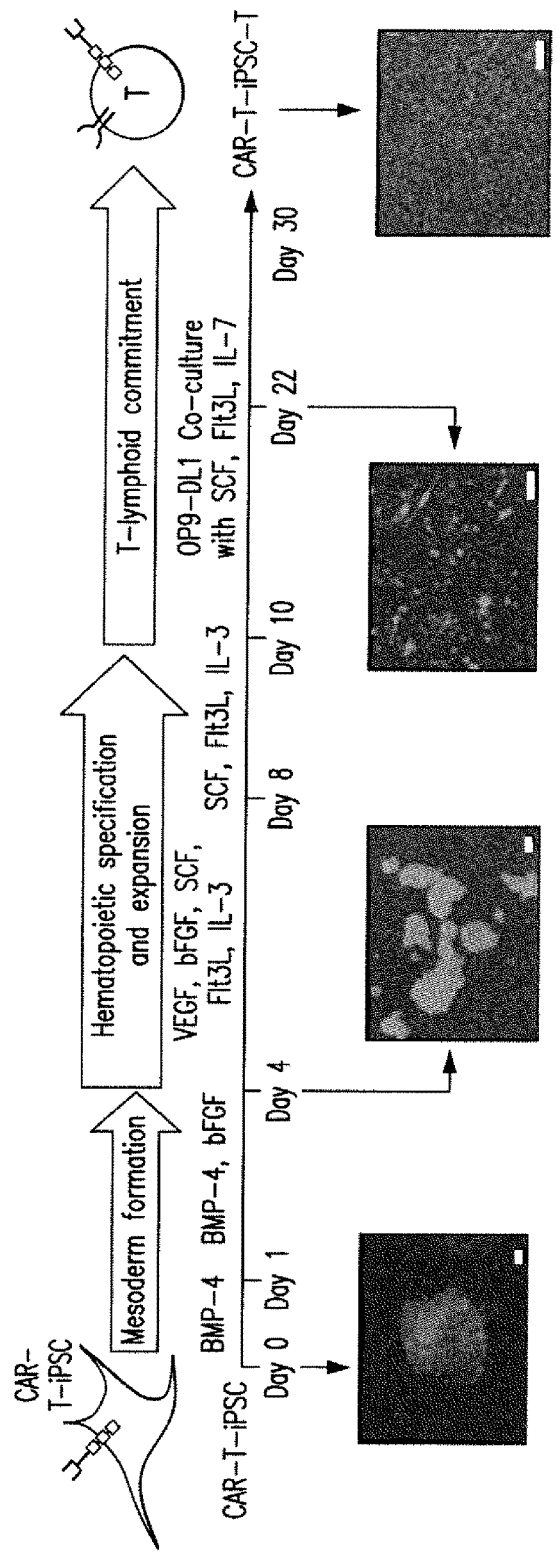
Figure 5A:
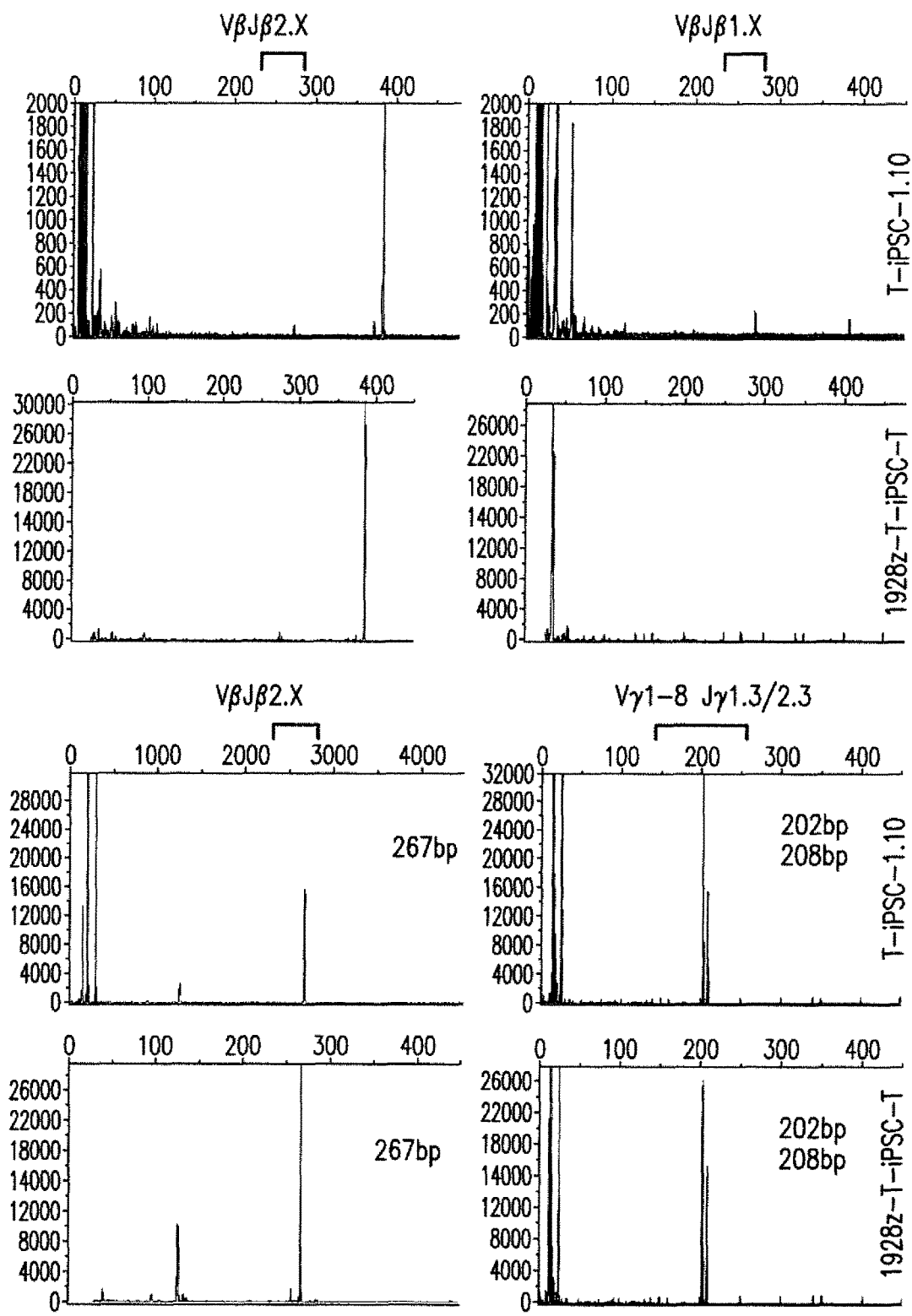
FIGS. 5A and 5B show T cell receptor (TCR) β and γ chain rearrangements. (A) TCRβ and TCRγ rearrangement analysis of the parental line T-iPSC-1.10 and 1928z-T-iPSC-T lymphocytes using multiplexed PCR primers targeted to conserved regions within the V-J region of the TCR β and γ loci and PCR fragment analysis. (B) TCRβ rearrangement analysis of lines T-iPSC-1.3 and T-iPSC-1.4. X-axis: fragment size (bp), Y-axis: fluorescence intensity (RFU). Red brackets depict the valid PCR fragment size range on the electropherogram.
Figure 5B:
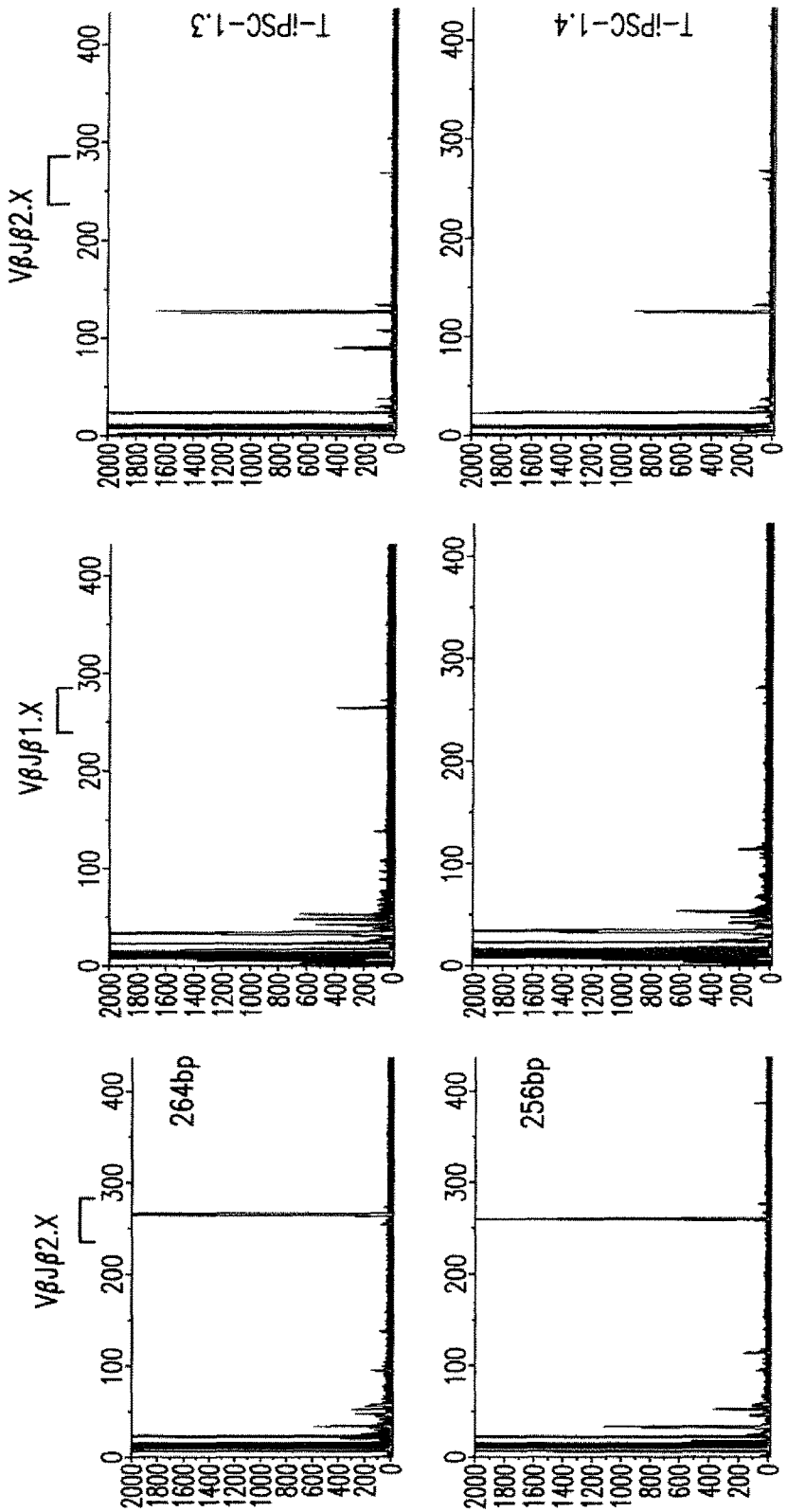
Figure 6B:
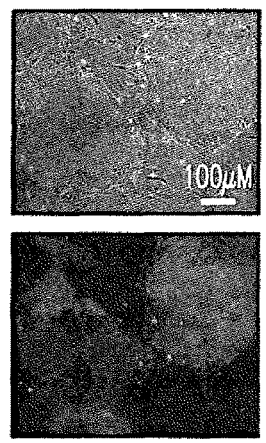
Figure 6C:
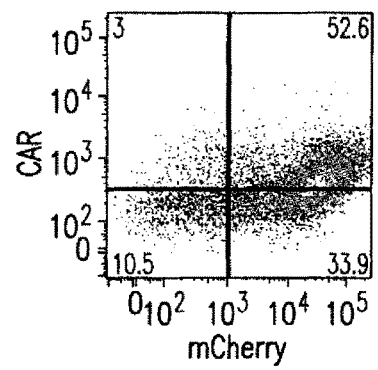

4. Results iPSC clones (T-iPSCs) was generated by transducing peripheral blood T lymphocytes (PBL) from a healthy volunteer with two retroviral vectors each encoding two of the reprogramming factors KLF4, SOX2, OCT-4 and C-MYC (FIG. 4A) (7). Multiple randomly selected T-iPSC clones were analyzed, and their pluripotency (FIGS. 4B to 4G) and T-cell origin (FIGS. 5A and 5B) were confirmed. Clone T-iPSC-1.10 was stably transduced with a bicistronic lentiviral vector encoding 19-28z (1928z-T-iPSC), a second-generation CAR specific for CD19, and the fluorescent marker mCherry (FIGS. 6A to 6C) (14). To direct the differentiation of 1928z-T-iPSC to the T-lymphoid lineage, a serum- and feeder-free in vitro differentiation protocol for the generation of hematopoietic precursors through embryoid body formation was first optimized (FIG. 1B).

Figure 1C:
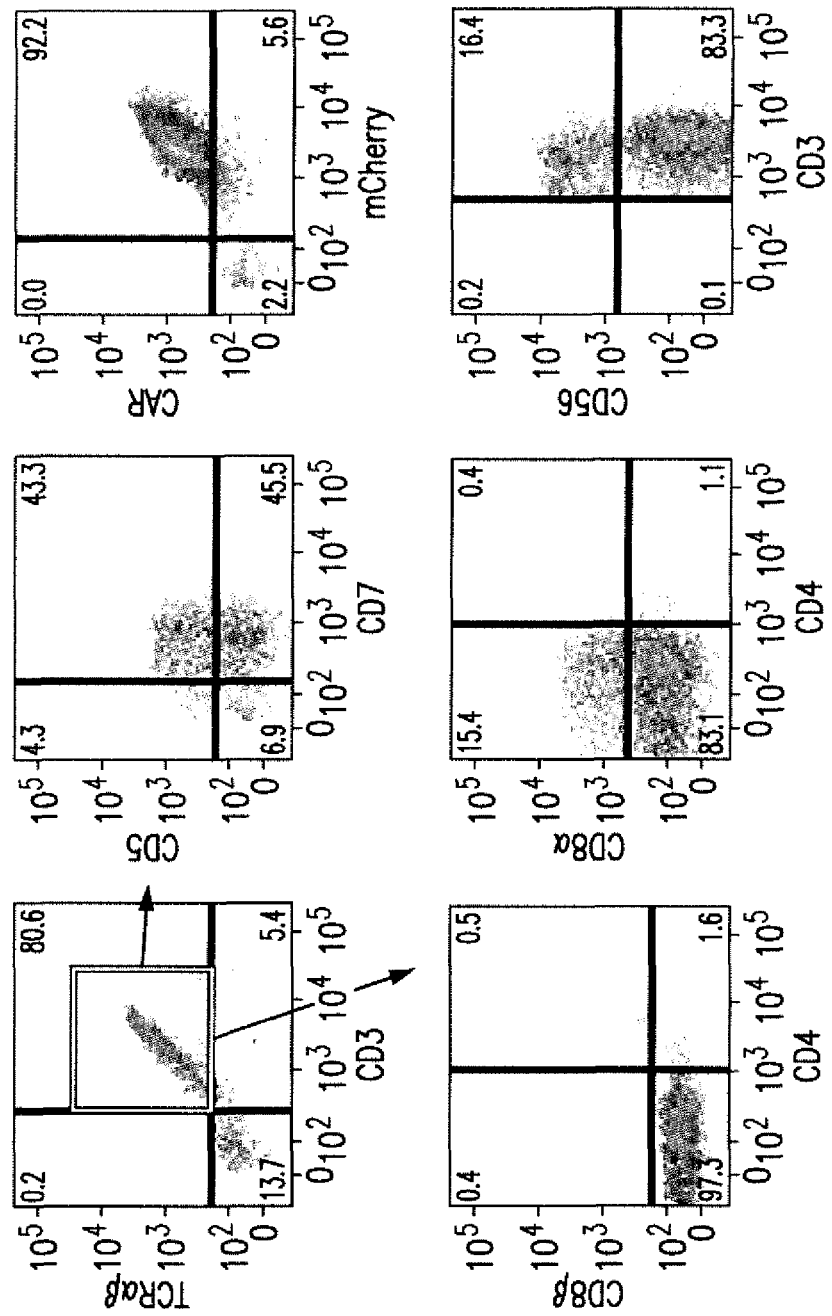
Figure 8B:
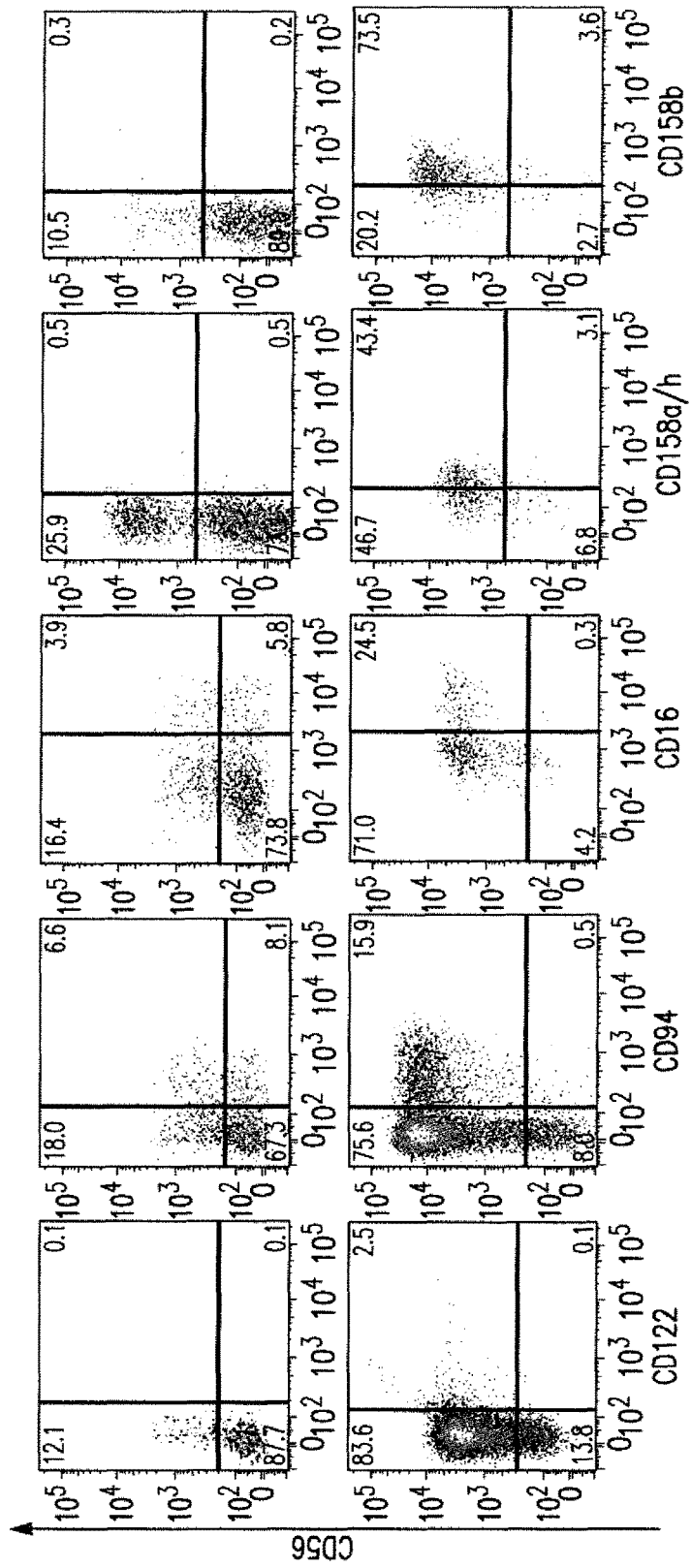

Similar to previous reports (3, 4, 15), it was found that CD34+ cells from day 10 embryoid bodies expressed the highest levels of key transcription factors for lymphoid differentiation (FIG. 7A), specifically showing increased expression of Notch 1 and CD127 (IL7Rα) in the CD34$^+$CD43$^-$ subset compared to CD34$^-$CD43$^-$ cells (FIG. 7B). Day 10 embryoid bodies were dissociated and the hematopoietic precursors were transferred onto Delta-like 1-expressing OP9(OP9-DL1) feeder cells to induce T-lymphoid differentiation in an established co-culture system in the presence of the cytokines stem cell factor (SCF), Flt3L and interleukin (IL)-7 (FIG. 1B). mCherry expression was ascertained throughout the differentiation process and no substantial silencing of mCherry expression was detected (FIG. 1B). As early as day 25 of differentiation, CD7$^+$CD3$^+$TCRαβ+ cells were detected (Table 2). As shown in Table 2, the expression of each surface marker on cells gated as indicated was measured by flow cytometry at day 25 and 30 of differentiation and 7 days after expansion on 3T3-CD19 cells (expanded). These cells harbored the same TCR β and γ chain rearrangements as the parental T-iPSC-1.10 line (FIG. 5C). By day 30, CD3+TCRαβ$^+$ cells typically accounted for ~80% of the cultures (FIG. 1c and Supplementary Table 1), and all of them expressed the CD19-specific CAR on their surface; day 30 cells are referred to hereafter as 1928z-T-iPSC-T cells (FIG. 1C). A substantial fraction expressed CD8α (10.4±3.5%) and CD56 (20.7±9.5%), whereas very few cells expressed low amounts of CD4 and almost no cells expressed detectable CD8β (FIG. 1C and Table 2). Further surface phenotyping showed most cells to be CD5$^{low}$ and negative for CD122 and TCRγδ (FIG. 1C, FIGS. 8A and 8B and Table 2).

TABLE 2

Summary of Flow Cytometric Data Analysis

| Surface marker | | day 25 | | day 30 | | expanded | |
|---|---|---|---|---|---|---|---|
| | CD7+ | 53 ± 16.7 | 6 | 64.2 ± 10.5 | 5 | na | na |
| CD7+ | CD5 | 32.6 ± 12.9 | 3 | 39.6 ± 8.7 | 3 | na | na |
| | CD56 | 8 ± 2.8 | 2 | na | na | na | na |
| | CD3 + TCR+ | 54.4 ± 16.4 | 6 | 78 ± 1.7 | 4 | 88.4 ± 6.1 | 3 |
| CD3+ | CD56 | 16.7 ± 6.3 | 6 | 20.7 ± 9.5 | 3 | 89.6 ± 7.5 | 2 |
| | CD8α | 14.3 ± 3.6 | 5 | 10.4 ± 3.5 | 2 | 48.7 ± 11.5 | 3 |
| | CD4 | 3.5 ± 0.7 | 3 | 2.6 ± 0.5 | 3 | 11.1 ± 1.9 | 3 |
| | CD5 | 33.7 ± 3.1 | 2 | 41.5 ± 10.3 | 4 | na | na |
| | CD161 | 39.6 ± 12.3 | 3 | na | na | 15.7 ± 6.08 | 2 |
| | CD122 | 0 | 2 | na | na | 2.5 | 1 |
| | CD16 | 23.3 ± 6.8 | 2 | na | na | 24.5 | 1 |
| | CD94 | 13.2 ± 2.1 | 2 | na | na | 14.3 | 1 | na: not available

Figure 1D:
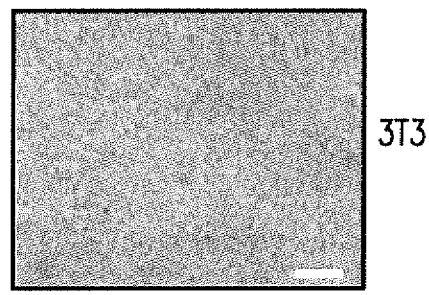
Figure 1D:
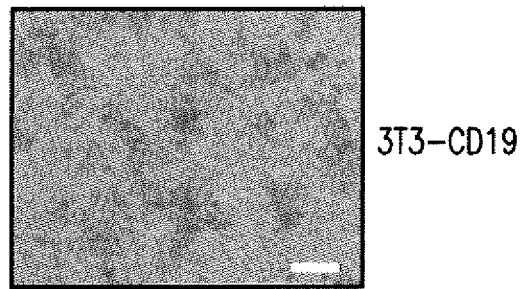
Figure 1E:
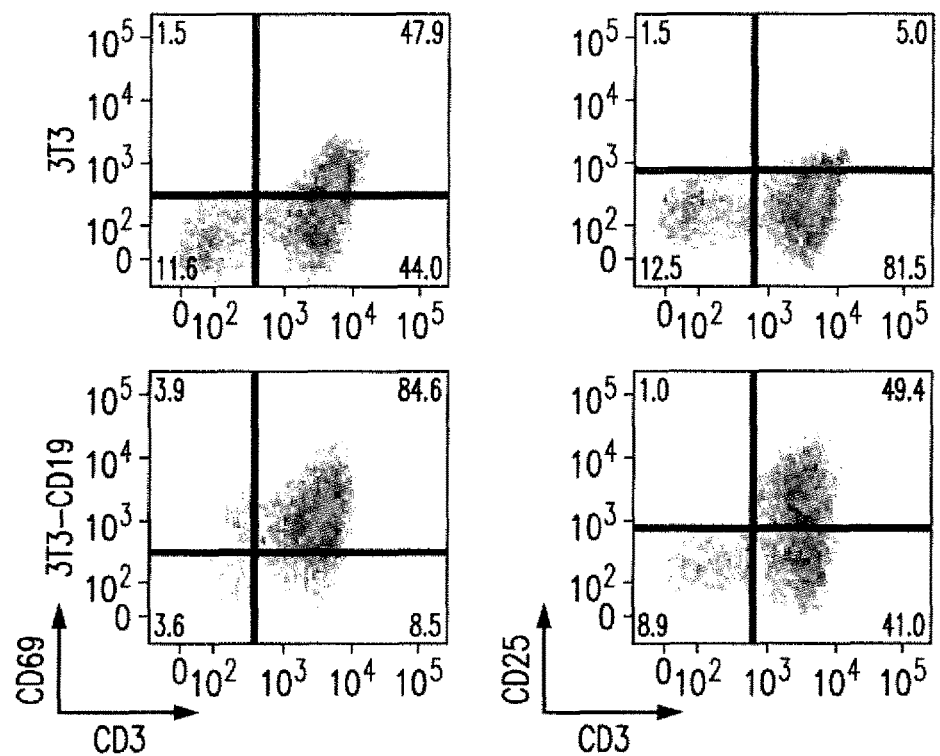
Figure 1F:
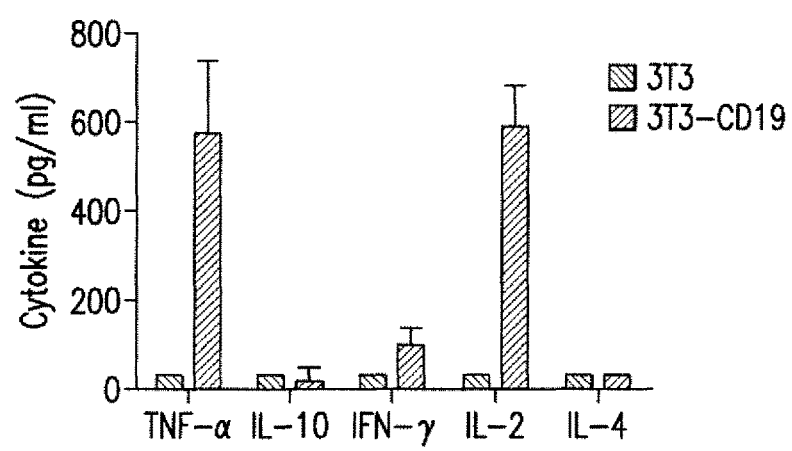

Taking advantage of the CD19-specific CAR, the functional response of 1928z-T-iPSC-T cells to cell-bound CD19 was evaluated. 1928z-T-iPSC-T cells harvested on days 30-35 of differentiation were cultured on NIH-3T3-based artificial antigen-presenting cells (AAPCs) expressing the CD19 antigen (3T3-CD19) where indicated (9). The 1928z-T-iPSC-T cells rapidly bound to 3T3-CD19 cells, forming clusters and eliminating the 3T3-CD19 monolayer (FIG. 1D). No such adhesion was observed when 1928z-T-iPSC-T cells were placed on CD19-negative 3T3 cells (FIG. 1D). Exposure to 3T3-CD19 cells also prompted 1928z-T-iPSC-T-cell surface expression of T-cell activation markers CD25 and CD69 (FIG. 1E) and secretion of type 1 cytokines such as IL-2, tumor-necrosis factor (TNF)-α and interferon (IFN)-γ (FIG. 1F). These results show that 1928z-T-iPSC-T cells displayed canonical features of T-lymphocyte function and specificity for the CD19 antigen.

Figure 2A:
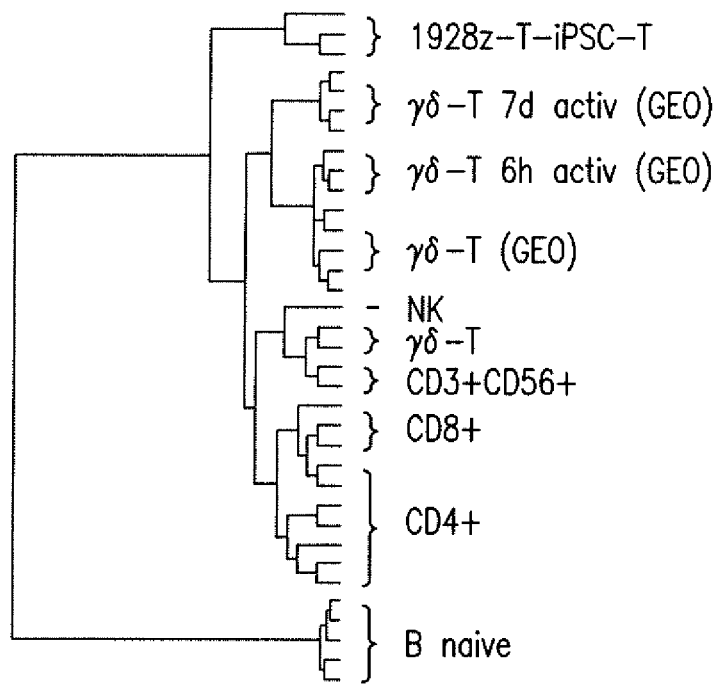
FIGS. 2A-2G show phenotypic profiling of 1928z-T-iPSC-T cells before and after CD19-induced expansion. (A) Unsupervised hierarchical clustering of 35 total transcriptomes, generated by an mRNA gene expression microarray, from 1928z-TiPCS-T cells at days 30-35 of differentiation (1928z-T-iPSC-T) and other human lymphoid cell subsets isolated for this study [CD3$^+$TCRγδ$^+$ cells (γδ-T), CD3$^+$CD56$^+$ cells, CD8$^+$ cells and CD4$^+$ cells] or downloaded from the NCBI repository GEO database (naive B cells, TCRVγ9γδ T-cells before activation (γδ-T GEO) and after activation with BrHPP/IL-2 (bromohydrin pyrophosphate/interleukin-2) for 6 h (γδ-T 6 h activ) or 7 days (γδ-T 7d activ) and resting NK cells). (B) Heatmap comparing the expression of indicated mRNA transcripts expressed in lymphoid and/or NK cells. Transcripts are classified according to known function and expression patterns. (C) Intracellular expression of the transcription factor PLZF (red histogram), compared to isotype control (black histogram), and surface expression of CD161 and CD3 in 1928z-T-iPSC-T cells, as assessed by flow cytometry. (D) Expansion of 1928z-T-iPSC-T cells after weekly stimulations with 3T3-CD19 cells in the presence of IL-7 (10 ng/ml) and IL-15 (10 ng/ml) for 4 weeks. Absolute cell numbers are shown. Arrows indicate restimulations with freshly irradiated 3T3-CD19 AAPCs. (E) Flow cytometric analysis of cell surface molecules and cytotoxic receptors in gated CD3+ 1928z-T-iPSC-T cells before and 7 d after expansion on 3T3-CD19 AAPCs. (F and G) qRT-PCR analysis of the expression of the indicated mRNA transcripts in 1928z-T-iPSC-T cells before and 7 d after expansion on 3T3-CD19 AAPCs. Data were normalized to the values of endogenous GAPDH and pre-expansion expression levels were used as reference. Graphs represent average of intra-assay technical triplicates. Error bars, mean±s.d.
Figure 2B:
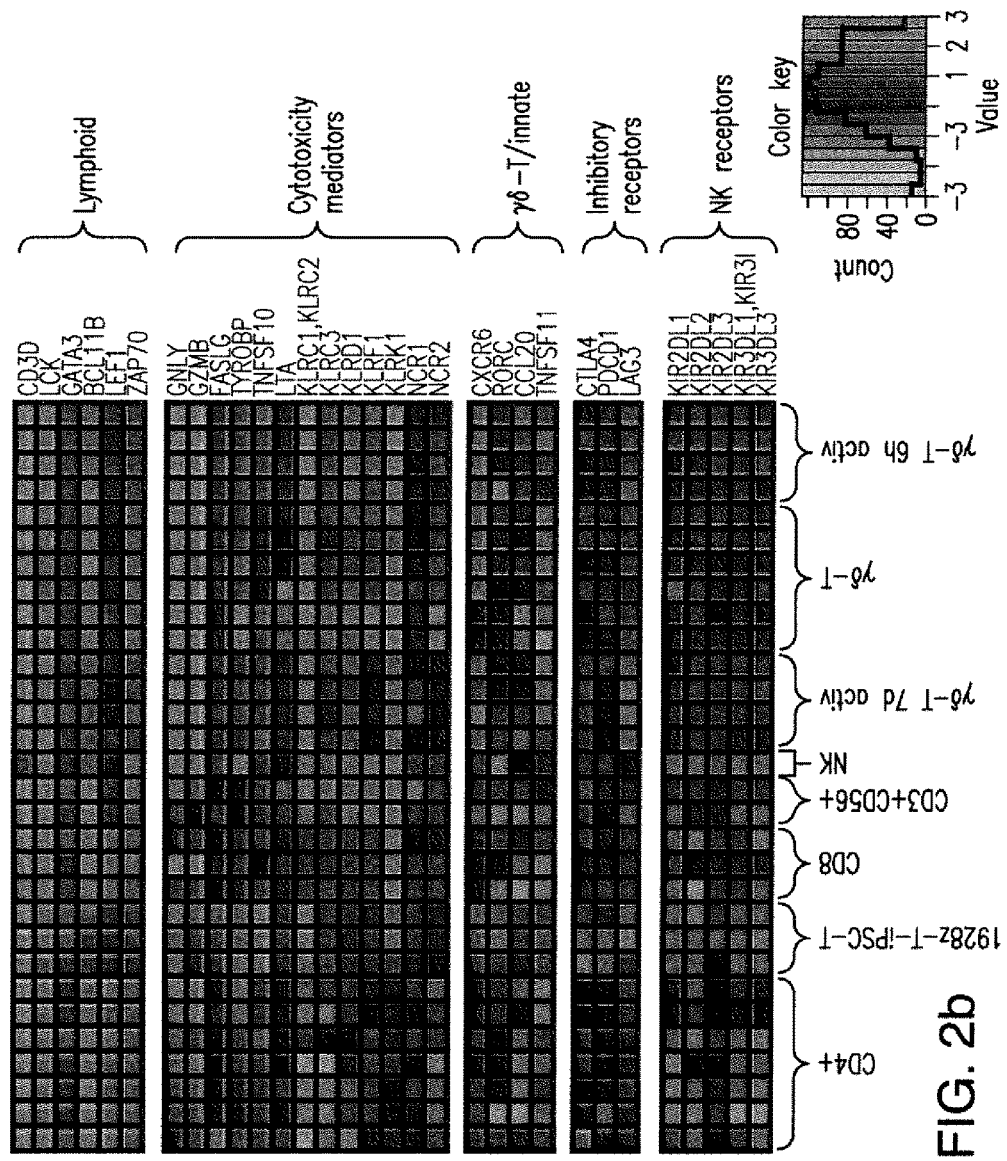
Figure 2C:
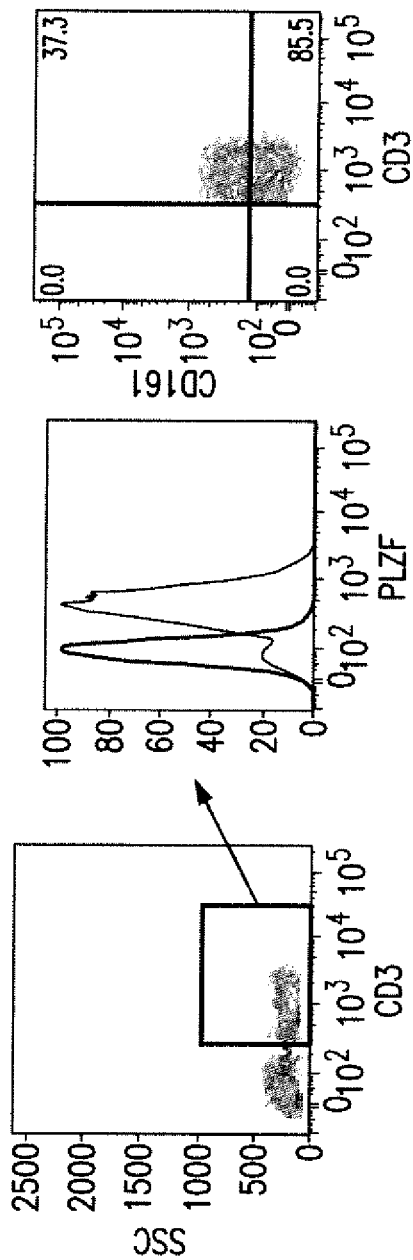
Figures 1, 2D:
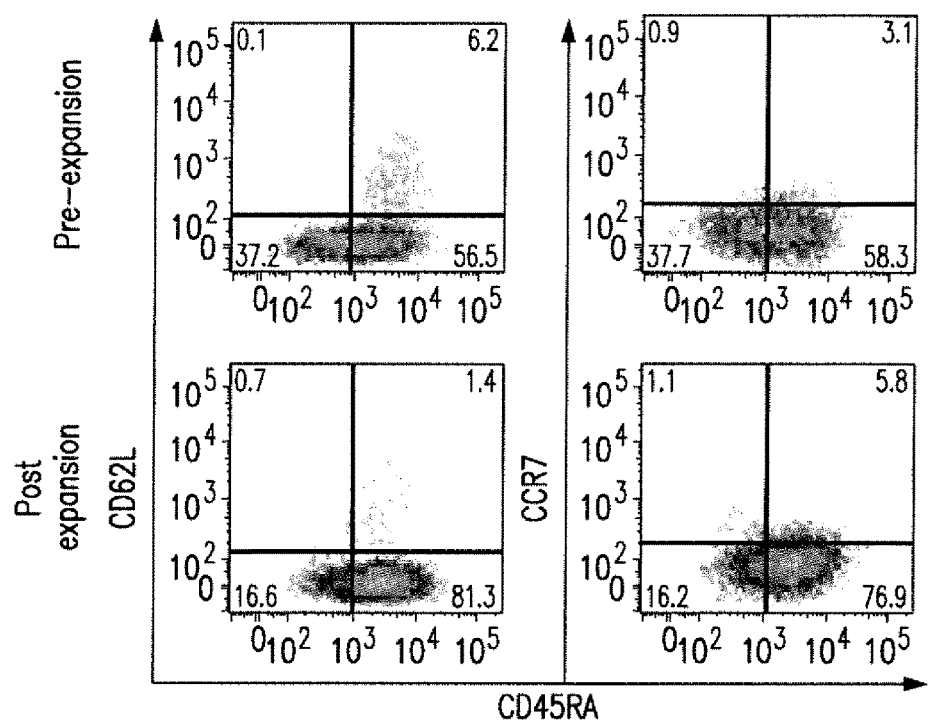
Figures 2, 2D:
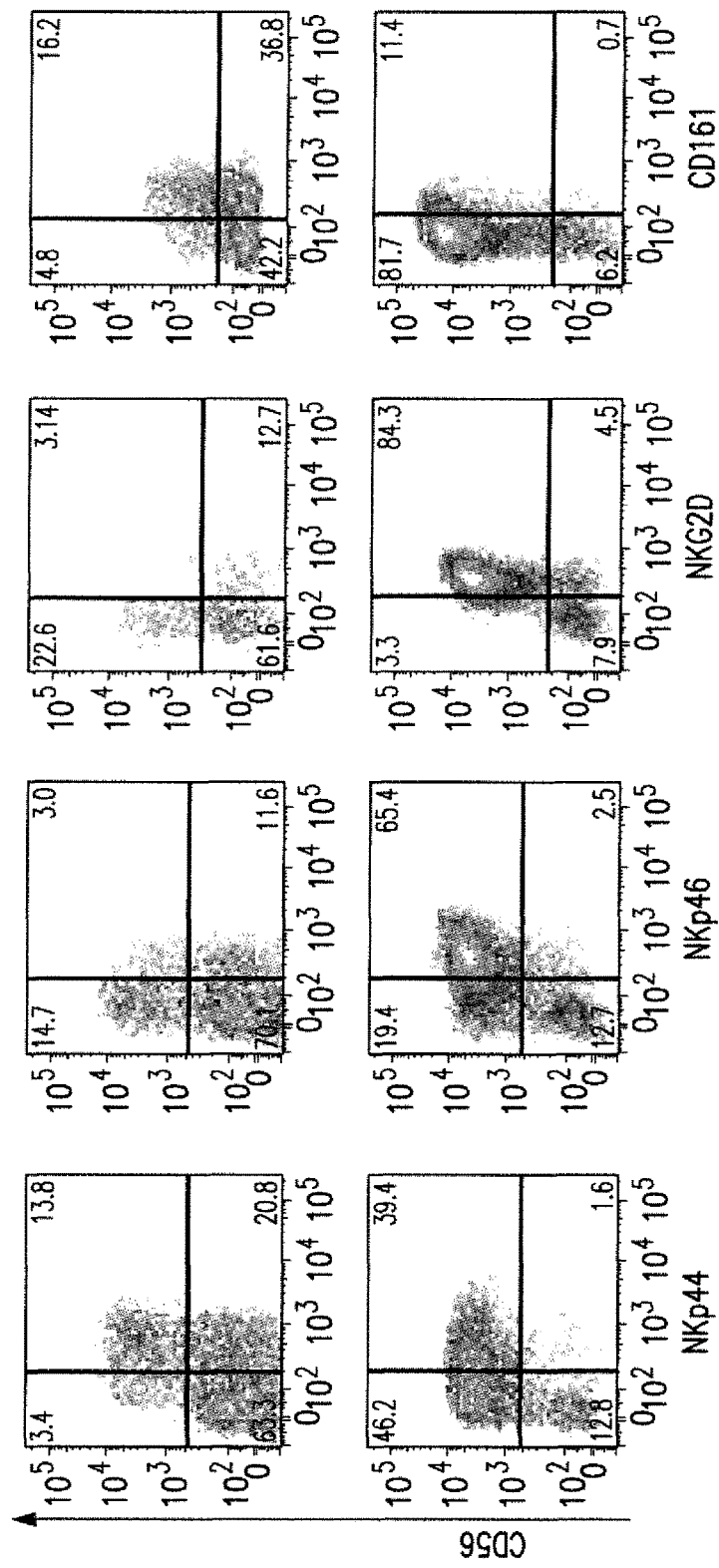
Figure 2E:
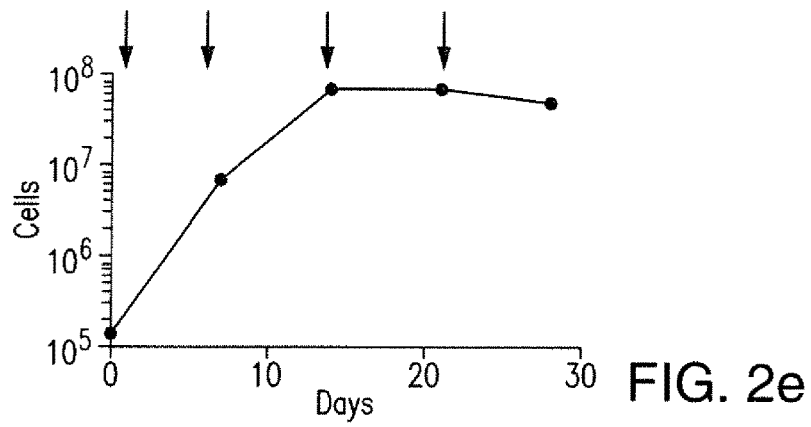
Figure 2F:
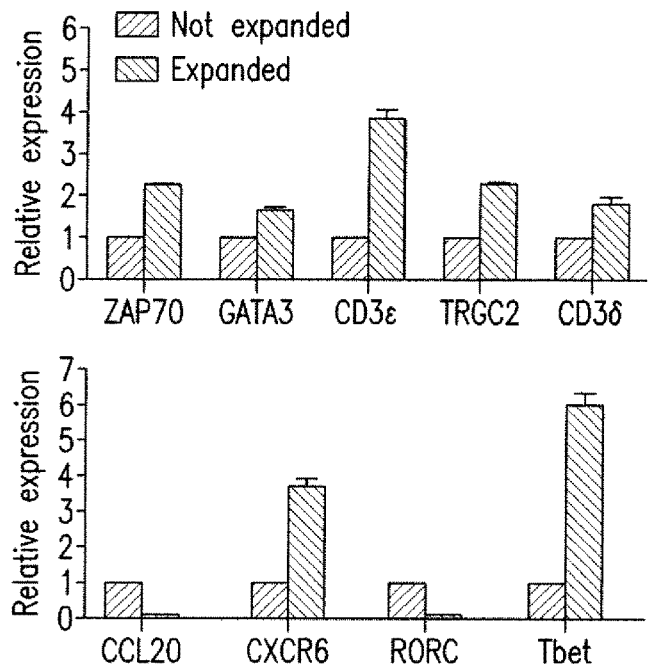
Figure 2G:
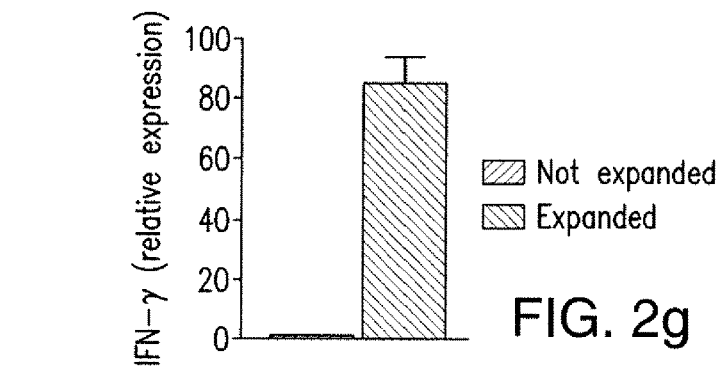
Figure 8C:
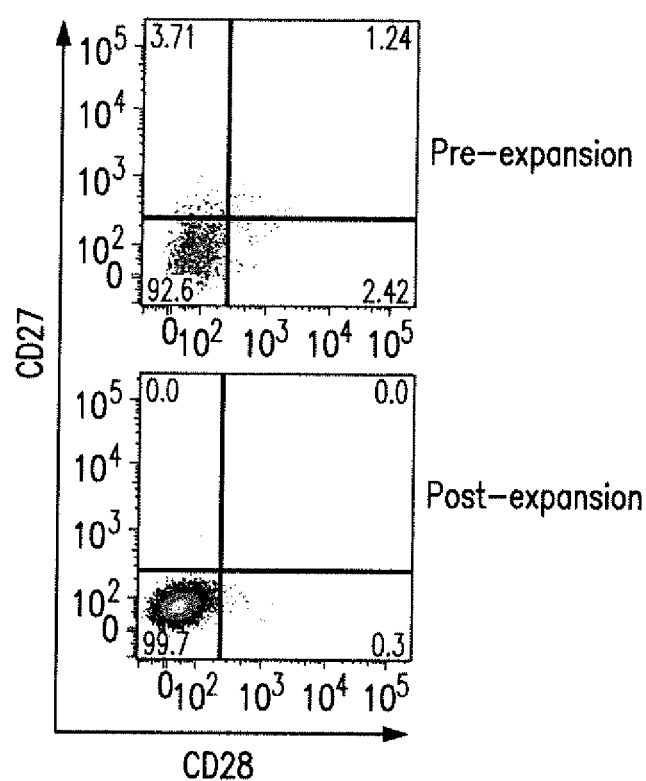
Figure 9A:
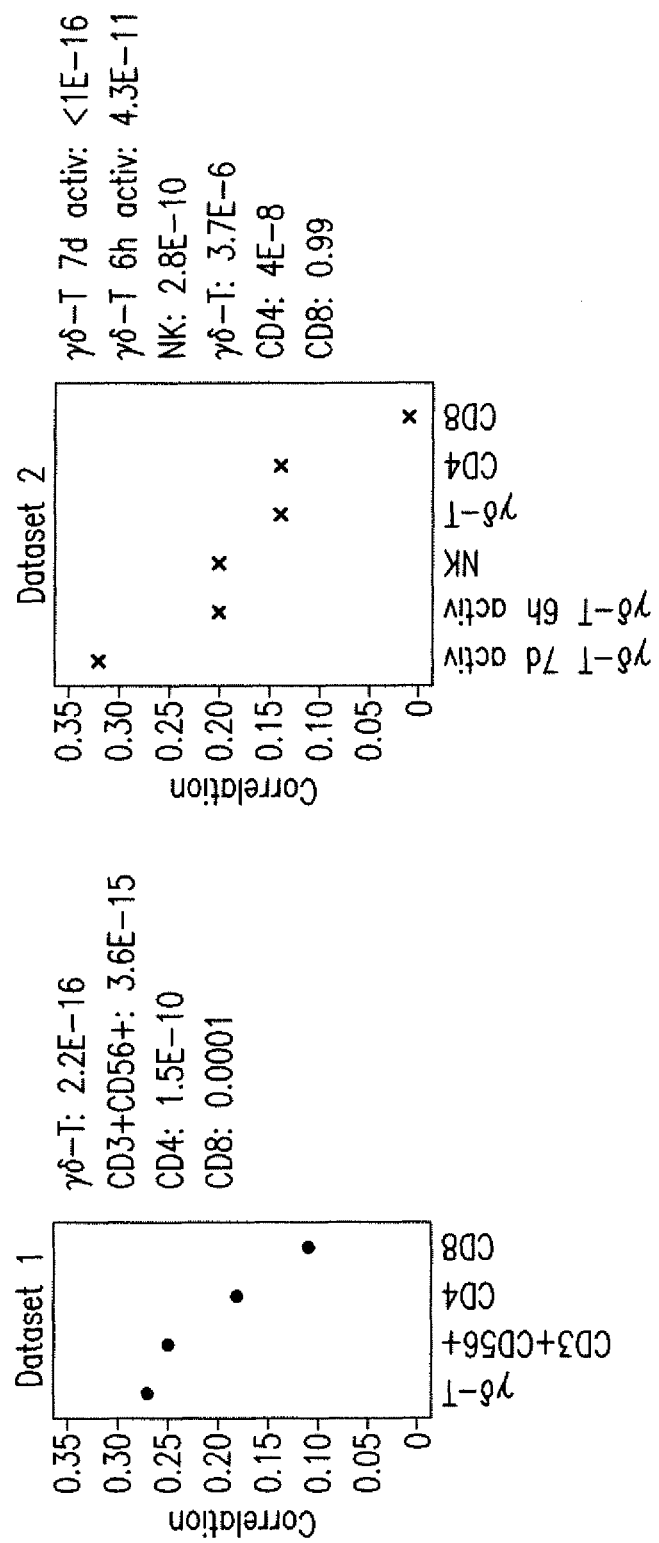
FIGS. 9A and 9B show comparison of mRNA gene expression between 1928z-T-CC-T cells and control peripheral blood lymphoid subsets. (A) Plots demonstrating the gene expression similarity, computed as Pearson's correlation coefficients, between 1928z-T-iPSCT cells and other lymphoid subsets as depicted. Dataset 1: samples collected for this study, Dataset 2: samples downloaded from the NCBI repository GEO (Gene Expression Omnibus) database. (B) Expression of major transcription factors, cytolytic molecules and surface molecules, that are characteristic of the T, NK and γδ-T lineages in NK cells, CD4, CD8 and γδ T cells and 1928z-T-iPSC-T cells before and after 1 week of expansion on 3T3-CD19, as assessed by qRT-PCR. Data were normalized to the values of endogenous GAPDH and are shown as relative expression compared to the expression in γδ T cells. Graphs represent average of intra-assay technical triplicates (error bars=SD).
Figure 9B:
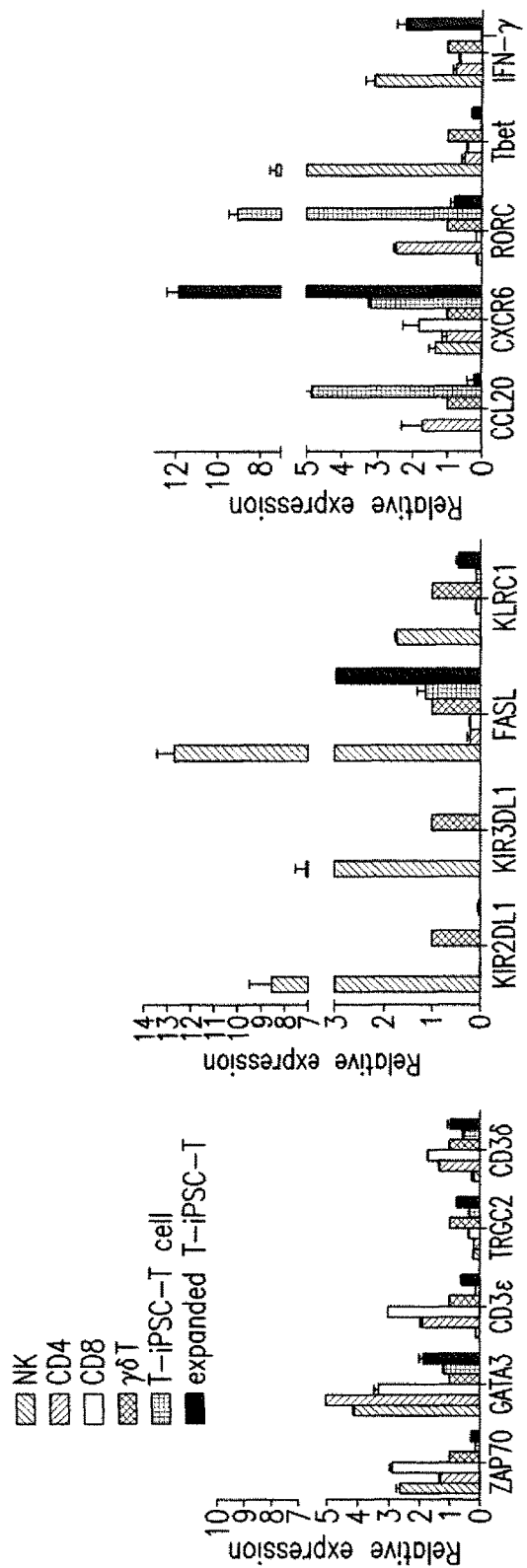

To better elucidate the phenotype of 1928z-T-iPSC-T cells, a gene expression microarray was carried out, and the mRNA expression profile of days 30-35 1928z-T-iPSC-T cells was compared to that of naive B cells, CD4 T cells, CD8 T cells, CD3$^+$CD56$^+$ T cells and natural killer (NK) cells isolated from peripheral blood. The profile was also compared to freshly isolated or in vitro-activated peripheral blood γδ T cells. Hierarchical clustering using the set of genes with most variable mRNA expression (s.d.>0.75) showed that 1928z-T-iPSC-T cells were distinct from B cells and more closely related to the other T-lymphoid subsets and NK cells (FIG. 2A). Next, 1928z-T-iPSC-T cells were compared to particular lymphoid cell subsets by correlating mRNA expression levels of the most variable genes in the data set. This pairwise correlation analysis indicated that 1928z-T-iPSC-T cells were more similar to fresh or activated (for 7 d) γδ T cells (FIG. 9A). This correlation was further confirmed upon examining expression of key lymphoid differentiation genes. The 1928z-T-iPSC-T cells expressed genes characteristic of the T-lymphoid lineage (e.g., GATA3, CD3δ, CD3ε, LEF1, LCK and BCL11B) at levels comparable to those of peripheral blood γδ T cells; however, the 1928z-T-iPSC-T cells did not express many genes characteristic of the NK cell lineage (e.g., CD94, CD16 and killer-cell immunoglobulin-like receptors) (FIGS. 2B, 8 and 9B). Moreover, pronounced expression of FASLG, TYROBP, CCL20, TNFSF11 (RANKL), CXCR6 and RORC, genes that are highly expressed in γδ T cells versus αβ T cells and/or NK cells, was detected in 1928z-T-iPSC-T cells (FIGS. 2B and 9B) (16). The innate immune cell property of 1928z-T-iPSC-T cells was further supported by their expression of the transcription factor PLZF and the surface marker CD161 (FIG. 2C). Interestingly, 1928z-T-iPSC-T cells also showed high cytotoxic potential as indicated by high expression of TNFSF10 (TRAIL), GNLY, GZMB, FASL, LTA and low expression of co-inhibitory or exhaustion markers PD1, CTLA-4 and LAG3 (FIG. 2B). The majority of the CD3$^+$ cells had a CD45RA$^+$CD62L$^-$CCR7$^-$ effector memory phenotype (TEMRA), although a small percentage (~6%) had a more naive CD45RA$^+$CD62L$^+$ phenotype (FIG. 2D). No expression of CD27 or CD28 receptors was detected on the surface of 1928z-T-iPSC-T cells (FIG. 8C).

iPSC-derived T cells will be therapeutically relevant only if they can be expanded while retaining functional properties. Therefore, 1928z-T-iPSC-T cells were expanded using 3T3-CD19 cells and the expanded T cells were characterized. Starting from 3×10$^6$ 1928z-T-iPSC, ~1-2×10$^5$ 1928z-T-iPSC-T cells were obtained by day 30 of differentiation. Those 1928z-T-iPSC-T cells were expanded 10- to 50-fold (mean=20, s.d.=15, n=6) after one stimulation and up to ~1,000-fold after three weekly stimulations (FIG. 2E). Therefore, although the differentiation efficiency at day 30 is around 0.05, it was increased to 0.5-1.0 by 1 week and up to 50.0 after 3 weeks of expansion. The expanded cells maintained their effector memory phenotype and upregulated the expression of natural cytotoxicity receptors such as NKp44, NKp46 and NKG2D (FIG. 2E). Interestingly, the expanded cells upregulated expression of T-lymphoid lineage-specific genes (ZAP70, GATA3, CD3δ, CD3ε, TRGC2) and down-regulated expression of RORC, indicative of a switch toward a type 1 (Tbet/IFN-γ expressing) phenotype (FIGS. 2F and 2G). CD161 surface expression was also reduced after expansion (FIGS. 2D and 2E). In aggregate these findings suggest that CAR-mediated proliferation polarized the 1928z-T-iPSC-T cells toward a type 1 response. A similar phenotype switch has been shown for RORC-expressing T17 γδ T cells, IL-17-producing fetal innate lymphoid cells and murine TCR-transgenic Th17 cells, which polarize to type 1 cells after antigen or cytokine stimulation (17-19).

Figure 3A:
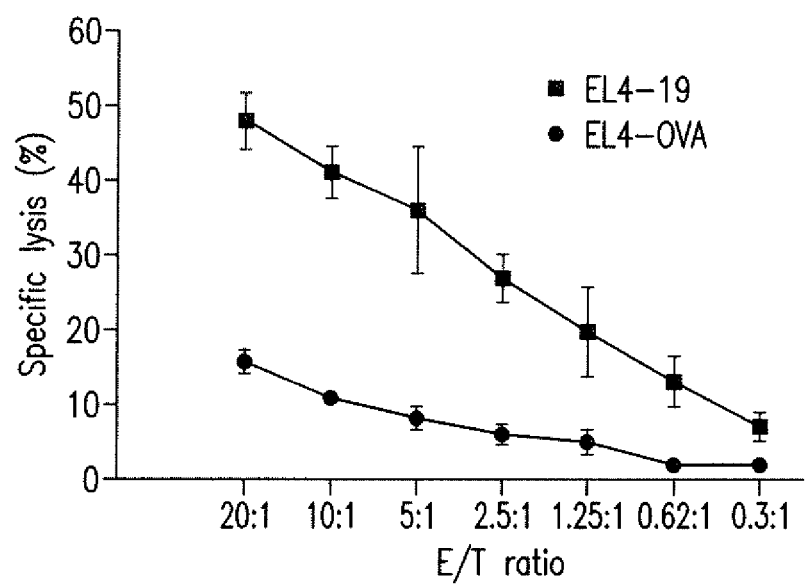
FIGS. 3A-3E show 1928z-T-iPSC-T cells lyse CD19-positive tumor cells in vitro and in vivo. (A) In vitro 51Cr release assay of 7 d-expanded 1928z-T-iPSC-T cells (effectors) and the murine lymphoma cell line EL-4 expressing ovalbumin (EL4-OVA) or human CD19 (EL4-CD19) (targets). E/T, effector/target ratio. Representative of two independent experiments. (B) Flow cytometric analysis of 1928z-T-iPSC-T cells and syngeneic 1928z-transduced γδ (1928z-γδ) and αβ (1928z-αβ) T cells before their injection into tumor-bearing mice. Bottom: black histogram, untransduced cells; red histogram, transduced cells. Representative plots of two independent experiments. (C) NOD-SCID IL2Rγc$^{null}$ mice were inoculated intraperitoneally with CD19+ Raji human Burkitt lymphoma cell line expressing a green fluorescent protein-firefly luciferase fusion protein (GFP/Luc). Four days later, T cells ($4 \times 10^5$) described in B were injected intraperitoneally. No treatment indicates mice that were injected with tumor cells but not T cells. Tumor burden was measured biweekly by bioluminescent imaging. Images of representative time points are shown. Images of three mice from each group were intentionally selected to show mice relapsing after treatment. Disappearance of a mouse from the sequence of images indicates death of that mouse. (D) Kaplan-Meier curve representing the percent survival of the experimental groups described in B (1928z-T-iPSC-T: n=4, 1928z-γδ: n=5, 1928z-αβ: n=7, no treatment: n=6). Color-coded arrows depict death events not related to tumor growth in the corresponding groups. Statistical analysis between the treated experimental and the untreated control group, depicted here, was done using the log-rank test and P<0.05 was considered significant. (E) shows exemplary CAR-T-iPSC-T cells that delayed tumor growth in a murine xenograft model of CD19− Raji Burkit's Lymphoma compared to an untreated control. Peripheral Blood TCRαβ and TCRγδ cells transduced with the 1928z CAR served as positive controls. NOD scid gamma (NSG) mice were inoculated intraperitoneally with $10^5$ Raji cells which are expressing GFP and firefly-luciferase, so that tumor burden could be monitored by in vivo bioluminescence imaging (IVIS 100 Imaging System). Four days later $10^5$ T cells of the respective groups were also injected intraperitoneally together with IL-2 (50.000 U/mouse) and IL-15 (0.25 µg/mouse). IL-2 administration was continued daily and IL-15 every 2 days.

The cytotoxic potential of expanded 1928z-T-iPSCT cells was first evaluated using an in vitro $^{51}$Cr release assay with EL4 murine lymphoma cells expressing CD19 or ovalbumin (nonspecific negative control) as targets (9). Expanded 1928z-T-iPSC-T cells displayed high antigen-specific cytotoxic activity, even at low effector-to-target (E/T) ratios (FIG. 3A). To investigate the anti-tumor activity of 1928z-T-iPSC-T cells in vivo, a xenogeneic tumor model was established. Nonobese diabetic-severe combined immunodeficient NOD-SCID IL2Rγc$^{null}$ mice were inoculated with the CD19$^+$ Raji human Burkitt lymphoma cell line expressing a fluorescent luciferase fusion protein. For comparison to 1928z-T-iPSC-T cells, TCR-αβ and TCR-γδ peripheral blood lymphocytes from the same donor as the T-iPSC line expressing the 1928z CD19 CAR were transduced.

Figures 1, 3B:
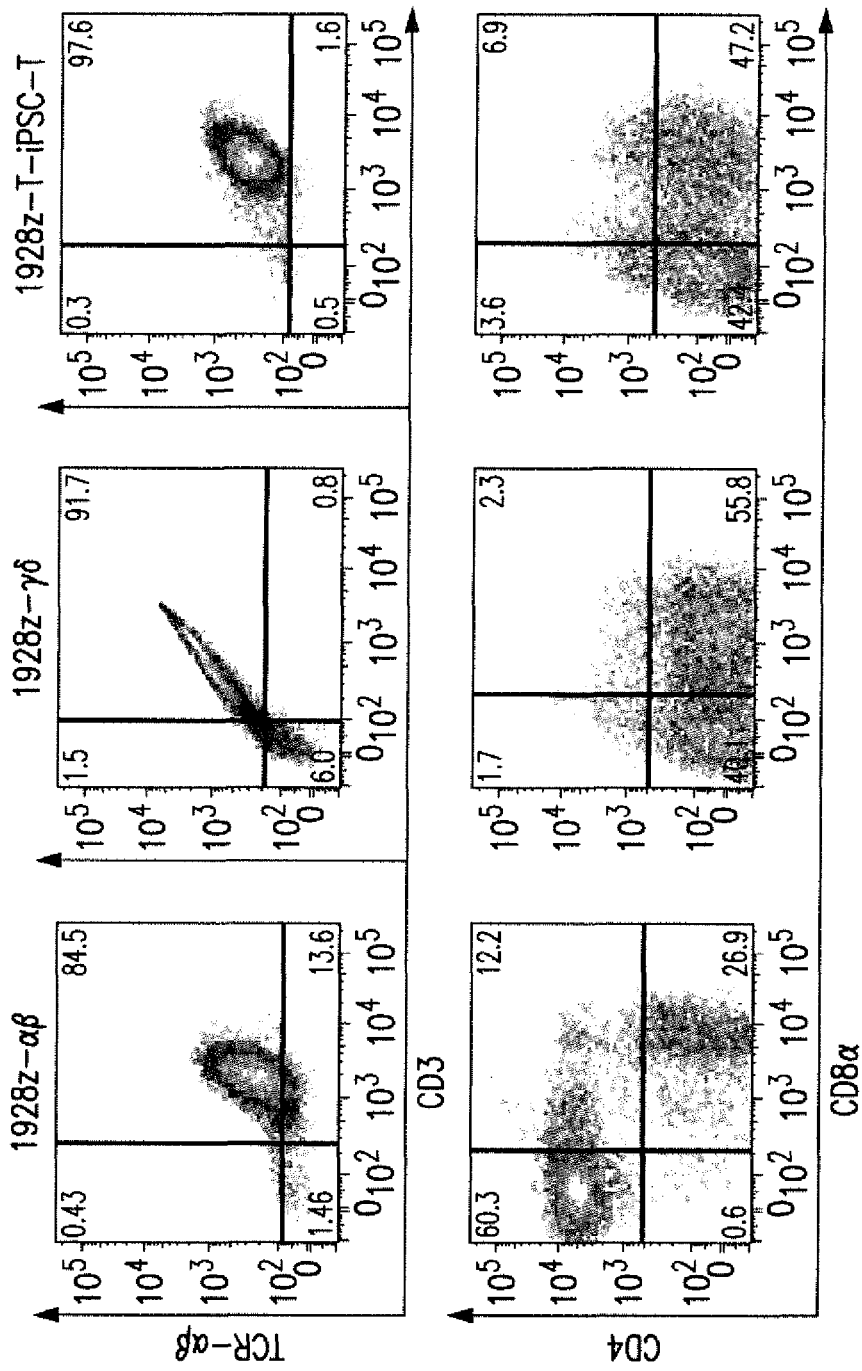
Figures 2, 3B:
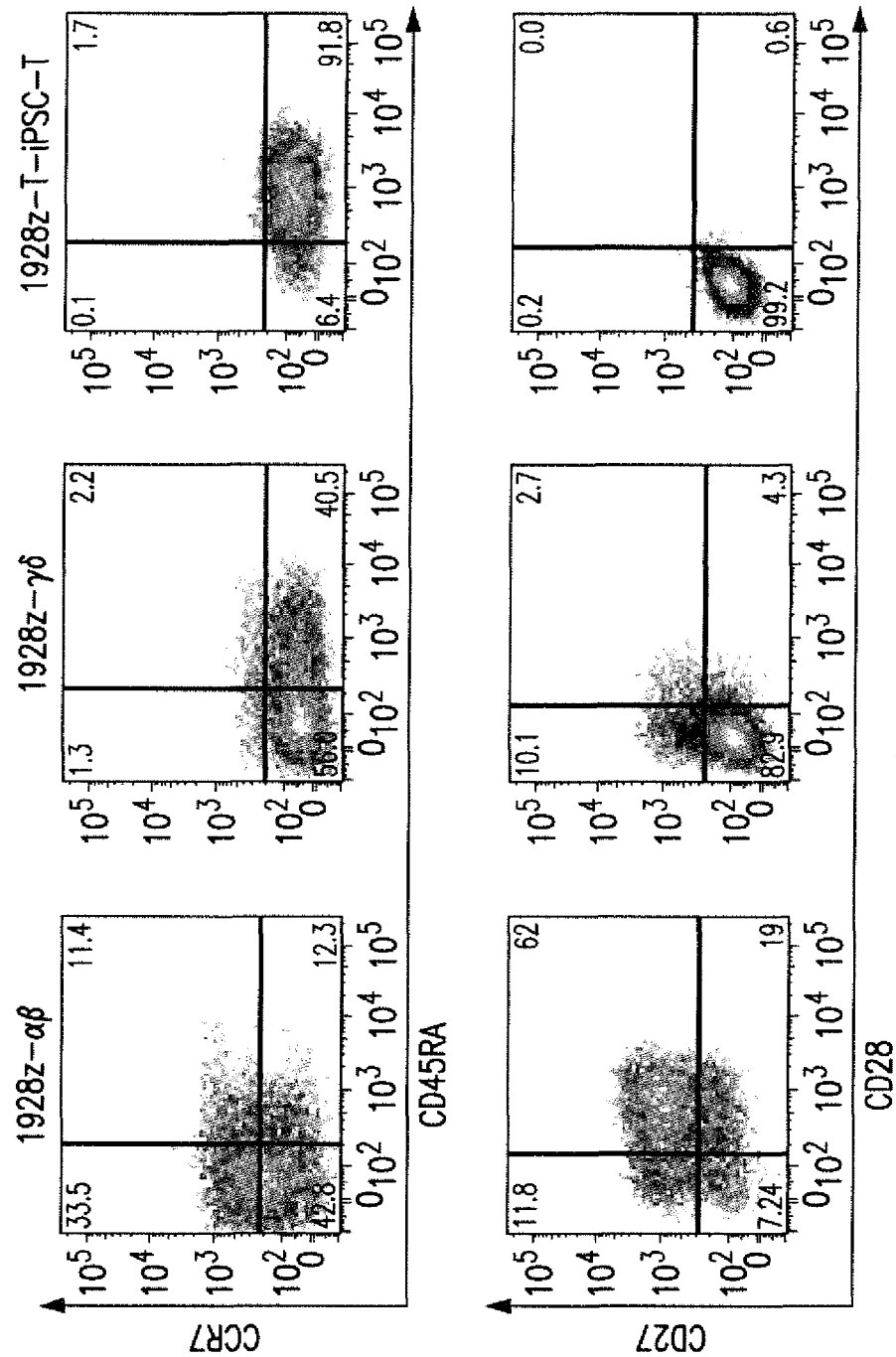
Figures 3, 3B:
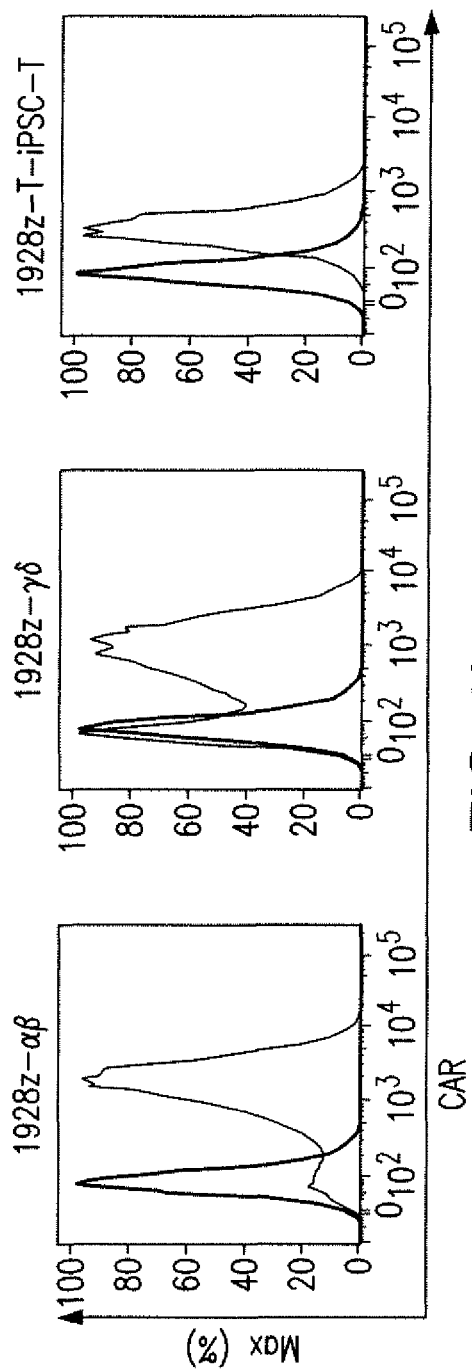

These three T-cell populations showed some phenotypic similarities and some differences. When 1928z-T-iPSC-T cells were expanded for a week, they displayed a TEMRA phenotype (CD45RA$^+$CD27$^-$CD28$^-$CCR7$^-$), similar to the expanded 1928z-γδ T cells. In contrast, a sizeable fraction (33%) of 1928z-αβ T cells displayed a CD45RACD27$^+$CD28$^+$CCR7$^+$ phenotype indicative of central memory cells (FIG. 3B). CAR expression was much lower on 1928z-T-iPSC-T cells (mean fluorescence intensity (MFI)=395) than on 1928z-γδ (MFI=1,212) or 1928z-αβ cells (MFI=2,010) (FIG. 3B), which may influence therapeutic activity (20).

Figure 3C:
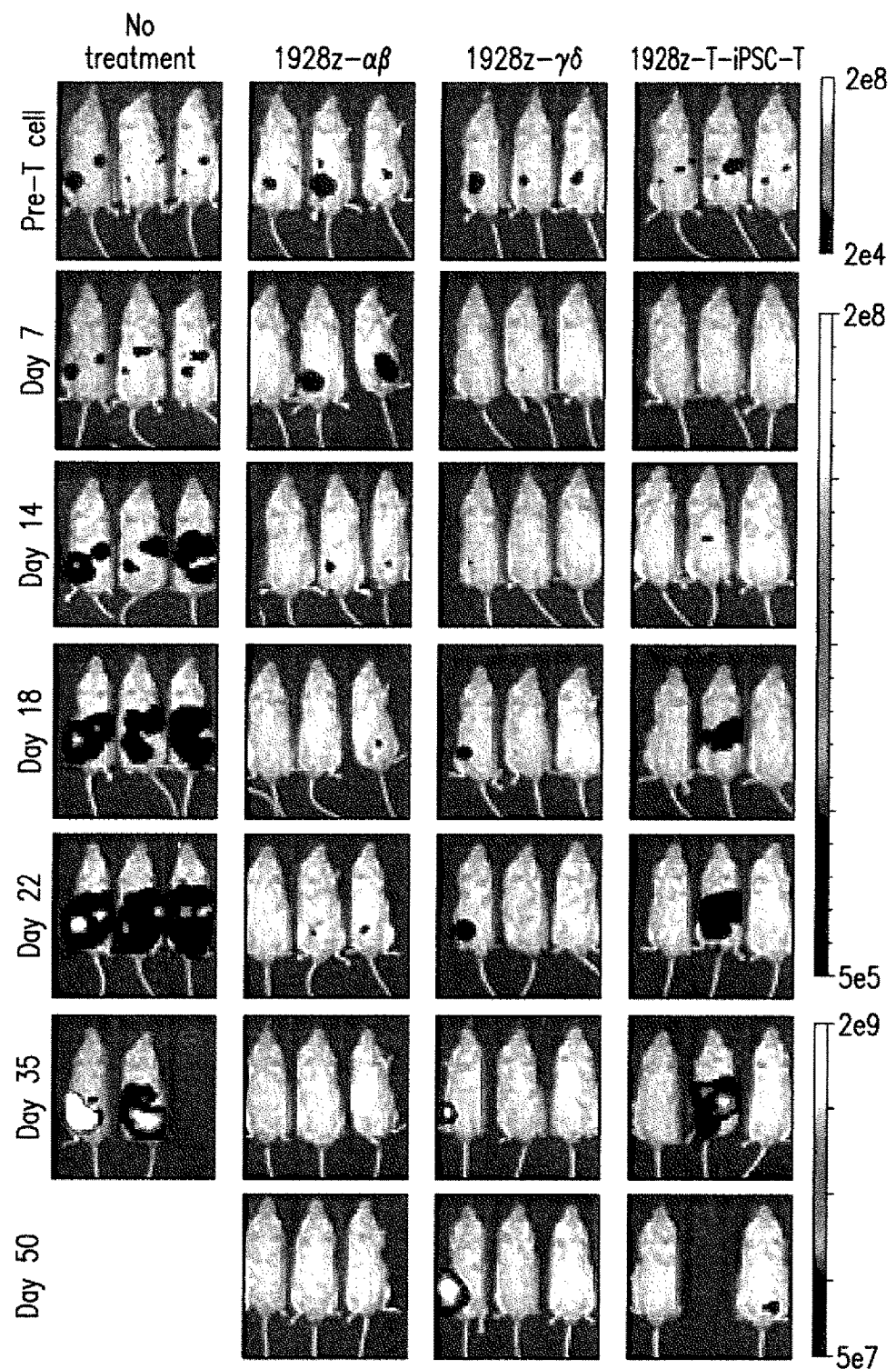
Figure 3D:
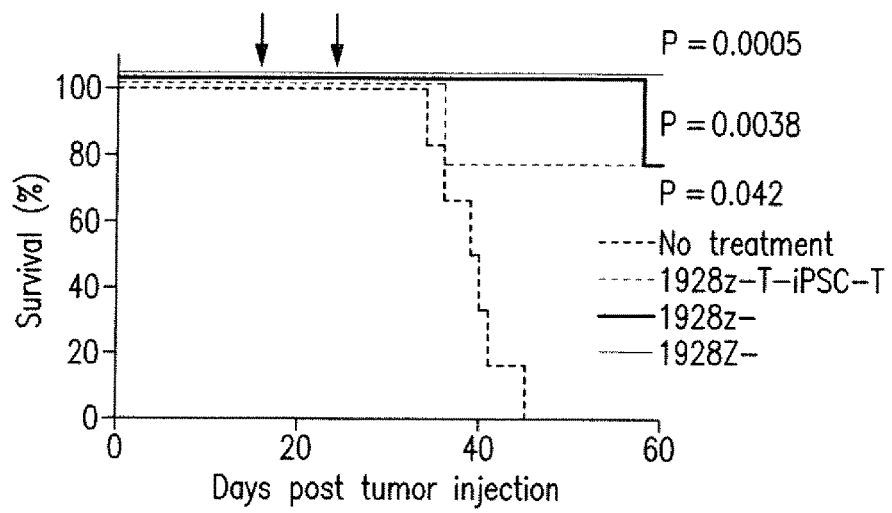
Figure 3E:
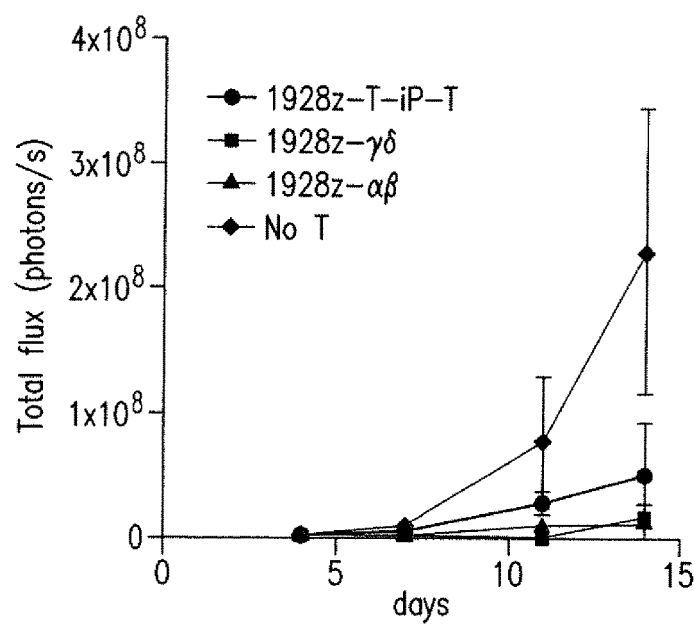
Figure 10:
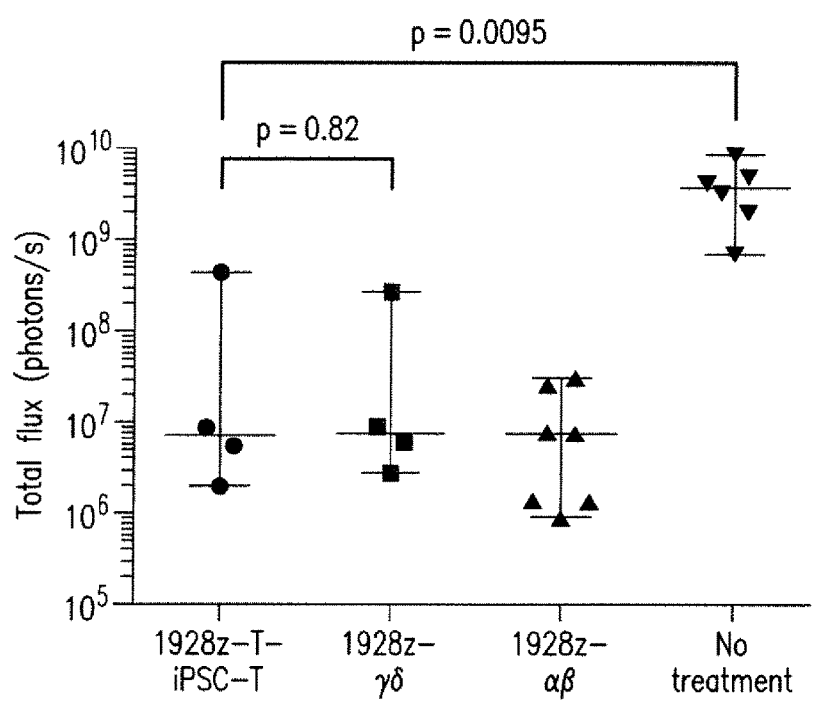
FIG. 10 shows 1928z-T-iPSC-T cells significantly delay CD19-positive tumor progression in vivo. NSG mice were inoculated intraperitoneally with the CD19$^+$ Raji human Burkitt lymphoma cell line expressing a green fluorescent protein-firefly luciferase fusion protein (GFP/Luc). Four days later they were injected i.p. with syngeneic 1928z-T-iPSC-T, 1928z-γδ or 1928z-αβ T cells. No treatment indicates tumor-bearing mice not injected with T cells. Total tumor burden at day 22 after tumor injection was measured by Bioluminescence imaging (BLI) and total flux (photons/sec) is represented. Median±range is plotted. Variances differed between the 1928z-T-iPSC-T and the no treatment group (F test, p=0.0016) but did not differ between the 1928z-T-iPSC-T and 1928z-γδ group (F test, p=0.408). Statistical significance was determined using two-tailed Mann-Whitney test to compare ranks between the 1928z-T-iPSC-T, no treatment and 1928z-γδ groups. Each dot represents one recipient mouse. p<0.05 was considered significant.

As shown by bioluminescent imaging, infusion of 1928z-T-iPSC-T cells delayed tumor progression to an extent similar to that induced by peripheral blood 1928z-γδ cells (FIGS. 3C and 10), and resulted in a significant survival advantage compared to tumor-bearing mice that were not treated with T cells (log-rank P=0.042, Cox proportional hazards regression P=0.036; FIGS. 3D and 3E). Bioluminescence imaging further revealed that 1928z-T-iPSC-T and 1928z-γδ T cells initiated tumor regression more rapidly than 1928z-αβ cells (FIG. 3C). However, although initially slower at inducing tumor regression, the 1928z-αβ T cells did eventually induce complete tumor regression (FIG. 3C). These findings demonstrate that CAR+T-iPSC-T cells can lyse tumor cells in vitro, elicit strong anti-tumor responses in vivo and provide a survival benefit in tumor-bearing animals, to the same degree as their closest natural counterparts.

5. Discussion

Figure 11:
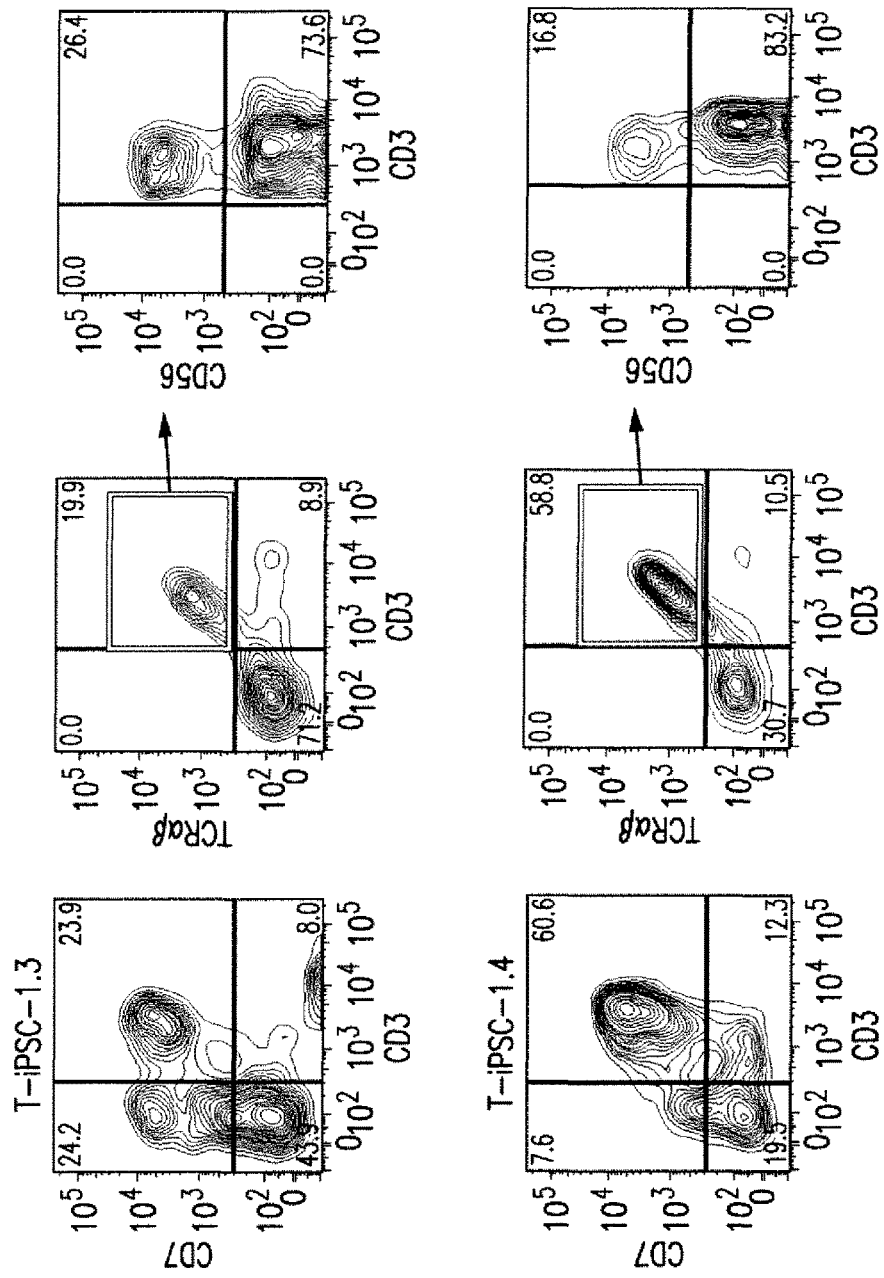
FIG. 11 shows early expression of TCR in T lymphoid differentiation of different T-iPSC clones. Flow cytometric analysis of cells derived from independent clones T-iPSC-1.3 and T-iPSC-1.4 at day 25 of differentiation (day 15 on OP9-DL1 coculture).
Figure 12:
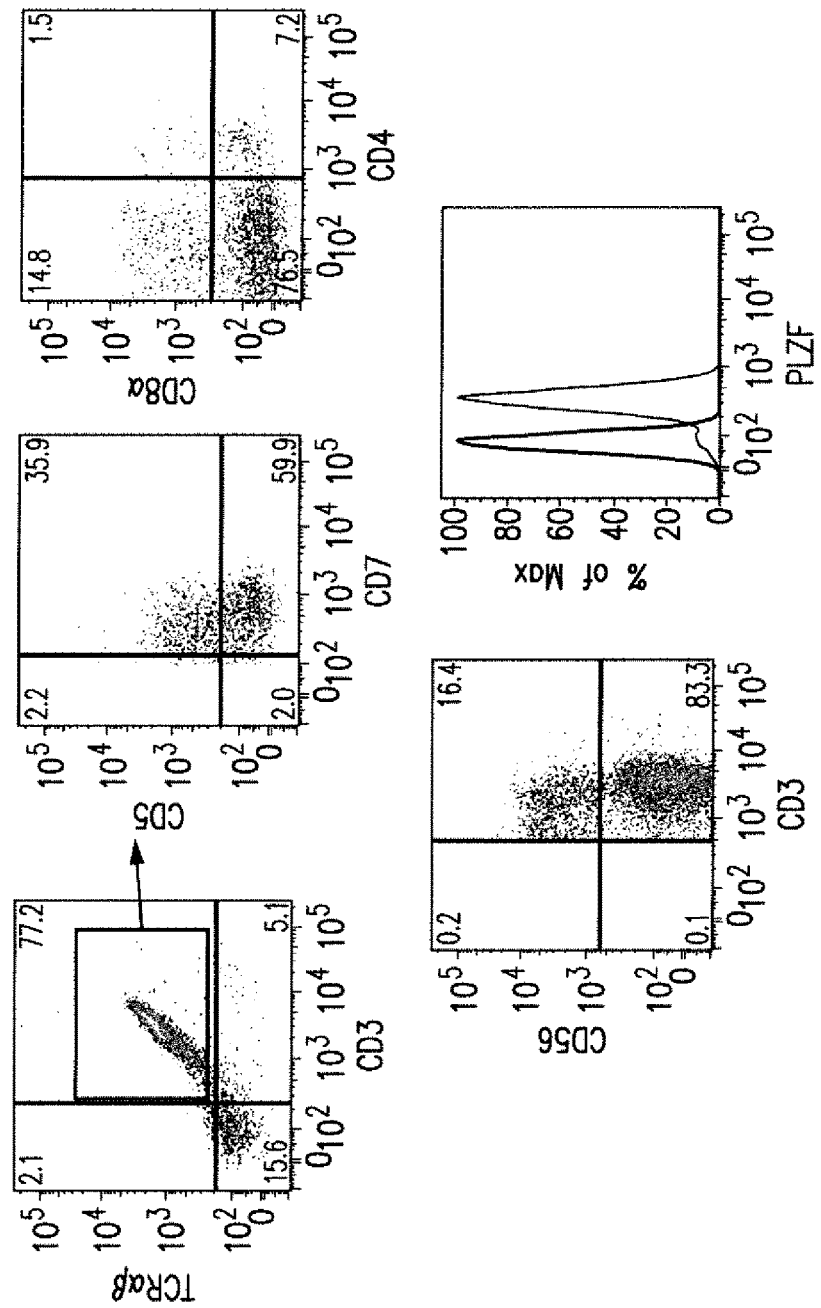
FIG. 12 shows immunophenotype of T lymphocytes derived from non-CAR-engineered T-iPSCs. Flow cytometric analysis of T lymphocytes derived from clone T-iPSC-1.10 at day 30 of differentiation (day 20 on OP9-DL1 co-culture). Figure shows representative plots of at least 5 independent differentiations. Black histogram: isotype control.

The iPSC and CAR technologies, combined as shown here, potentially provide an unlimited source of T lymphocytes targeted to a chosen antigen, independent of HLA restriction. Under the present conditions, starting from T-iPSCs encoding a rearranged endogenous αβ TCR, it was determined that the generated T cells have the properties of γδ T cells, although they express their endogenous αβ TCR on their surface (17, 21). A similar lineage diversion has been observed in mice expressing TCRα and β transgenes, wherein T cells distinct from wild-type NK, NK T cells, or CD4$^+$ or CD8$^+$α β T cells displayed γδ T-cell features, including expression of CD8α and low expression of CD5, CD122 and NK1.1 (22-24). T cells differentiated in vitro from human CD34$^+$ hematopoietic progenitors genetically engineered to express an antigen-specific TCR display an NK cell-like phenotype (25). Together these observations suggest a possible effect of premature expression of TCRαβ, which may skew development toward innate lymphoid-like lineages. Although T-iPSC-derived expanded T cells have been reported to have a CD3$^+$CD7$^+$CD5$^{low}$TCRαβ$^+$CD56$^+$ phenotype associated with expression of CD8α but not CD8β, they were not identified as γδ-like T cells (6). Interestingly, expression of the pre-rearranged endogenous TCRαβ was observed on day 15 of differentiation on OP9-DL1 cells (Table 2), earlier than in some other reports describing T-cell differentiation from human ESC- or iPSC-derived T cells (3, 4). Importantly, the same kinetics of T-cell development as in T-iPSC-1.10 were observed in two other independent T-iPSC lines bearing different TCR rearrangements (FIGS. 5B and 11), but not in cord blood-derived iPSC or in ESCs (data not shown). Altogether, these observations suggest that early expression of a transgenic or endogenous TCRαβ influences the T-cell differentiation process (22-25). In addition, some subtle features of our 1928z-T-iPSC-T cells, such as their CD8α$^+$CD8β$^-$ phenotype, expression of CD161 and low expression of CD5, are shared between adult γδ T cells and innate-like T cells generated in fetal development (17, 18, 21, 26). Together with previous reports, these observations suggest that these lymphoid cells may originate from a fetal cell-like hematopoietic stem cell intermediate committed to innate-like lymphopoiesis and that in vitro differentiation from pluripotent stem cells may be intrinsically skewed toward embryonic characteristics (4, 27, 28). Notably, the CAR, which effectively supported T-cell expansion, did not seem to influence the acquisition of the γδ phenotype, as non-CAR-transduced T-iPSC-1.10 cells also yielded TCRαβ-expressing, γδ-like T cells (FIG. 12). A complete understanding of the maturation of T-iPSC-derived T lymphocytes can further optimize their development and differentiation, generate different T-cell lineages and shape their functional attributes.

Tumor specificity is one of the essential characteristics of T lymphocytes used in adoptive T-cell therapy. Using the protocol described in this Example, any HLA-independent antigen specificity can be imparted to any iPSC through an appropriate CAR, without requiring the establishment of a patient-specific T-cell clone (8). The inventors was not aware of any previously published study reporting that genetic modification of human pluripotent stem cells with a receptor for antigen is an effective approach to generate T cells with therapeutic potential. 1928z-T-iPSC-T cells delayed tumor progression in vivo to a similar extent as peripheral blood-derived 1928z-γδ-T cells from the same donor. γδ T cells have some advantageous properties, such as low graft-versus-host reactivity and the ability to infiltrate solid tumors (29, 30). Their anti-tumor activity has been demonstrated in several clinical settings, mainly against hematological malignancies (30).

CAR-modified T-iPSC-derived T cells may be especially valuable in situations where autologous or allogeneic T cells are not available. This is, for example, the case in immune-deficient patients such as HIV-infected or highly immunosuppressed patients with malignancies; in these scenarios autologous T-cell isolation and expansion is problematic or impossible. CAR-T-iPSC-T cells may also be useful in patients from whom the isolation of autologous tumor-infiltrating T lymphocytes has failed, while providing the additional benefit of targeting alternative antigens recognized by CARs (8, 31). Other patients who could benefit from CAR-T-iPSC-T cells include those with acute leukemia who relapse after allogeneic hematopoietic cell transplantation and for whom the use of allogeneic donor lymphocyte infusions (DLI) is problematic. The efficacy of DLI in those patients is minimal, yet fraught with the risk of graft-versus-host disease (32). CAR-T-iPSC-T cells could thus represent an additional option for patients who do not respond to DLI or for whom DLI use is not indicated due to high risk for graft-versus-host disease.

Several steps can be taken to avert the risks of immunological complications in the context of an off-the-shelf allogeneic CAR-T-iPSC-T therapy. The alloreactivity of T-iPSC-derived T cells, which express an endogenous TCR (FIG. 1A), can be eliminated by either disrupting the TCR, using target site-specific nucleases after T-cell differentiation, or by generating T-iPSCs from virus-specific T cells, which due to their recognition of a pathogen-derived antigen, are less likely to cause graft versus-host disease (33, 34). Allorejection of CAR-iPSC-T cells (which express HLA molecules) can be minimized by generating iPSCs from common HLA haplotypes (to ensure their histocompatibility with matched unrelated recipients) or by repressing HLA expression through additional genetic modification (35, 36). Finally, the risk of insertional oncogenesis secondary to gene transfer can be decreased by integrating the CAR cDNA and other genes, such as suicide genes and noninvasive imaging reporters, at genomic safe harbor sites (37, 38).

In summary, the combination of iPSC and CAR technologies as disclosed in the present invention offers a potential new source of off-the-shelf T cells of predetermined antigen specificity. Considering the versatility of pluripotent stem cells and CAR engineering, this system may facilitate production of different T-cell subpopulations with additional genetic modifications and specificities suitable for a range of therapeutic indications.

Example 2

This example provides exemplary compositions and methods for engineering and providing chimeric T cell receptors (CARs).

Chimeric antigen receptors (CARs) are provided that combine, in a single chimeric species, the intracellular domain of CD3 .zeta.-chain, a signaling region from a costimulatory protein, such as CD28, and a binding element that specifically interacts with a selected target antigen. The engineered construct may further comprise nucleic acid sequences encoding a fluorescent marker. Such as mCherry, eGFP, etc.

For this example, a chimeric T cell receptor was provided comprising nucleic acid sequences for encoding a nucleic acid sequence encoding a protein for B-cell lineage cell surface receptor CD19 antigen recognition, a CD28 costimulatory molecule, and mCherry. Such sequences for CD19 and CD28 are provided in U.S. Pat. No. 7,446,190, which is herein incorporated by reference in its entirety including sequences, viral vectors and methods of using viral vectors for transducing cells and testing function and phenotypes of resulting cells.

Specifically, to construct a CD19 specific CAR, ScFv, the heavy (VH) and light (VL) chain variable regions were cloned from hybridoma cell line SJ25C1 derived cDNA by the polymerase chain reaction (PCR) using degenerate primers described by Orlandi (43) and fused these coding regions with a DNA fragment encoding for a (Gly3Ser) (4) spacer region. A costimulatory signaling element from human CD28, including transmembrane and extracellular portions (U.S. Pat. No. 7,446,190: SEQ ID NO: 6) was ligated to the 3' end of the resulting ScFv and the cytoplasmic domain of the human-.zeta. (U.S. Pat. No. 7,446,190: SEQ ID NO: 3) to the 3' end of the CD28 portion to form fusion gene 19-28z (also termed 1928z).

The mCherry sequence was linked with a P2A peptide upstream of the 1928z fusion gene and the construct was then ligated into the AgeI/SalI restriction sites of a pLM lentiviral vector (Papapetrou et al PNAS 2009) driven by a constitutive ubiquitin C (UbC) promoter.

Lentiviral vector production was done by triple co-transfection of 293T producer cells plated on poly-L-lysine coated 100-mm tissue culture dishes. When the cells were ~80% confluent, the medium (DMEM with 10% FBS and 1 mM L-Glut) was gently replaced with 7 ml of prewarmed medium and incubated for an hour. A plasmid/CaCl2 mix was prepared by adding 10 μg of the lentiviral vector plasmid, 7.5 μg of pCMVΔR8.91, 2.5 μg of pUCMDG, 50 μl of 2.5 M CaCl2 and WFI to a total volume of 500 μl. To transfect, 0.5 ml of plasmid/CaCl2 mix was transferred into a 50-ml conical tube. While vortexing at low speed, 0.5 ml of the 2×HBS buffer was added dropwise using a P1000 pipette. Then 1 ml of the new mix was added to the 100-mm dish of 293T using a P1000 pipette dropwise, scattering the drops uniformly to the entire surface of the dish. 293T cells were incubate at 37° C., 5% CO2 for ~16 h. After 16 h the medium was aspirated and replaced gently with 10 ml prewarmed medium per plate. Cells were incubate at 37° C., 5% CO2 for ~24 h. The following day the vector-containing supernatant is collected and the dishes discarded. The supernatant was centrifuged at 1,000 g at 4° C. for 5 min to pellet cell debris. Then the supernatant was filtered through a 0.45-μm filter, aliquoted and stored at −80° C.

Example 3

This example describes prophetic compositions and methods for providing a "universal" $CAR^+$ cell which is "edited" so that it would not induce graft vs. host symptoms in an allogeneic system or host.

Thus, in one embodiment, compositions and methods are provided to knocking out HLA (class I) cell surface expression in a cell before or after expression of a CAR. In further embodiments, compositions and methods are provided to knocking out HLA (class II) cell surface expression in a cell before or after expression of a CAR. in one embodiment, a TCR is silenced or knocked in. In one embodiment, a costimulatory ligand is silenced or knocked out. in one embodiment, a suicide gene is knocked-in. in one embodiment, a sequence for an inducible cytokine is transduced into a CAR+ cells. in one embodiment, a sequence for an imaging gene is transduced into a CAR+ cells. In some embodiments, a heterologous gene is placed inside of genomic safe harbor site of a cell's genome, In some embodiments inside of a $CAR^+$ cell's genome (Papapetrou, et al., Nat Biotech (2011), herein incorporated by reference). Targeting of this specific safe genomic harbor was achieved by homologous recombination using a nuclease (e.g. TALEN). Further manipulation of CAR-T-PSC includes silencing or knocking out Rag genes in order to avoid re-rearrangement of TCRα chain during redifferentiation and the risk of new TCRαβ pairs to appear. In this way the produced CAR-T-iPSC-derived T cells will express a unique endogenous TCR therefore minimizing the risk of alloreactivity. Through these manipulations the present invention aims to provide CAR-T-PSC-T cells with a universal application potential for including allogeneic transplantation.

Therefore, the compositions and methods as described herein were used to produce engineered antigen specific cells capable of antigen stimulation of effector functions. Further, these engineered cells overcome a yield obstacle of other types of in vitro T-cell differentiation of iPS cells into antigen-specific effector cells.

REFERENCES

1. Sadelain, M., Riviere, I. & Brentjens, R. Targeting tumours with genetically enhanced T lymphocytes. Nat. Rev. Cancer 3, 35-45 (2003).
2. Riddell, S. R. & Greenberg, P. D. Principles for adoptive T cell therapy of human viral diseases. Annu. Rev. Immunol. 13, 545-586 (1995).
3. Timmermans, F. et al. Generation of T cells from human embryonic stem cell-derived hematopoietic zones. J. Immunol. 182, 6879-6888 (2009).
4. Kennedy, M. et al. T lymphocyte potential marks the emergence of definitive hematopoietic progenitors in human pluripotent stem cell differentiation cultures. Cell Rep. 2, 1722-1735 (2012).
5. Vizcardo, R. et al. Regeneration of human tumor antigen-specific T cells from iPSCs derived from mature CD8(+) T cells. Cell Stem Cell 12, 31-36 (2013).
6. Nishimura, T. et al. Generation of rejuvenated antigen-specific T cells by reprogramming to pluripotency and redifferentiation. Cell Stem Cell 12, 114-126 (2013).
7. Takahashi, K. et al. Induction of pluripotent stem cells from adult human fibroblasts by defined factors. Cell 131, 861-872 (2007).
8. Sadelain, M., Brentjens, R. & Riviere, I. The basic principles of chimeric antigen receptor design. Cancer Discov. 3, 388-398 (2013).
9. Brentjens, R. J. et al. Eradication of systemic B-cell tumors by genetically targeted human T lymphocytes co-stimulated by CD80 and interleukin-15. Nat. Med. 9, 279-286 (2003).
10. Maher, J., Brentjens, R. J., Gunset, G., Riviere, I. & Sadelain, M. Human T-lymphocyte cytotoxicity and proliferation directed by a single chimeric TCRzeta/CD28 receptor. Nat. Biotechnol. 20, 70-75 (2002).
11. Kalos, M. et al. T cells with chimeric antigen receptors have potent antitumor effects and can establish memory in patients with advanced leukemia. Sci. Transl. Med. 3, 95ra73 (2011).
12. Brentjens, R. J. et al. Safety and persistence of adoptively transferred autologous CD19-targeted T cells in patients with relapsed or chemotherapy refractory B-cell leukemias. Blood 118, 4817-4828 (2011).
13. Kochenderfer, J. N. et al. B-cell depletion and remissions of malignancy along with cytokine-associated toxicity in a clinical trial of anti-CD19 chimeric-antigen-receptor-transduced T cells. Blood 119, 2709-2720 (2012).
14. Brentjens, R. J. et al. CD19-targeted T cells rapidly induce molecular remissions in adults with chemotherapy-refractory acute lymphoblastic leukemia. Sci. Transl. Med. 5, 177ra138 (2013).
15. Slukvin, I. I. Deciphering the hierarchy of angiohematopoietic progenitors from human pluripotent stem cells. Cell Cycle 12, 720-727 (2013).
16. Pont, F. et al. The gene expression profile of phosphoantigen-specific human gammadelta T lymphocytes is a blend of alphabeta T-cell and NK-cell signatures. Eur. J. Immunol. 42, 228-240 (2012).
17. Ness-Schwickerath, K. J. & Morita, C. T. Regulation and function of IL-17A- and IL-22-producing gammadelta T cells. Cell. Mol. Life Sci. 68, 2371-2390 (2011).
18. Spits, H. & Cupedo, T. Innate lymphoid cells: emerging insights in development, lineage relationships, and function. Annu. Rev. Immunol. 30, 647-675 (2012).
19. Muranski, P. et al. Th17 cells are long lived and retain a stem cell-like molecular signature. Immunity 35, 972-985 (2011).
20. Turatti, F. et al. Redirected activity of human antitumor chimeric immune receptors is governed by antigen and receptor expression levels and affinity of interaction. J. Immunother. 30, 684-693 (2007).
21. Pang, D. J., Neves, J. F., Sumaria, N. & Pennington, D. J. Understanding the complexity of gammadelta T-cell subsets in mouse and human. Immunology 136, 283-290 (2012).
22. Terrence, K., Pavlovich, C. P., Matechak, E. O. & Fowlkes, B. J. Premature expression of T cell receptor (TCR) alphabeta suppresses TCRgammadelta gene rearrangement but permits development of gammadelta lineage T cells. J. Exp. Med. 192, 537-548 (2000).
23. Baldwin, T. A., Sandau, M. M., Jameson, S. C. & Hogquist, K. A. The timing of TCR alpha expression critically influences T cell development and selection. J. Exp. Med. 202, 111-121 (2005).
24. Egawa, T., Kreslavsky, T., Littman, D. R. & von Boehmer. H. Lineage diversion of T cell receptor transgenic thymocytes revealed by lineage fate mapping. PLoS One 3, e1512 (2008).
25. Zhao, Y. et al. Extrathymic generation of tumor-specific T cells from genetically engineered human hematopoietic stem cells via Notch signaling. Cancer Res. 67, 2425-2429 (2007).
26. Cupedo, T. et al. Human fetal lymphoid tissue-inducer cells are interleukin 17-producing precursors to RORC+ CD127+ natural killer-like cells. Nat. Immunol. 10, 66-74 (2009).
27. Yuan, J., Nguyen, C. K., Liu, X., Kanellopoulou, C. & Muljo, S. A. Lin28b reprograms adult bone marrow hematopoietic progenitors to mediate fetal-like lymphopoiesis. Science 335, 1195-1200 (2012).
28. Murry, C. E. & Keller, G. Differentiation of embryonic stem cells to clinically relevant populations: lessons from embryonic development. Cell 132, 661-680 (2008).
29. Bonneville, M., O'Brien, R. L. & Born, W. K. Gammadelta T cell effector functions: a blend of innate programming and acquired plasticity. Nat. Rev. Immunol. 10, 467-478 (2010).
30. Fournié, J. J. et al. What lessons can be learned from gammadelta T cell-based cancer immunotherapy trials-?Cell. Mol. Immunol. 10, 35-41 (2013).
31. Goff, S. L. et al. Tumor infiltrating lymphocyte therapy for metastatic melanoma: analysis of tumors resected for TIL. J. Immunother. 33, 840-847 (2010).
32. Collins, R. H. Jr. et al. Donor leukocyte infusions in 140 patients with relapsed malignancy after allogeneic bone marrow transplantation. J. Clin. Oncol. 15, 433-444 (1997).
33. Provasi, E. et al. Editing T cell specificity towards leukemia by zinc finger nucleases and lentiviral gene transfer. Nat. Med. 18, 807-815 (2012).
34. Doubrovina, E. et al. Adoptive immunotherapy with unselected or EBV-specific T cells for biopsy-proven EBV+ lymphomas after allogeneic hematopoietic cell transplantation. Blood 119, 2644-2656 (2012).
35. Taylor, C. J., Peacock, S., Chaudhry, A. N., Bradley, J. A. & Bolton, E. M. Generating an iPSC bank for HLA-matched tissue transplantation based on known donor and recipient HLA types. Cell Stem Cell 11, 147-152 (2012).

36. Riolobos, L. et al. HLA engineering of human pluripotent stem cells. Mol. Ther. 2, 1232-1241 (2013).
37. Ellis, J. et al. Benefits of utilizing gene-modified iPSCs for clinical applications. Cell Stem Cell 7, 429-430 (2010).
38. Papapetrou, E. P. et al. Genomic safe harbors permit high beta-globin transgene expression in thalassemia induced pluripotent stem cells. Nat. Biotechnol. 29, 73-78 (2011).
39. Schmitt, T. M. & Zuniga-Pflucker, J. C. Induction of T cell development from hematopoietic progenitor cells by delta-like-1 in vitro. Immunity 17, 749-756 (2002).
40. Markley, J. C. & Sadelain, M. IL-7 and IL-21 are superior to IL-2 and IL-15 in promoting human T cell-mediated rejection of systemic lymphoma in immunodeficient mice. Blood 115, 3508-3519 (2010).
41. Brentjens, R. J. et al. Genetically targeted T cells eradicate systemic acute lymphoblastic leukemia xenografts. Clin. Cancer Res. 13, 5426-5435 (2007).
42. Grambsch, M. P. & Therneau, M. T. Proportional hazards tests and diagnostics based on weighted residuals. Biometrika 81, 515-526 (1994).
43. Papapetrou E P, Sadelain M., Derivation of genetically modified human pluripotent stem cells with integrated transgenes at unique mapped genomic sites. Nat Protoc. 2011 Aug. 4; 6(9): 1274-89.3.

All publications and patents disclosed in the above specification are herein incorporated by reference. Various modifications and variations of the described method and system of the invention will be apparent to those skilled in the art without departing from the scope and spirit of the invention. Although the present invention has been described in connection with some specific preferred embodiments, it should be understood that the invention as claimed should not be unduly limited to such specific embodiments. Indeed, various modifications of the described modes for carrying out the invention that are obvious to those skilled in immunology, adoptive cell therapy, cellular biology, cancer cell biology, biochemistry, chemistry, organic synthesis, imaging diagnostics or related fields are intended to be within the scope of the following claims.

What is claimed is:

1. A population of T cells that are produced by in vitro differentiation of a pluripotent stem cell, wherein (i) the pluripotent stem cell expresses a chimeric antigen receptor (CAR), and (ii) the population of T cells comprises a T cell exhibiting a CD45RA$^+$CD27$^-$CD28$^-$CCR7$^-$CD62L$^-$ phenotype.

2. The population of claim 1, wherein T cells of said population target specifically to one antigen, and said antigen specificity is HLA-independent.

3. The population of claim 1, wherein said CAR is encoded by a nucleic acid sequence that is a heterologous sequence.

4. The population of claim 3, wherein said heterologous sequence is integrated into said pluripotent stem cell's genome at a genomic safe harbor site.

5. The population of claim 2, wherein said antigen is a tumor antigen or a pathogen antigen.

6. The population of claim 5, wherein the antigen is selected from the group consisting of carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, an antigen of a cytomegalovirus (CMV) infected cell, epithelial glycoprotein2 (EGP 2), epithelial glycoprotein-40 (EGP-40), epithelial cell adhesion molecule (EpCAM), receptor tyrosine-protein kinases erb B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), melanoma antigen family A, 1 (MAGE-AI), Mucin 16 (Muc-16), Mucin 1 (Muc-1), Mesothelin (MSLN), NKG2D ligands, cancer-testis antigen NY-ESO-1, oncofetal antigen (h5T4), prostate stem cell antigen (PSCA), prostate-specific membrane antigen (PSMA), tumor associated glycoprotein 72 (TAG-72), vascular endothelial growth factor R2 (VEGF R2), and Wilms tumor protein (WT-1).

7. The population of claim 1, wherein said CAR comprises a single-chain variable fragment (scFv).

8. The population of claim 1, wherein said CAR comprises one or more of a CD3ζ polypeptide, a CD4 polypeptide, a CD8 polypeptide, a CD28 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, or a BTLA polypeptide.

9. The population of claim 8, wherein said CAR comprises a CD3ζ polypeptide.

10. The population of claim 9, wherein said CAR further comprises a CD28 polypeptide, a 4-1BB polypeptide, an OX40 polypeptide, an ICOS polypeptide, a PD-1 polypeptide, a CTLA-4 polypeptide, a LAG-3 polypeptide, a 2B4 polypeptide, or a BTLA polypeptide.

11. The population of claim 1 wherein said CAR is 1928z.

12. The population of claim 1, wherein T cells of said population comprise a silenced gene selected from the group consisting of a HLA gene transcription factor and a beta-2 microglobulin for an HLA gene.

13. The population of claim 1, wherein T cells of said population comprise a T helper cell, a cytotoxic T cell, a memory T cell, a regulatory T cell, a Natural killer T cell, a Mucosal associated invariant T cell, a γδ T cell, or a combination thereof.

14. The population of claim 1, wherein said pluripotent stem cell is an embryonic stem cell or an induced pluripotent stem cell.

15. The population of claim 1, wherein said pluripotent stem cell is an induced pluripotent stem cell.

16. A method of reducing tumor burden in a subject, comprising administering a population of T cells generated from a pluripotent stem cell that expresses a chimeric antigen receptor (CAR) to said subject having tumor, wherein the population of T cells comprises a T cell exhibiting a CD45RA$^+$CD27$^-$CD28$^-$CCR7$^-$CD62L$^-$ phenotype.

17. The method of claim 16, wherein said T cell is cytotoxic to said tumor.

18. The method of claim 16, wherein said tumor cell expresses a tumor antigen and said T cells target specifically to said tumor antigen.

19. The method of claim 18, wherein antigen-specificity of said T cell is HLA-independent.

20. The method of claim 16, wherein said pluripotent stem cell is an embryonic stem cell or an induced pluripotent stem cell.

21. The method of claim 20, wherein said pluripotent stem cell is an induced pluripotent stem cell.

22. The method of claim 21, wherein said pluripotent stem cell is derived from a T cell.

23. The method of claim 22, wherein said pluripotent stem cell expresses one ligand for immunoregulatory T cell receptor, wherein said ligand is selected from the group consisting of PD-L1, CD48 and TNFRSF14.

24. The method of claim 22, wherein said pluripotent stem cell expresses HLA-G.

25. The method of claim 21, wherein said pluripotent stem cell is derived from a viral-specific T cell.

26. The method of claim 25, wherein the viral-specific T cell is a EBV-specific T-cell or a CMV-specific T-cell.

27. The method of claim 21, wherein said pluripotent stem cell is derived from a T cell that does not express a rearranged T-cell receptor (TCR).

28. The method of claim 18, wherein said tumor antigen is selected from the group consisting of carbonic anhydrase IX (CAlX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, an antigen of a cytomegalovirus (CMV) infected cell, epithelial glycoprotein2 (EGP 2), epithelial glycoprotein-40 (EGP-40), epithelial cell adhesion molecule (Ep-CAM), receptor tyrosine-protein kinases erb B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), melanoma antigen family A, 1 (MAGE-AI), Mucin 16 (Muc-16), Mucin 1 (Muc-1), Mesothelin (MSLN), NKG2D ligands, cancer-testis antigen NY-ESO-1, oncofetal antigen (h5T4), prostate stem cell antigen (PSCA), prostate-specific membrane antigen (PSMA), tumor associated glycoprotein 72 (TAG-72), vascular endothelial growth factor R2 (VEGF R2), and Wilms tumor protein (WT-1).

29. The method of claim 16, wherein said T cell does not induce graft vs. host disease in said subject.

30. The method of claim 16, wherein said CAR comprises a single-chain variable fragment (scFv).

31. The method of claim 16, wherein said CAR comprises one or more of a CD3ζ polypeptide, a CD4 polypeptide, a CD8 polypeptide, a CD28 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, and a BTLA polypeptide.

32. The method of claim 16, wherein said CAR comprises a CD3t polypeptide.

33. The method of claim 32, wherein said CAR further comprises a CD28 polypeptide, a 4-1BB polypeptide, an OX40 polypeptide, an ICOS polypeptide, a PD-1 polypeptide, a CTLA-4 polypeptide, a LAG-3 polypeptide, a 2B4 polypeptide, or a BTLA polypeptide.

34. The method of claim 16, wherein said CAR is 1928z.

35. The method of claim 16, wherein said method reduces the number of tumor cells.

36. The method of claim 16, wherein said method reduces tumor size.

37. The method of claim 16, wherein said method eradicates the tumor in the subject.

38. The method of claim 16, wherein said T cell is selected from the group consisting of T helper cells, cytotoxic T cells, memory T cells, regulatory T cells, Natural killer T cells, Mucosal associated invariant T cells, γδ T cells, and a combination thereof.

39. The method of claim 16, wherein said T cell comprises a silenced gene selected from the group consisting of a HLA gene transcription factor and a beta-2 microglobulin for an HLA gene.

40. The method of claim 16, wherein said T cell expresses Foxp3.

41. The method of claim 16, wherein said subject is a human.

42. A method of increasing survival of a subject having neoplasia, comprising administering a population of T cells generated from a pluripotent stem cell that expresses a chimeric antigen receptor (CAR) to said subject diagnosed with neoplasia, wherein the population of T cells comprises a T cell exhibiting a CD45RA$^+$CD27$^-$CD28$^-$CCR7$^-$CD62L$^-$ phenotype.

43. The method of claim 42, wherein said T cell is cytotoxic to said neoplasia.

44. The method of claim 42, wherein said T cell specifically targets an antigen of said neoplasia and said antigen specificity is HLA-independent.

45. The method of claim 42, wherein said pluripotent stem cell is an embryonic stem cell or an induced pluripotent stem cell.

46. The method of claim 45, wherein said pluripotent stem cell is an induced pluripotent stem cell.

47. The method of claim 46, wherein said pluripotent stem cell is derived from a T cell.

48. The method of claim 47, wherein said pluripotent stem cell expresses one ligand for immunoregulatory T cell receptor, wherein said ligand is selected from the group consisting of PD-L1, CD48 and TNFRSF14.

49. The method of claim 47, wherein said pluripotent stem cell expresses HLA-G.

50. The method of claim 46, wherein said pluripotent stem cell is derived from a viral-specific T cell.

51. The method of claim 50, wherein the viral-specific T cell is a EBV-specific T-cell or a CMV-specific T-cell.

52. The method of claim 47, wherein said pluripotent stem cell is derived from a T cell that does not express a rearranged T-cell receptor (TCR).

53. The method of claim 42, wherein said neoplasia is selected from the group consisting of blood cancer, B cell leukemia, multiple myeloma, lymphoblastic leukemia (ALL), chronic lymphocytic leukemia, non-Hodgkin's lymphoma, ovarian cancer, prostate cancer, pancreatic cancer, lung cancer, breast cancer, sarcoma, and acute myeloid leukemia (AML).

54. The method of claim 42, wherein said CAR comprises a single-chain variable fragment (scFv).

55. The method of claim 42, wherein said CAR comprises one or more of a CD3ζ polypeptide, a CD4 polypeptide, a CD8 polypeptide, a CD28 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, and a BTLA polypeptide.

56. The method of claim 42, wherein said CAR comprises a CD3t polypeptide.

57. The method of claim 56, wherein said CAR further comprises a CD28 polypeptide, a 4-1BB polypeptide, an OX40 polypeptide, an ICOS polypeptide, a PD-1 polypeptide, a CTLA-4 polypeptide, a LAG-3 polypeptide, a 2B4 polypeptide, or a BTLA polypeptide.

58. The method of claim 42, wherein said CAR is 1928z.

59. The method of claim 42, wherein said T cell is selected from the group consisting of T helper cells, cytotoxic T cells, memory T cells, regulatory T cells, Natural killer T cells, Mucosal associated invariant T cells, γδ T cells, and a combination thereof.

60. The method of claim 42, wherein said T cell comprises a silenced gene selected from the group consisting of a HLA gene transcription factor and a beta-2 microglobulin for an HLA gene.

61. The method of claim 42, wherein said T cell expresses Foxp3.

62. The method of claim 42, wherein said subject is a human.

63. A pharmaceutical composition comprising an effective amount of said population of T cells of claim 1 in a pharmaceutically acceptable excipient.

64. A kit for treatment of a neoplasia, pathogen infection, an autoimmune disorder, or an allogeneic transplant, the kit comprising a population of T cells of claim 1.

65. The kit of claim 64, wherein T cells of said population target specifically to one antigen, and said antigen specificity is HLA-independent.

66. The kit of claim 64, wherein said kit further comprises written instructions for using said population for said treatment of a subject diagnosed with a neoplasia, a pathogen infection, an autoimmune disorder, or an allogeneic transplant.

67. The population of claim 1, wherein said pluripotent stem cell further comprises a rearranged T-cell receptor (TCR) locus.

68. The population of claim 67, wherein the rearranged T-cell receptor (TCR) locus is comprised in said T cells produced from said pluripotent stem cell.

69. The population of claim 1, wherein said pluripotent stem cell is derived from reprogramming an isolated T cell.

70. The population of claim 1, wherein said pluripotent stem cell further comprises at least one genetic manipulation.

71. The population of claim 1, wherein said pluripotent stem cell has reduced or undetectable cell surface expression of (i) MHC molecules; (ii) HLA molecules; or (iii) HLA class I molecules.

72. The population of claim 1, wherein said pluripotent stem cell comprises reduced or knocked-out expression in at least one of: (i) Rag gene; (ii) CIITA gene; and (iii) beta-2 microglobulin gene; and/or has expression in Foxp3 gene.

73. The population of claim 1, wherein said pluripotent stem cell further comprises at least one of: a costimulatory signal, a suicide gene, an inducible cytokine, an imaging gene, and a combination thereof.

74. The population of claim 73, wherein the at least one costimulatory signal is (i) co-expressed with the CAR as a costimulatory ligand protein; or (ii) is comprised within an intracellular domain of the CAR.

75. The population of claim 74, wherein the at least one costimulatory signal is co-expressed with the CAR as a costimulatory ligand protein.

76. The population of claim 75, wherein the costimulatory ligand protein is selected from the group consisting of CD80, CD86, CD70, OX40L, 4-1BBL, CD48, TNFRSF14, and PD-L1.

77. The population of claim 74, wherein the at least one costimulatory signal is comprised within the CAR intracellular domain.

78. The population of claim 77, wherein the costimulatory signal is selected from from the group consisting of a CD28 polypeptide, a 4-IBB polypeptide, an OX40 polypeptide, an ICOS polypeptide, a PD-1 polypeptide, a LAG-3 polypeptide, a 2B4 polypeptide, a BTLA polypeptide, and a CTLA-4 polypeptide.

79. The population of claim 68, wherein said pluripotent stem cell does not express the TCR.

80. The population of claim 1, wherein T cells of said population express the CAR.

81. The population of claim 80, wherein T cells of said population are expandable under stimulation using an antigen specific to the CAR.

82. The population of claim 80, wherein T cells of said population further comprise at least one genetic manipulation.

83. The population of claim 80, wherein T cells of said population have reduced or undetectable cell surface expression of (i) WIC molecules; (ii) HLA molecules; or (iii) HLA class I molecules.

84. The population of claim 80, wherein T cells of said population further have reduced or knocked-out expression in at least one of: (i) Rag gene; (ii) CIITA gene; and (iii) beta-2 microglobulin gene; and/or has expression in Foxp3 gene.

85. The population of claim 80, wherein T cells of said population further comprise at least one of: a costimulatory ligand, a suicide gene, an inducible cytokine, an imaging gene, and a combination thereof.

86. The population of claim 85, wherein the costimulatory signal is (i) co-expressed with the CAR as a costimulatory ligand protein; or (ii) is comprised within the CAR protein.

87. The population of claim 68, wherein T cells of said population express the TCR.

88. The population of claim 68, wherein T cells of said population have disrupted or silenced expression of TCR.

89. The population of claim 1, wherein the expressed CAR comprised in the pluripotent stem cell improves T cell differentiation and expansion.

90. The population of claim 3, wherein the CAR encoded by the heterologous nucleic acid sequence comprises an extracellular domain, a transmembrane domain, an intracellular domain, and optionally one or both of (i) a spacer region linking the extracellular domain and the transmembrane domain; and (ii) an inducible promoter; and wherein the extracellular domain comprises an antigen binding region for a predetermined antigen.

91. The population of claim 90, wherein the predetermined antigen is a tumor antigen, a pathogen antigen, or a CD antigen.

92. The population of claim 90, wherein the extracellular domain further comprises a signal peptide.

93. The population of claim 90, wherein the intracellular domain comprises one or more costimulatory receptors.

94. The population of claim 1, wherein T cells of said population are capable of at least one of:
   (i) in vitro and in vivo expansion;
   (ii) in vitro and in vivo persistence;
   (iii) HLA-independent stimulation or activation;
   (iv) in vitro and in vivo cytotoxicity and cytokine production; and
   (v) known TCR specificity.

95. The population of claim 69, wherein said isolated T cell is genetically modified.

96. The kit of claim 64, wherein the population of T cells are produced by in vitro differentiation of a pluripotent stem cell, and wherein the pluripotent stem cell is derived from reprogramming an isolated T cell.

* * * * *